United States Patent
Barnes et al.

(10) Patent No.: US 11,642,339 B2
(45) Date of Patent: May 9, 2023

(54) METHODS OF TREATING SYMPTOMS OF GASTROPARESIS USING VELUSETRAG

(71) Applicants: THERAVANCE BIOPHARMA R&D IP, LLC, South San Francisco, CA (US); ALFASIGMA S.P.A., Bologna (IT)

(72) Inventors: Christopher Noel Barnes, San Francisco, CA (US); Giuseppe Claudio Viscomi, Bologna (IT); Cecilia Renzulli, Bologna (IT); Maria Grimaldi, Bologna (IT)

(73) Assignees: THERAVANCE BIOPHARMA R&D IP, LLC, South San Francisco, CA (US); ALFASIGMA S.P.A., Bologna (IT)

( * ) Notice: Subject to any disclaimer, the term of this patent is extended or adjusted under 35 U.S.C. 154(b) by 0 days.

(21) Appl. No.: 16/048,933

(22) Filed: Jul. 30, 2018

(65) Prior Publication Data

US 2019/0030022 A1  Jan. 31, 2019

Related U.S. Application Data

(60) Provisional application No. 62/539,229, filed on Jul. 31, 2017.

(51) Int. Cl.
| | |
|---|---|
| *A61K 31/4704* | (2006.01) |
| *A61P 1/08* | (2006.01) |
| *A61P 1/06* | (2006.01) |
| *A61P 1/04* | (2006.01) |
| *A61K 9/48* | (2006.01) |
| *A61K 31/55* | (2006.01) |

(52) U.S. Cl.
CPC ........ *A61K 31/4704* (2013.01); *A61K 9/4858* (2013.01); *A61K 9/4866* (2013.01); *A61K 31/55* (2013.01); *A61P 1/04* (2018.01); *A61P 1/06* (2018.01); *A61P 1/08* (2018.01)

(58) Field of Classification Search
CPC ............... A61K 31/4704; A61K 31/55; A61K 9/4858; A61K 9/4866; A61P 1/04; A61P 1/06; A61P 1/08
See application file for complete search history.

(56) References Cited

U.S. PATENT DOCUMENTS

| | | | |
|---|---|---|---|
| 7,375,114 B2 | 5/2008 | Marquess et al. | |
| 7,592,355 B2 | 9/2009 | Marquess et al. | |
| 7,671,198 B2 | 3/2010 | Genov et al. | |
| 7,728,004 B2 | 6/2010 | Fatheree et al. | |
| 7,728,006 B2 | 6/2010 | Marquess et al. | |
| 7,763,637 B2 | 7/2010 | Marquess et al. | |
| 8,163,920 B2 | 4/2012 | Marquess et al. | |
| 8,309,575 B2 | 11/2012 | Marquess et al. | |
| 8,404,711 B2 | 3/2013 | Beattie et al. | |
| 8,575,192 B2 | 11/2013 | Marquess et al. | |
| 8,658,671 B2 | 2/2014 | Fatheree et al. | |
| 8,962,653 B2 | 2/2015 | Marquess et al. | |
| 9,126,994 B2 | 9/2015 | Fatheree et al. | |
| 9,353,106 B2 | 5/2016 | Marquess et al. | |
| 9,402,840 B2 | 8/2016 | Fatheree et al. | |
| 9,630,960 B2 | 4/2017 | Marquess et al. | |
| 9,873,692 B2 | 1/2018 | Marquess et al. | |
| 2005/0228014 A1 | 10/2005 | Marquess et al. | |
| 2006/0229332 A1* | 10/2006 | Fatheree ................ | A61K 31/46 514/304 |

FOREIGN PATENT DOCUMENTS

| | | |
|---|---|---|
| EP | 1735304 B1 | 1/2009 |
| WO | 2013/024164 A1 | 2/2013 |

OTHER PUBLICATIONS

NCT01718938, Clinical Trials.gov, Nov. 1, 2012. (Year: 2012).*
Revicki et al, Quality of Life Research 13 : 833-844, 2004. (Year: 2004).*
NCT02267525, Clinical Trials.gov, Oct. 17, 2014 (Year: 2014).*
McCallum et al., Clinical Gastroenterology and Hepatology 2010;8:947-954 (Year: 2010).*
Loyd et al., Am Fam Physician. 2011;83(5):547-552 (Year: 2011).*
Bruce, WebMD, 2007 (Year: 2007).*
Alam et al., "Diabetic gastroparesis: Therapeutic options", Diabetes Ther, 1(1): 32-43 (2010).
Beattie et al., "An in vitro investigation of the cardiovascular effects of the 5-HT4 receptor selective agonists, velusetrag and TD-8954", Vascular Pharmacology, 58: 150-156 (2013).
Bharucha, "Epidemiology and natural history of gastroparesis", Gastroenterol Clin North Am, 44(1): 9-19 (Mar. 2015).
Camilleri et al., "Clinical guideline: Management of gastroparesis", Am J Gastroenterol, 108(1): 18-38 (Jan. 2013).
Cherian et al., "Abdominal pain is a frequent symptom of gastroparesis", Clinical Gastroenterology and Hepatology, 8(8): 676-681 (2010).
Goldberg et al., "Clinical trial: the efficacy and tolerability of velusetrag, a selective 5-HT4 agonist with high intrinsic activity, in chronic idiopathic constipation—a 4-week, randomized, double-blind, placebo-controlled, dose-response study", Alimentary Pharmacology and Therapeutics, 32: 1102-1112 (2010).
Hasler et al., "Bloating in gastroparesis: Severity, impact, and associated factors", Am J Gastroenterol, 106(8): 1492-1502 (Aug. 2011).
Jung et al., "The incidence, prevalence, and outcomes of patients with gastroparesis in Olmstead County, Minnesota, From 1996 to 2006", Gastroenterology, 136(4): 1225-1233 (2009).
Karamanolis et al., "Determinants of symptom pattern in idiopathic severely delayed gastric emptying: gastric emptying rate or proximal stomach dysfunction?", Gut, 56(1): 29-36 (2007).
Long et al., "Discovery, oral pharmacokinetics and in vivo efficacy of velusetrag, a highly selective 5-HT4 receptor agonist that has achieved proof-of-concept in patients with chronic idiopathic constipation", Bioorganic & Medicinal Chemistry Letters, 22: 6048-6052 (2012).

(Continued)

*Primary Examiner* — Jean P Cornet
(74) *Attorney, Agent, or Firm* — Steinfl + Bruno LLP

(57) ABSTRACT

The present invention relates to methods and pharmaceutical compositions for treatment of all symptoms of gastroparesis in a human patient, the method comprising administering to the human patient between about 0.5 mg/day to about 30 mg/day, about 0.5 mg/day to about 15 mg/day, about 0.5 mg/day to about 5 mg/day, or about 5 mg/day, of velusetrag or a pharmaceutically-acceptable salt thereof.

19 Claims, 49 Drawing Sheets

(56) References Cited

OTHER PUBLICATIONS

Manini et al., "Effects of TD-1508 on gastrointestinal transit and bowel function in health and pharmacokinetics in health and constipation", Neurogastroenterol Motil, 22(1): 42-e8 (Jan. 2010).

Matsueda et al., "A placebo-controlled trial of acotiamide for meal-related symptoms of functional dyspepsia", Gut, 61: 821-828 (2012).

Miwa et al., "Efficacy of the 5-HT1A agonist tandospirone citrate in improving symptoms of patients with functional dyspepsia: A randomized controlled trial", The American Journal of Enterology, 104: 2779-2787 (2009).

Parkman et al., "American gastroenterological association technical review on the diagnosis and treatment of gastroparesis", Gastroenterology, 127(5): 1592-1622 (2004).

Parkman et al., "Similarities and differences between diabetic and idiopathic gastroparesis", Clinical Gastroenterology and Hepatology, 9(12): 1056-1064 (2011).

Parkman et al., "Early satiety and postprandial fullness in gastroparesis correlate with gastroparesis severity, gastric emptying, and water load testing: The NIDDK gastroparasis clinical research consortium", Neurogastroenterol Motil, 29(4) (2017).

Patterson et al., "A double-blind multicenter comparison of domperidone and metoclopramide in the treatment of diabetic patients with symptoms of gastroparesis", The American Journal of Gastroenterology, 94(5): 1230-1234 (1999).

Sarnelli et al., "Symptoms associated with impaired gastric emptying of solids and liquids in functional dyspepsia", The American Journal of Gastroenterology, 98(4): 783-788 (2003).

Soykan et al., "Demography, clinical characteristics, psychological and abuse profiles, treatment, and long-term follow-up of patients with gastroparesis", Digestive Diseases and Sciences, 43(11): 2398-2404 (Nov. 1998).

Tack et al., "Functional gastroduodenal disorders", Gastroenterology, 130: 1466-1479 (2006).

Tack et al., "Efficacy of buspiron, a fundus-relaxing drug, in patients with functional dyspepsia", Clinical Gastroenterology and Hepatology, 10: 1239-1245 (2012).

Ardila-Hani A., et al., "Severity of Dyspeptic Cymptoms Correlates". . . , Dig. Dis. Sci., vol. 58, No. 2, pp. 478-487, 2013.

Hasler, W. L., "Gastroparesis: pathogenesis, diagnosis and management", Nat. Rev. Gastroenterology & Hepatology, vol. 8, No. 8 pp. 438-453, 2011.

Jaffe, J.K., et al., "Characteristics of Nausea and Its Effects on Quality of Life in Diabetic and Idiopathic Gastroparesis", J. Clin. Gastroenterol., vol. 45, No. 4, pp. 317-321, 2011.

Kusunoki H., et al, "Therapeutic efficacy of acotiamide in patients with functional". . . , Neurogastroenterol. Motil., vol. 24, No. 6, pp. 540-545, 2012.

Maganti K., et al, "Oral Erythromycin and Symptomatic Relief of Gastroparesis: A Systematic Review", Am. J. Gastroenterology, vol. 98, No. 2, pp. 259-263, 2003.

O'Donovan D., et al., "Idiopathic and Diabetic Gastroparesis", Curr. Treat. Options Gastroenterology, vol. 6, No. 4, pp. 299-309, 2003.

Parkman H. P. and Schwartz S. S., "Esophagitis and Gastroduodenal Disorders". . . , Arch. Intern. Med., vol. 147, No. 8, pp. 1477-1480, 1987.

Parrish C. R., "Nutritional Considerations in Patients". . . , Gastroenterol. Clin. North Am., vol. 44, No. 1, pp. 83-95, 2015.

Stein B., et al, "Gastroparesis", J. Clin. Gastroenterol., vol. 49, No. 7, pp. 550-558, 2015.

Sturm A., et al, "Prokinetics in Patients with Gastroparesis: A Systematic Analysis", Digestion, vol. 60, No. 5, pp. 422-427, 1999.

Younes Z., et al., "The Spectrum of Spontaneous and Iatrogenic Esophageal Injury: Perforations, Mallory-Weiss Tears, and Hematomas", J. Clin. Gastroenterology, vol. 29, No. 4, pp. 306-317, 1999.

Yu D., et al., "The Burdens, Concerns, and Quality of Life of Patients with Gastroparesis", Dig. Dis. Sci., vol. 62, No. 4, pp. 879-893, 2017.

FDA Draft Guidance, :Gastroparesis Clinical Evaluation of Drugs for Treatment, Guidance for Industry, Jul. 2015.

Ahn A., et al., Gastroenterology, vol. 148, No. 4, S-507, 2015.

International Search Report of the International Patent Application No. PCT/US2018/044337, dated Oct. 12, 2018, (4 pages).

Written Opinion on the International Patent Application No. PCT/US2018/044337, dated Oct. 12, 2018 (7 pages).

Abell, T. et al., Efficacy of Velusetrag Treatment in Patients with Idiopathic Gastroparesis: Subgroup Analysis of a Phase 2b Study, Abstract at UEG (United European Gastroenterology) Week 2019, Apr. 26, 2019.

Abell, T. et al., Velusetrag Improves Gastroparesis Both in Symptoms and Gastric Emptying in Patients with Diabetic or Idiopathic Gastroparesis in a 12-Week Global Phase 2B Study. Abstract for oral presentation at DDW (Digestive Disease Week) Meeting, San Diego (CA). May 18, 2019.

Pasricha, J.P. et al., "Toward a Better Drug for Gastroparesis: The Problem With a Moving Target" Gastroenterology, vol. 151, pp. 20-22, 2016.

Bielefeldt K. et al. Different faces of Gastroparesis. World J. Gastroenterol. Dec. 28, 2009; 15(48): 6052-60.

Revicki D.A. et al. Gastroparesis Cardinal Symptom Index (GCSI): development and validation of a patient reported assessment of severity of gastroparesis symptoms. Quality of Life Research. 2004; 13: 833-44.

De Bortoli N. et al. Gastroesophageal reflux disease, functional dyspepsia and irritable bowel syndrome: common overlapping gastrointestinal disorders. Ann Gastroenterol. 2018; 31: 639-648.

Tack J. et al. Systematic Review: Cardiovascular Safety Profile of 5-HT(4) Agonists Developed for Gastrointestinal Disorders. Aliment. Pharmacol. Ther. 2012; 35: 745-767).

Stanghellini V. and Tack J. Gastroparesis: seperate entity or just a part of dyspepsia? Gut. Dec. 2014; 63(12): 1972-8.

Hoogerwerf W. A. et al. Pain: The Overlooked Symptom in Gastroparesis. Am J Gastroenterology. Apr. 1999; 94(4): 1029-33.

Boeckxstaens G.E.E. Review article: the pathophysiology of gastro-oesophageal reflux disease. Alimentary Pharmacology & Therapeutics, 2007, 26, 149-160.

Lightdale J.R. et al. Gastroesophageal Reflux: Management Guidance for the Pediatrician. From The American Academy of Pediatrics, vol. 131, No. 5, May 2013, e1684-e1695.

Mittal R.K. et al. Special Reports and Reviews: Transient Lower Esophageal Sphincter Relaxation. Gastroenterology, 1995, 109; 601-610.

Vakil N. et al. The Montreal Definition and Classification of Gastroesophageal Reflux Disease: A Global Evidence-Based Consensus, American Jouranl of Gastroenterology, 2006: 101; 1990-1920.

Vandenplas Y. et al. Pediatric Gastroesophageal Reflux Clinical Practice Guidelines: Joint Recommendations of the North American Society for Pediatric Gastroenterology, Hepatology, and Nutrition (NASPGHAN) and the European Society for Pediatric Gastroenterology, Hepatology, and Nutrition (ESPGHAN). Journal of Pediatric Gastroenterology and Nutrition, 2009, 49: 498-547.

Zerbib F. et al. Normal values and day-to-day variability of 24-h ambulatory oesophageal impedence-pH monitoring in a Belian-French cohort of healthy subjects. Aliment Pharmacol Ther, 2005, 22: 1011-1021.

The Voice of the Patient. (A series of report from the U.S. Food and Drug Administration's (FDA's) Patient-Focused Drug Development Initiative). Functional Gastrointestinal Disorders. Report Date: Jan. 2016. Center for Drug Evaluation and Research (CDER); U.S. Food and Drug Administration (FDA). 22 pages.

Parkman H.P. et al. Gastroparesis and Functional Dyspepsia: Excerpts from the AGA/ANMS Meeting. Neurogastroenterol Motil., Feb. 2010;22(2): 113-133. Doi:10.1111/j.1365-2982.2009.01434.x. 32 pages.

Li He-Fei et al. Expression of Serotonin Receptors in Human Lower Esophageal Sphincter. Experimental and Therapeutic Medicine, 9, 49-54, 2015.

Tack J. et al. Functional Gastroduodenal Disorders. Gastroenterology, 2006, 130:1466-1479.

(56) References Cited

OTHER PUBLICATIONS

Fass R. et al. Review article: supra-oesophageal manifestations of gastro-oesophageal reflux disease and the role of night-time gastro-oesophageal reflux. Aliment Pharmacol Ther. 2004;20 Suppl 9:26-38.

Ahn, A. et al., Su.1426. "Velusetrag Improves Gastric Emptying Time in Subjects with Diabetic or Idiopathic Gastroparesis". Gastroenterology, 2015, 148; S-507. 1 page.

Camilleri, M. et al. "Clinical guideline: management of gastroparesis". American College of Gastroenterology, 2013; 108(1): 18-38. 48 pages. Doi: 10.1038/ajg.2012373.

Drossman, D.A. "Section I: FGIDs: Background Information. Functional Gastrointestinal Disorders: History, Pathophysiology, Clinical Features and Rome IV". Gastroenterology, 2016; 150: 1262-1279. 20 pages.

Enck, P. et al. "Irritable bowel syndrome". Nat Rev Dis Primers, 2016; 2: 16014. 60 pages. Doi: 10.1038/nrdp.2016.14.

Ford, A.C. et al. "ACG Task Force on Management of Irritable Bowel Syndrome. American College of Gastroenterology Monograph on Management of Irritable Bowel Syndrome". Am J Gastroenterol. Jun. 2018; vol. 113 (Suppl 2):1-18.

Nassar, Y. et al. "Gastroparesis in Non-Diabetics: Associated Conditions and Possible Risk Factors". Gastroenterology Res. 2018; 11(5): 340-345.

National Institutes of Health: "Glossary of Common Site Terms" NIH Clinical Trial Glossary, dated Jul. 30, 2017. 18 pages. Downloaded on Sep. 3, 2022 through the Wayback Machine.

Pasricha, P.J. et al. "Toward a Better Drug for Gastroparesis: The Problem With a Moving Target". Gastroenterology 2016: 151: 20-22. 3 pages.

Sanders, K.M. et al. "Interstitial cells: regulators of smooth muscle function". Physiol Rev. 2014; 94: 859-907. Doi: 101152/physrev.00037.2013.

Stranghellini, V, et al. "Dyspeptic symptoms and gastric emptying in the irritable bowel syndrome". Am J Gastroenterol. Nov. 2002; vol. 97, No. 11: 2738-2743.

\* cited by examiner

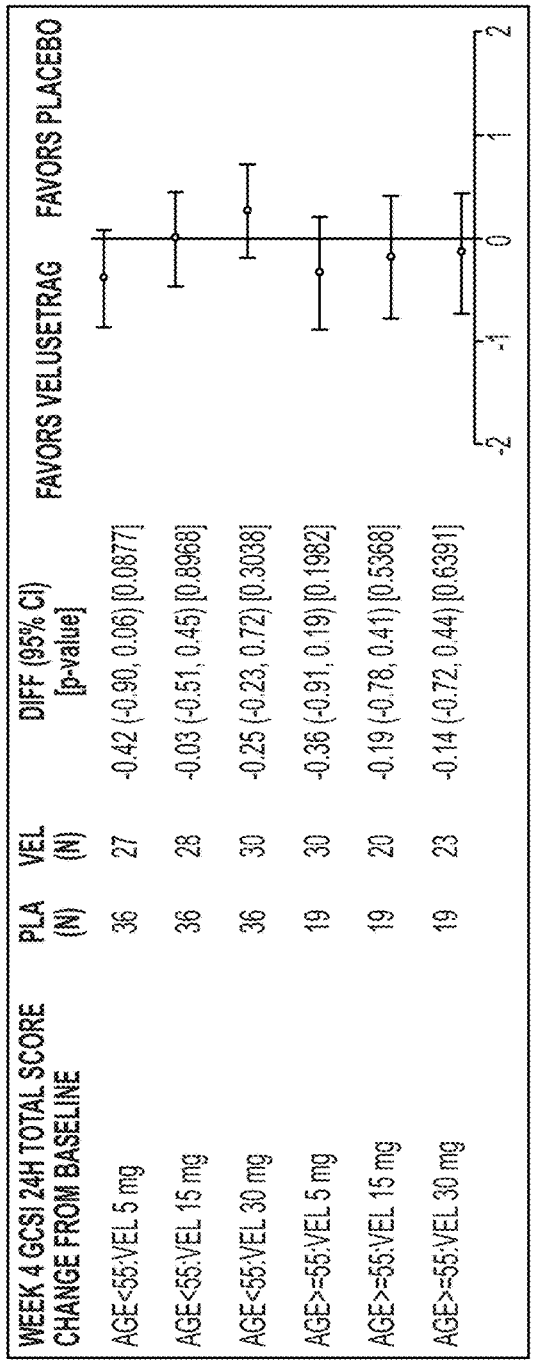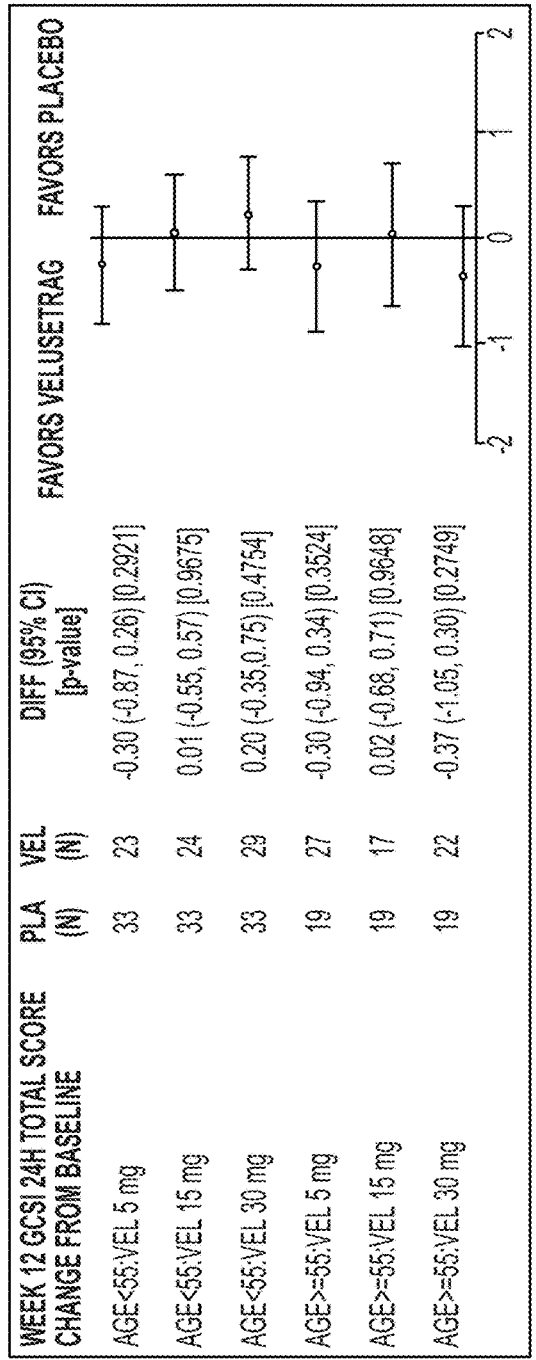
FIG. 4A
FIG. 4B

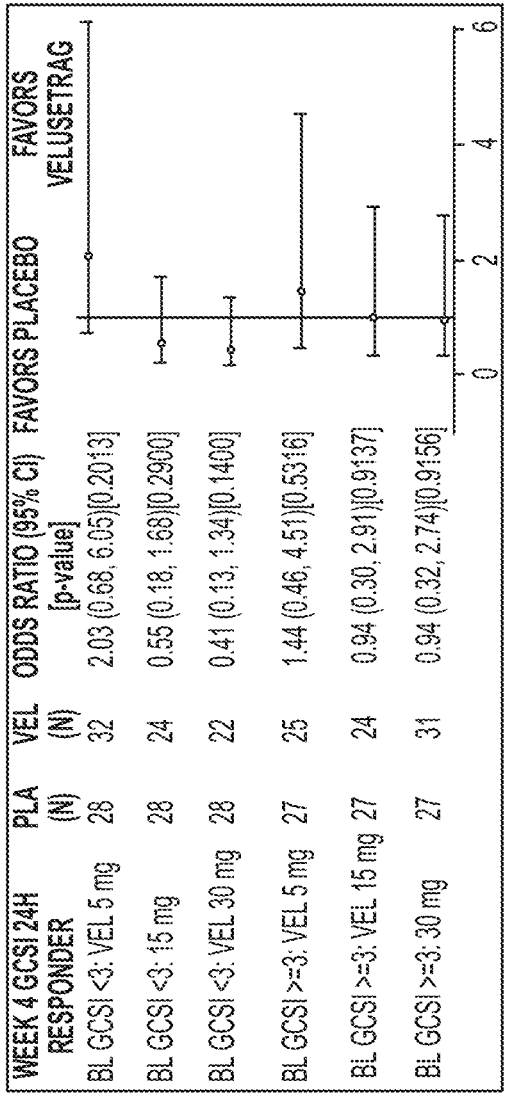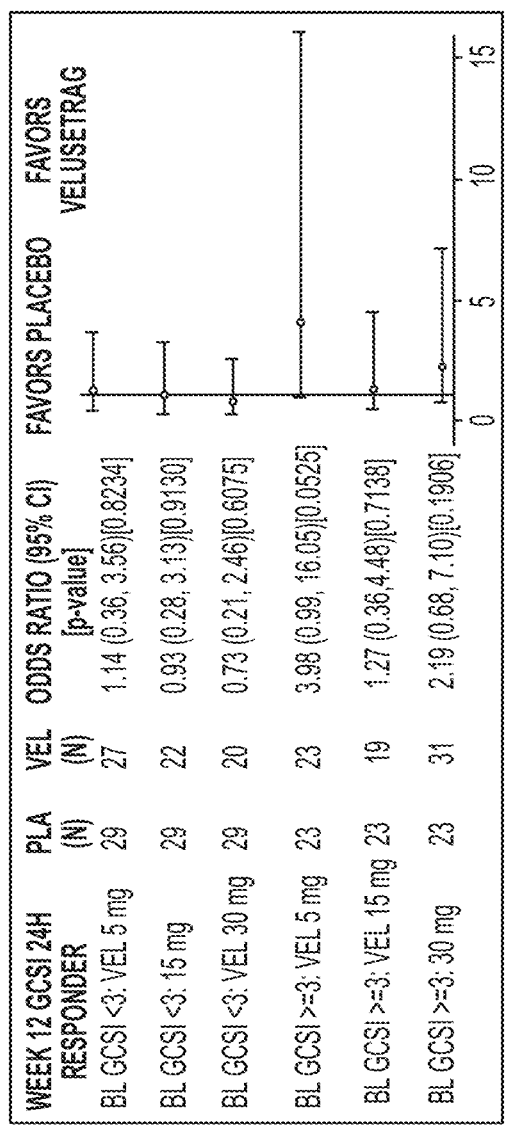

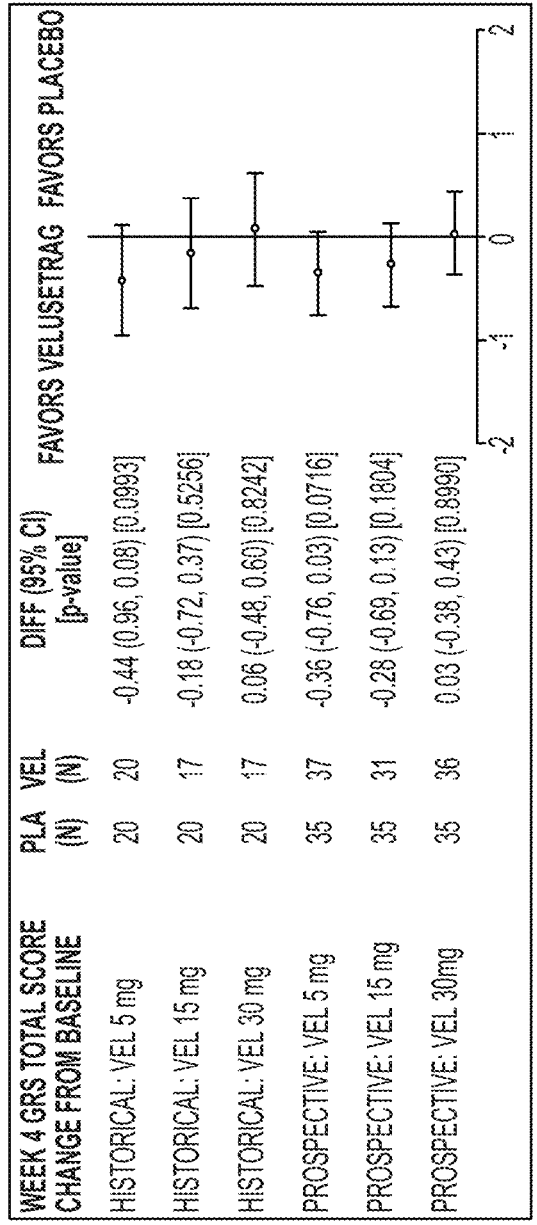
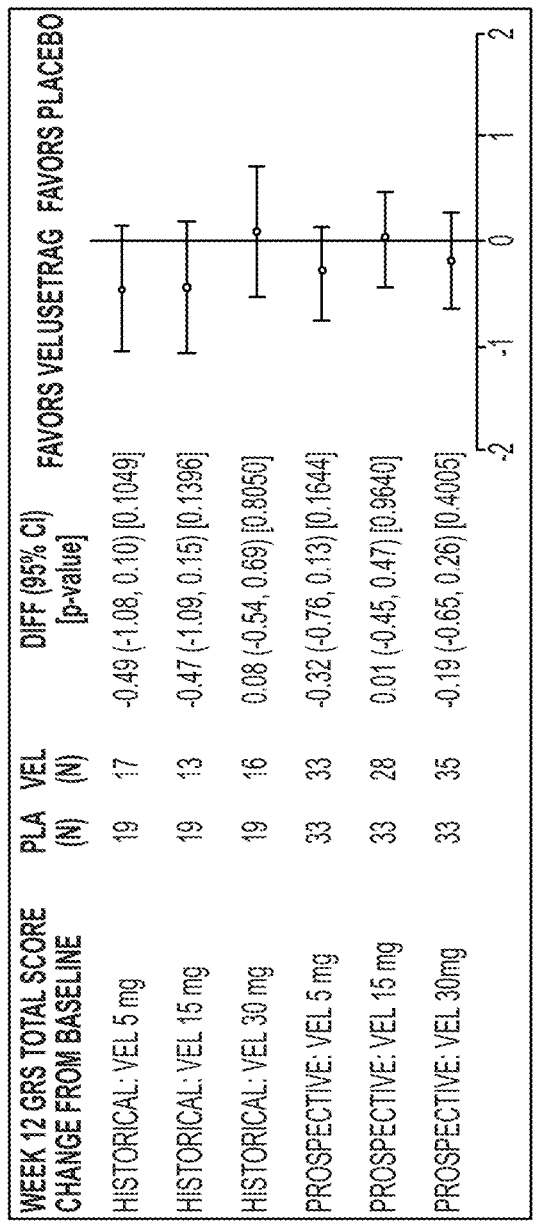
FIG. 21A
FIG. 21B

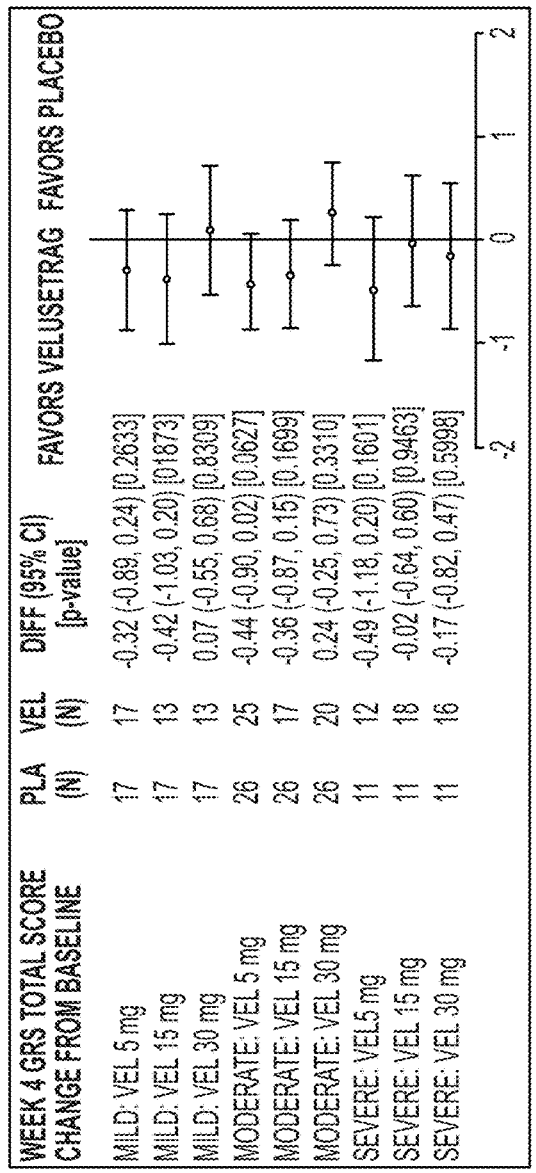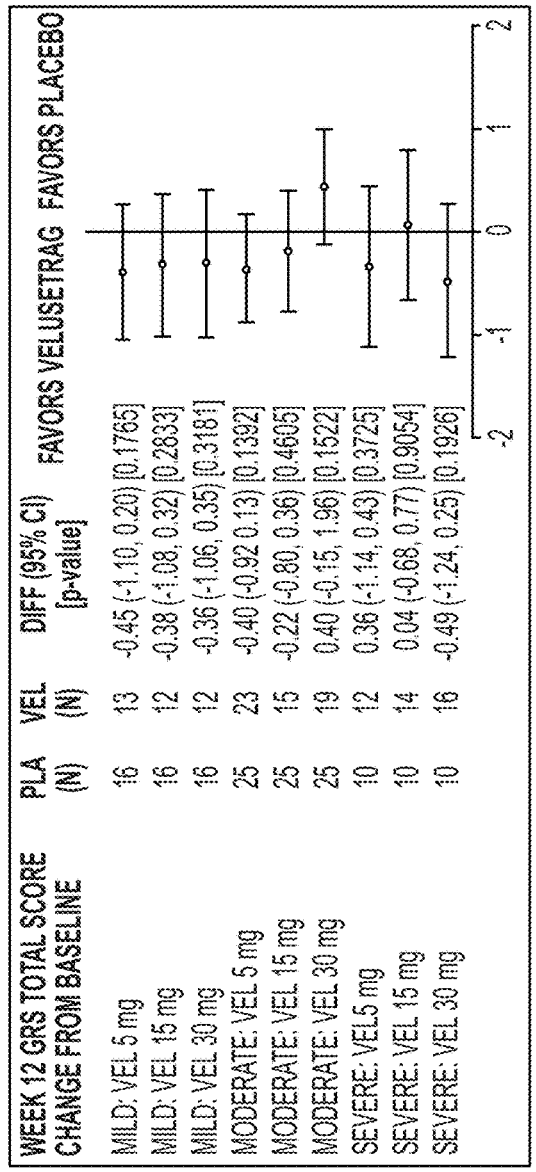
FIG. 23A
FIG. 23B

METHODS OF TREATING SYMPTOMS OF GASTROPARESIS USING VELUSETRAG

CROSS-REFERENCE TO RELATED APPLICATION

This application claims the benefit of U.S. Provisional Application No. 62/539,229, filed on Jul. 31, 2017, the disclosure of which is incorporated herein by reference in its entirety.

THE NAMES OF THE PARTIES TO A JOINT RESEARCH AGREEMENT

The invention claimed herein was made by, or on behalf of, and/or in connection with the following parties to a joint research agreement: Theravance Biopharma Ireland Limited and Alfasigma S.p.A. The agreement was in effect on and before the date the claimed invention was made, and the claimed invention was made as a result of activities undertaken within the scope of the agreement.

BACKGROUND OF THE INVENTION

Field of the Invention

The present invention relates to velusetrag (1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide) and pharmaceutical compositions comprising thereof for treating and/or use in the treatment of symptoms associated with idiopathic or diabetic gastroparesis in a human patient by administering velusetrag or a pharmaceutically-acceptable salt thereof between about 0.5 mg/day and about 30 mg/day, to the human patient.

State of the Art

Alterations in the basic digestive functions occurring at the gastroduodenal region of the upper gastrointestinal tract are a very common condition affecting a large number of people. Disorders of various nature of the gastrointestinal tract impair one or more of its functions. Structural and neural abnormalities can slow, obstruct, or accelerate the movement of intestinal content at any level of the gastrointestinal tract. Inflammatory and ulcerative conditions of the gastrointestinal wall disrupt secretion, motility, and absorption. Inflammation or obstruction of the liver, pancreas, or gallbladder can alter metabolism and result in local or systemic symptoms, or both. Many clinical manifestations of gastrointestinal tract disorders are nonspecific and can be caused by a variety of impairments. At least 20% of the population has chronic symptoms that can be attributed to disorders of gastroduodenal function, the condition significantly impacts on the usual activities of the patient and is characterized by one or more of the following symptoms: nausea, bloating, postprandial fullness, early satiety, vomiting, upper abdominal pain, epigastric burning, gastric reflux with or without burning, and disordered gastrointestinal motility. Symptoms may be chronic, occurring at least weekly and over a period of at least 6 months, in the absence of an organic explanation (Tack, J., et al. *Gastroenterology.* 2006; 130; 1466-1479).

A similar set of clinical manifestations present in patients affected by gastroparesis, which is a common, yet serious, chronic sensorimotor disorder of the upper gastrointestinal tract, is defined by the presence of delayed gastric emptying (GE) in the absence of mechanical obstruction and is associated with significant symptomatology (e.g., nausea, vomiting, early satiation, bloating, and abdominal pain) that can profoundly impair quality of life (QOL) (Parkman, H. P. et al., *Gastroenterology,* 2004, 127(5), 1592-1622; Stein, B. et al, *J Clin. Gastroenterol.,* 2015, 49(7); Parkman, et al., *Clin. Gastroenterol. Hepatol.,* 2011, 9(12), 1056-1064).

The etiology of gastroparesis is diverse, although often associated with diabetes mellitus (Stein, B. et al, *J. Clin. Gastroenterol.,* 2015, 49(7); Bharucha, A. E., *Gastroenterol. Clin. North Am.,* 2015, 44(1), 9-19). However, the underlying cause cannot be identified in nearly 50% of patients, e.g., idiopathic disease.

In gastroparesis as well as in other upper gastrointestinal tract diseases symptoms definitions remain somewhat vague, and potentially difficult to be understood and interpreted by patients, physicians and investigators, thereby delaying the arrival to the positive therapeutic outcome. The pathophysiologic mechanisms basing these symptoms are complex and multifactorial. The gastroparesis symptomatology largely overlaps with that of upper gastrointestinal tract diseases with associated GE delay. More than one in four patients with upper gastrointestinal tract impairment have evidence of delayed gastric emptying (Sarnelli G. et al. *Am J Gastroenterol* 2003; 98: 783-788) and in one study 86% of the patients with gastroparesis show the symptoms suggestive of gastroduodenal involvement: nausea, bloating, postprandial fullness, early satiation, vomiting, upper abdominal pain, epigastric burning, gastric reflux with or without burning, and bowel movements, revelatory of possible similar pathophysiological features for these conditions.

Currently, the only FDA-approved drug for diabetic gastroparesis is metoclopramide, a dopamine $D_2$ receptor antagonist and $5-HT_3$ receptor antagonist with weak $5-HT_4$ agonist activity, which is indicated for the relief of symptoms associated with acute and recurrent diabetic gastric stasis for no longer than 12 weeks of treatment. Metoclopramide has been found to be equally as effective in the short-term control of symptoms of diabetic gastroparesis when compared with domperidone; however, CNS side effects are significantly more common and generally of greater severity with metoclopramide (Patterson, D., et al., *Am. J. Gastroenterol.,* 1999, 94(5), 1230-1234). The effects of metoclopramide rapidly diminish over time and long-term use is limited by relatively common adverse CNS effects (reported in up to 30% of patients on daily therapy), including sedation and restlessness as well as less frequent extrapyramidal effects, most commonly acute dystonia. Therefore, metoclopramide is not recommended routinely because of its uncertain efficacy and side effects (including irreversible tardive dyskinesia).

Acotiamide is an acetylcholinesterase inhibitor accelerating gastric emptying and enhancing gastric accommodation (Kusunoki H. et al. *Neurogastroenterol Motil* 2012; 24: 540-545). In a double-blind, placebo-controlled trial involving patients with functional dyspepsia in Japan, symptoms improved in 52% of those assigned to active therapy, as compared with 35% of those assigned to placebo (Matsueda K. et al. *Gut* 2012; 61: 821-828); significant improvements were identified in postprandial fullness, upper abdominal bloating and early satiety, but not in upper abdominal pain or discomfort. Drugs such as buspirone and tandospirone, acting on the 5-hydroxytryptamine-1A receptor and leading to relaxation of the gastric fundus, have also been tested in functional dyspepsia: buspirone demonstrated to be effective in relaxing the gastric fundus and reduced bloating and postprandial fullness in 17 patients with functional dyspepsia enrolled in a randomized crossover trial (Tack J. et al. *Clin Gastroenterol Hepatol* 2012; 10: 1239-1245). In a double-blind, placebo-controlled study involving 144 patients, the response rate after 4 weeks of treatment with tandospirone was 31.5%, as compared with 12.7% with placebo (Miwa H. et al. *Am J Gastroenterol* 2009; 104: 2779-2787).

Erythromycin is a macrolide antibiotic and motilin receptor activator that has been shown to improve gastric emptying; however, clinical data regarding efficacy in gastroparesis symptom management are inconsistent (Camilleri, M., et al., *Am. J Gastroenterol.*, 2013, 108(1), 18-37; Maganti, K., et al., *Am. J. Gastroenterol.*, 2003, 98(2), 259-263; Sturm, A., et al., *Digestion*, 1999, 60(5), 422-427). Similar to metoclopramide, effectiveness is limited by rapid development of tachyphylaxis. Erythromycin prolongs the QT interval and has been associated with cardiac arrhythmias (including torsade's de pointes), particularly in patients with coexisting risk factors (e.g., female gender, congestive heart failure, cardiomyopathies, long QT syndrome). Other adverse effects associated with erythromycin include hypotension and *C. difficile* colitis. In addition, the development of antibiotic resistance is possible.

Domperidone is a $D_2$ receptor antagonist, similar to metoclopramide, but generally associated with a lower risk of serious adverse effects. Domperidone has demonstrated similar efficacy to metoclopramide; however, it is not FDA approved for any indication and is available only through an Expanded Access to Investigational Drugs program for patients where the benefit likely outweighs potential risks. The expanded access program requires prescribing physicians to obtain an IND and IRB approval, which further limits access of domperidone. Domperidone is associated with an increased risk for adverse cardiovascular effects including cardiac arrest and sudden death primarily due to prolongation of the QT interval; the incidence of these events is low (Camilleri, M., et al., *Am. J. Gastroenterol.*, 2013, 108(1), 18-37).

Furthermore, not only the described individual symptoms are frequent in the general population, but a considerable overlap exists among digestive symptoms in more than one third of the patients, with clustering of symptoms likely associated by common or similar pathophysiological mechanisms, especially in the most severe cases. Factor analysis revealed at least three clusters with a cluster including fullness, bloating and early satiation, a second cluster including nausea and vomiting, and a third cluster including discomfort, pain, belching and reflux.

Despite extensive research, pharmacologic treatment options remain limited and are often associated with serious side effects. With regard to the treatment of gastroparesis, a recent, large community survey showed only 19% of respondents rated their satisfaction with available treatment, including both pharmacologic and non-pharmacologic options, as somewhat satisfied (15%) to satisfied (4%) with 60% rating their satisfaction as somewhat dissatisfied to dissatisfied (Yu, D., et al., *Dig. Dis. Sci.*, 2017, 62(4), 879-893).

To date, there exists a strong unmet medical need for a treatment/medicament for gastroparetic patients with main symptoms correlated to the upper gastrointestinal tract such as: nausea, bloating, postprandial fullness, early satiation, vomiting, upper abdominal pain, epigastric burning, and gastrointestinal motility, and their various combinations in symptoms cluster, which may be present in chronic idiopathic gastroparesis. The problem is particularly difficult to solve because of the remarkable variability and the overlap level of the symptoms which often account for misleading diagnosis. There is also a need for a treatment/medicament suitable to effectively treat all symptoms of gastroparesis, in particular, idiopathic and/or diabetic gastroparesis. There is also a need to find a medicine able to treat, reduce, ameliorate, and/or alleviate symptoms associated with gastroparesis without providing gastric emptying or with providing a normalization of gastric emptying.

Velusetrag is a novel potent, pan-GI, potent, highly selective 5-hydroxytryptamine subtype 4 (5-HT$_4$) receptor agonist with prokinetic activity that was developed in part for the treatment of gastroparesis. The chemical name of velusetrag is 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and its chemical structure is shown below in Formula I:

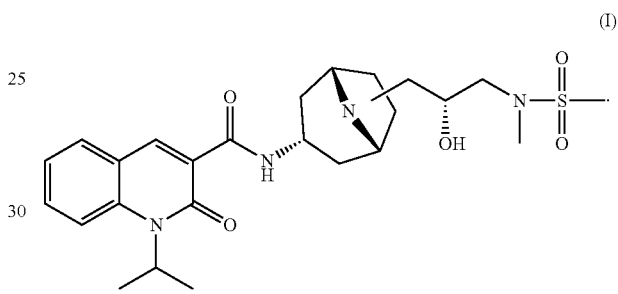

(I)

Velusetrag was previously disclosed in commonly-assigned U.S. Provisional Application No. 60/560,076, filed on Apr. 7, 2004, and U.S. patent application Ser. No. 11/100,113, filed on Apr. 6, 2005; and crystalline form in U.S. Provisional Application No. 60/668,780, filed Apr. 6, 2005, and U.S. patent application Ser. No. 11/398,119, filed Apr. 5, 2016, corresponding to EP 1 735 304. All of the patents, patent applications, and documents cited herein are each hereby incorporated by reference in their entireties.

Velusetrag is currently being tested in the clinical setting as the hydrochloride salt for the treatment of gastroparesis. Based on the unmet medical need and supported by the data on improvement in gastric emptying with velusetrag treatment, a development program was initiated in diabetic and idiopathic gastroparesis evaluating the effect of velusetrag (5 mg, 15 mg, and 30 mg) on the symptoms of gastroparesis and assessing gastric emptying using gastric emptying scintigraphy. An a priori statistical analysis for the primary endpoint, i.e., a placebo-adjusted change from baseline in a patient-reported symptom score after four weeks of dosing, had assumed that the data would support a dose-dependent improvement in symptom score going from about 0.5 mg to about 30 mg.

SUMMARY OF THE INVENTION

Surprisingly, it has now been found that when velusetrag is used to treat gastroparesis in diabetic or idiopathic adult patients, symptom relief as reported by the patient is not correlated with increased motility. It was expected that patient symptoms would improve with maximal gastric emptying based on an earlier Phase 2a study but instead and unexpectedly, patients report greater symptom relief at a dose of about 5 mg/day, or lower, compared to higher doses that provide greater gastric emptying, such as the 15 mg/day or 30 mg/day, or higher doses. Until now, it was not appreciated that an inverse relationship existed between a lower dose and patient-reported symptoms. Thus, the invention generally relates to finding the right balance between amount of gastric emptying and patient reported symptoms to effectively treat gastroparetic patients.

The invention is directed to methods of preventing, alleviating, ameliorating, giving relief to, and/or treating symptoms associated with gastroparesis in a human patient by administering velusetrag, or a pharmaceutically-acceptable salt thereof, between about 0.5 mg/day and about 30 mg/day, between about 0.5 mg/day and about 15 mg/day, between about 0.5 mg/day and about 5 mg/day, or about 5 mg/day, with or without food. The invention is also directed to the corresponding compositions for use in said methods. According to the present invention, the methods of preventing, alleviating, ameliorating, giving relief to, and/or treating symptoms associated with gastroparesis is based on the administration of velusetrag at about 0.5, 1.0, 1.5, 2.0, 2.5, 3.0, 3.5, 4.0, 4.5, 5.0, 10, 15, 20, 25, or 30 mg/day or higher. According to the present invention, improvement in all symptoms and in particular all core symptoms of gastroparesis (fullness/early satiety, bloating, upper abdominal pain, epigastric burning, nausea, vomiting) is achieved.

In one embodiment, the invention relates to a method of treating, preventing, alleviating, and/or ameliorating gastroparesis symptoms in diabetic patients.

In another embodiment, the invention relates to a method of treating, preventing, alleviating, and/or ameliorating gastroparesis symptoms in idiopathic patients.

In one embodiment, the patient may have diabetic or idiopathic gastroparesis and in another embodiment, the administration of velusetrag in the diabetic gastroparesis patient results in little to no increase in hyperglycemia and/or glucose. In another embodiment, the pharmaceutically-acceptable salt is a hydrochloride salt. In yet another embodiment, velusetrag is in a crystalline form as described in U.S. Pat. No. 7,728,004.

In one embodiment, the invention relates to methods of treating, preventing, alleviating, ameliorating, giving relief to, and/or treating symptoms of gastroparesis comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, or about 5 mg/day.

In another embodiment, the invention relates to methods of treating, preventing, alleviating, and/or ameliorating symptoms selected between nausea and vomiting comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, or about 5 mg/day.

In a further embodiment, the invention relates to methods of preventing, alleviating, ameliorating, giving relief to, and/or treating symptoms selected between postprandial fullness and early satiety comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, or about 5 mg/day.

In another embodiment presented herein are methods of preventing, alleviating, ameliorating, giving relief to, and/or treating upper abdominal pain comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, about 5 mg/day.

A further embodiment relates to methods of preventing, alleviating, ameliorating, giving relief to, and/or treating epigastric burning comprising administering a therapeutically amount of velusetrag to a subject with delayed gastric emptying, in an amount from about 0.5 mg/day to about 30 mg/day, from about 0.5 mg/day up to about 15 mg/day, from about 0.5 mg/day to about 5 mg/day, or about 5 mg/day.

In one embodiment presented herein are methods of preventing, alleviating, ameliorating, giving relief to, and/or treating bowel movements comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, or about 5 mg/day.

In another embodiment presented herein are methods of preventing and/or alleviating and/or ameliorating, and/or treating nausea and/or vomiting, and/or postprandial fullness, and/or early satiety, and/or bloating, upper abdominal pain, and/or epigastric burning and/or bowel movements, or their combination, comprising administering a therapeutically amount of velusetrag to a subject with delayed gastric emptying, in an amount from about 0.5 mg/day to about 30 mg/day, from about 0.5 mg/day to about 15 mg/day, from about 0.5 mg/day to about 5 mg/day, or about 5 mg/day.

In yet another embodiment is a method for obtaining a reverse dose response during the administration time of velusetrag, at daily dosage of 5 mg or lower.

In one embodiment, the invention relates to a method for preventing, and/or alleviating, and/or ameliorating, and/or reducing, and/or treating in a patient gastrointestinal symptoms wherein tachyphylaxis or diminution of effects occurs during the treatment.

Another embodiment relates to methods wherein symptom changes with velusetrag administration from about 0.5 to about 30 mg/day represent a reduction greater than 0.5 to 1.5 point change in level of symptom severity, from severe symptoms to moderate symptoms, from moderate to mild symptoms.

In another embodiment, the invention relates to methods for preventing, alleviating, ameliorating, giving relief to, and/or treating wherein velusetrag will be administered in an amount from 0.5 to 30 mg/day for as long as necessary, for example, for 1 week, 4 weeks, 8 weeks, 12 weeks or longer. In yet another embodiment, the previous method will be administered in an amount from 0.5 mg/day up to 15 mg/day, more preferably in an amount from 0.5 mg/day to 5 mg/day, and most preferably in an amount of about 5 mg/day.

A further embodiment includes a method for preventing, and/or alleviating, and/or ameliorating, and/or treating, and/or reducing, and/or giving adequate relief to, one or more of the symptoms correlated with gastroparesis effectively.

An additional embodiment includes an adequate relief of gastroparesis symptoms comprising a reduction of one or more of the symptoms selected from: nausea, vomiting, postprandial fullness, early satiety, bloating, upper abdominal pain, epigastric burning, and bowel movements. The reduction of the symptom is identified by a reduction from the symptom's baseline value. In one embodiment, symptoms baseline is established prior to treatment.

In one embodiment, adequate relief of gastroparesis symptoms comprises a 'yes' response from a subject asked the question and by the compilation of a questionnaire.

According to one aspect, provided herein are methods of improving quality of life (QOL) measures in subject with gastroparesis symptoms.

According to one aspect, provided herein are methods of improving QOL measures in subject with gastroparesis symptoms comprising administering velusetrag.

According to another aspect, the invention provides methods of improving QOL measures in subject with gastroparesis symptoms comprising administering velusetrag in a daily dosage from about 0.5 mg/day to about 30 mg/day for a period of 1 week, 2 weeks, 4 weeks, 8 weeks, 12 weeks, 14 weeks or longer. In yet another embodiment, this method will be administered in an amount from about 0.5 mg/day to about 15 mg/day, from about 0.5 mg/day to about 5 mg/day, or about 5 mg/day.

In one embodiment, one or more QOL measures comprising symptoms selected from: nausea, vomiting, postprandial fullness, early satiety, bloating, upper abdominal pain, epigastric burning, bowel movements, dysphoria, body image, health worry, social reaction, and relationship, are improved upon administration of velusetrag.

In another embodiment, pharmaceutical compositions for use in the treatment of gastroparesis are provided. In yet another embodiment the pharmaceutical compositions are a solid blend consisting essentially of drug substance (velusetrag HCl), hydroxypropyl methylcellulose, microcrystalline cellulose, lactose monohydrate, and magnesium stearate.

A further embodiment relates to a controlled release pharmaceutical composition comprising an effective amount of velusetrag.

In yet another embodiment, the invention relates to a method for reducing, preventing, alleviating, ameliorating, giving relief to, and/or treating symptoms selected from: nausea vomiting, postprandial fullness, early satiety, bloating, upper abdominal pain, burning, bowel movements, in male or female in need thereof.

In another embodiment, the invention relates to a method of reducing, preventing, alleviating, ameliorating, giving relief to, and/or treating symptoms associated with gastroparesis in idiopathic and diabetic subjects about 50 years old or greater than 55 years of age or older.

The invention also relates to a method for reducing, preventing, ameliorating, alleviating, giving relief to, and/or treating the symptoms of gastroparesis in a subject suffering by the symptoms for about 1 week to 1 years, before the treatment with velusetrag.

In another embodiment of the invention, pharmaceutical compositions with different routes of administration of velusetrag to the human patient are encompasses. The routes of administration comprise, inter alia, oral, parenteral, buccal, sublingual, rectal, intraperitoneal, or endotracheal routes of administration. For example, parenteral administration may be by infusion, injection, or implantation. Parenteral may also include percutaneous administration via subcutaneous, intramuscular, intravenous, transdermal, or by implantation routes. If velusetrag is administered parenterally, it may be in the form of a liquid, solid or gel. Similarly, if velusetrag is administered orally, it may be in the form of a liquid, capsule, tablet, chewable tablet or dissolvable film.

In one embodiment, the invention provides a kit comprising using and dosing instructions on a package insert of a pharmaceutical product comprising velusetrag according to the invention. In another embodiment, the package insert instructs the patient to administer velusetrag for a period of 1 weeks, 2 weeks, 4 weeks, 8 weeks, 12 weeks or longer.

In one embodiment, the product comprises velusetrag in an amount from about 0.5 mg to about 30 mg labeled for treatment of symptoms of gastroparesis. In yet another embodiment, the product comprises velusetrag in an amount from about 0.5 mg to about 15 mg, from about 0.5 mg to about 5 mg, or about 5 mg labeled for treatment of symptoms of gastroparesis.

In another embodiment, the product comprises velusetrag in an amount from about 0.5 mg to about 30 mg, about 0.5 mg to about 15 mg, about 0.5 mg to about 5 mg, or about 5 mg, labeled for treatment of symptoms of gastroparesis in subject with diabetic or idiopathic gastroparesis.

In one embodiment, the invention provided methods of preventing, alleviating, ameliorating, reducing, giving relief to, and/or treating nausea, vomiting, postprandial fullness, early satiety, bloating, upper abdominal pain, epigastric burning, bowel movements, by administering to a subject in need thereof, a daily dosage of velusetrag from 0.5 to 30 mg/day, 0.5 mg/day to 15 mg/day, 0.5 mg/day to 5 mg/day, or about 5 mg/day.

In yet another embodiment, the invention provides methods for preventing, reducing, ameliorating, alleviating, giving relief to, and/or treating, symptoms of gastroparesis in a subject wherein said symptoms are occurring for at least 1 week before the treatment of velusetrag from 0.5 to 30 mg/day, 0.5 mg/day to 15 mg/day, 0.5 mg/day to 5 mg/day, or about 5 mg/day.

The invention also provides a reverse dose response in the majority of symptoms domains for the GCSI-24H when administering velusetrag at daily dosage from about 0.5 mg to about 30 mg. In another embodiment, invention provides a method for preventing, alleviating, ameliorating, reducing, giving relief to, and/or treating one or more gastroparesis symptoms, wherein a reverse dose response in the majority of symptoms domains is achieved.

In another embodiment, the invention relates to a method for preventing, alleviating, ameliorating, reducing, giving relief to, and/or treating one or more gastroparesis symptoms, wherein the reduction of symptoms in GCSI-24H Total Score is at least 0.4 or higher, compared to placebo during the velusetrag treatment in a daily dosage from about 0.5 mg to about 30 mg.

Another embodiment includes a method for preventing, alleviating, ameliorating, reducing, giving relief to, and/or treating one or more gastroparesis symptoms, wherein the reduction of symptoms in the Week 4, GCSI-24H total Score is at least 0.4 or higher, compared to placebo.

In yet another embodiment, the invention provides a method for preventing, alleviating, ameliorating, reducing, giving relief to, and/or treating gastroparesis symptoms, wherein the reduction of symptoms from baseline and from placebo in the 7 day mean GCSI-24H composite score at Week 4 is provided.

Similarly, the invention also provides a method for preventing, alleviating, ameliorating, reducing, giving relief to, and/or treating gastroparesis symptoms, wherein a reduction of symptoms from baseline in daily and 7-day mean composite GCSI-24 H score over Week 1 through 3 and Weeks 5 through 12 of treatment is provided.

The invention also provides a method for preventing, alleviating, ameliorating, reducing, giving relief to, and/or treating gastroparesis symptoms, wherein a reduction of symptoms from baseline in daily and 7-day mean composite GCSI-24 H individual component scores of the symptoms over Week 1 through 12 of treatment is provided.

In one embodiment, the invention provides a method for preventing, alleviating, ameliorating, reducing, giving relief to, and/or treating gastroparesis symptoms, wherein there is a higher reduction of symptoms from baseline in daily and 7-day mean composite GCSI-24 H score in idiopathic patients compared to diabetic patients with higher efficacy with velusetrag at daily dosages from about 0.5 mg/day to about 30 mg/day, about 0.5 mg/day to about 15 mg/day, about 0.5 mg/day to about 5 mg/day or about 5 mg/day.

In another embodiment, the invention provides a higher reduction of symptoms from baseline in daily and 7-day mean composite GCSI-24H score in idiopathic patients compared to diabetic patients with higher efficacy at more than 4 weeks.

In another embodiment, the invention provides a method for preventing, alleviating, ameliorating, reducing, giving relief to, and/or treating gastroparesis symptoms, wherein the reduction of symptoms of baseline from placebo GCSI-24H at Week 4 is about 0.2 with velusetrag at 5 mg/day in diabetic patients.

In yet another embodiment, the invention provides a method for preventing, alleviating, ameliorating, reducing, giving relief to, and/or treating gastroparesis symptoms, wherein the reduction of baseline from placebo GCSI-24H at Week 8 is about 0.1 with velusetrag at 5 mg/day in diabetic patients.

In one embodiment, a method for preventing, alleviating, ameliorating, reducing, giving relief to, and/or treating gastroparesis symptoms is provided, wherein the reduction of baseline from placebo GCSI-24H is maintained over Week 8 along the treatment time with velusetrag 5 mg/day in diabetic patients.

In another embodiment, a method for preventing, alleviating, ameliorating, reducing, giving relief to, and/or treating gastroparesis symptoms is provided, wherein the reduction of baseline from placebo GCSI-24H at Week 14 is about 0.1 with velusetrag 30 mg/day in diabetic patients.

Another embodiment relates to a method for preventing, alleviating, ameliorating, reducing, giving relief to, and/or treating gastroparesis symptoms, wherein change from baseline GCSI-24 H score in idiopathic patients is about 0.4 with velusetrag at daily dosage from about 0.5 mg to about 30 mg along the treatment time.

One embodiment relates to a method for preventing, alleviating, ameliorating, reducing, giving relief to, and/or treating to gastroparesis symptoms, wherein the reduction of symptoms from baseline GCSI-24H score in idiopathic patients at Week 4 is about 0.6 points with velusetrag at daily dosage of 5 mg.

In another embodiment, the invention relates to a method for preventing, alleviating, ameliorating, reducing, giving relief to, and/or treating gastroparesis symptoms, wherein the reduction of symptoms from baseline GCSI-24H score in idiopathic patients at Week 8 is about 0.6 points with velusetrag at daily dosage of 5 mg.

One embodiment relates to a method for preventing, alleviating, ameliorating, reducing, giving relief to, and/or treating gastroparesis symptoms, wherein the reduction of symptoms from baseline GCSI-24H score in idiopathic patients at Week 12 is about 0.6 points with velusetrag at daily dosage of 5 mg.

Another embodiment relates to a method for preventing, alleviating, ameliorating, reducing, giving relief to, and/or treating gastroparesis symptoms, wherein the reduction of symptoms from baseline GCSI-24H score in idiopathic patients is maintained along the treatment time with velusetrag at daily dosage of 5 mg.

In one embodiment, a method for preventing, alleviating, ameliorating, reducing, giving relief to, and/or treating gastroparesis symptoms is provided, wherein the reduction of symptoms from baseline GCSI-24H score in idiopathic patients at Week 4 is about 0.3 with velusetrag at daily dosage of 15 mg and this change is maintained along the treatment time.

In one embodiment, the invention provides a reduction of symptoms from baseline of about 0.3 points at Week 8 in idiopathic patients compared to diabetic patients with velusetrag 15 mg daily dosage. In another embodiment, the invention provides a change from baseline of about 0.2 points at Week 12 in idiopathic patients compared to diabetic patients with velusetrag 15 mg daily dosage.

In yet another embodiment, the invention provides a reduction of symptoms from baseline of about 0.1 points at Week 14 in idiopathic patients compared to diabetic patients with velusetrag 15 mg daily dosage.

One embodiment includes a method to provide at least 1-point improvement from baseline in the GCSI-24 H individual components at each Week (1-12) score over Week 1 through 3 and Weeks 5 through 12 and along all the velusetrag treatment from about 0.5 mg/day to about 5 mg/day.

Another embodiment includes a method to provide a statistically significant difference, or reduction, or improvement in the week 4 GCSI-24H total score and along all the treatment time by administration of about 5 mg velusetrag or lower.

In another embodiment, the invention provides a method for preventing, alleviating, ameliorating, reducing, giving relief to, and/or treating gastroparesis symptoms, wherein a proportion of subject with at least 1-point improvement from baseline in the GCSI-24 H individual components at each week (1-12) score over week 1 through 3 and Weeks 5 through 12 of treatment. In one embodiment the invention provides a statistically significant difference, or reduction, or improvement in the week 4 GCSI-24H total score.

In one embodiment, the invention relates to a method to provide a statistically significant difference, reduction, and/or improvement in the Week 4 GCSI-24H total score and along all the treatment time by administration of about 5 mg velusetrag or lower.

In another embodiment, the invention provides a significant improvement in symptoms of postprandial fullness/early satiety, bloating, upper abdominal pain, epigastric burning, nausea and vomiting by administration of 5 mg velusetrag or lower.

In another embodiment, the invention provides a significant improvement in symptoms of postprandial fullness/early satiety, bloating, upper abdominal pain, epigastric burning, nausea and vomiting by administration of about 5 mg velusetrag or lower along all the treatment time.

In yet another embodiment, the invention provides a method for preventing, alleviating, ameliorating, reducing, giving relief to, and/or treating gastroparesis symptoms, wherein a reduction of symptoms from baseline in the treatment period mean composite GRS score over Week 1 through 3 and Weeks 5 through 12 or more of treatment. Likewise, the invention also provides a method for preventing, alleviating, ameliorating, reducing, giving relief to, and/or treating gastroparesis symptoms, wherein a reduction of symptoms from baseline in daily in the treatment period mean composite GRS individual component scores of the symptoms over Week 1 through 12 of treatment is provided. In another embodiment, the invention provides a method for preventing, alleviating, ameliorating, reducing, giving relief to, and/or treating gastroparesis symptoms, wherein a proportion of subjects provides at least 1-point improvement from baseline in the GRS individual components at each week (1-12) score over Week 1 through 3 and Weeks 5 through 12 of treatment and more in diabetic or idiopathic patients.

In one embodiment, the invention provides a method for preventing, alleviating, ameliorating, reducing, giving relief to, and/or treating gastroparesis symptoms, wherein a statistically significant difference, or reduction, or improvement in the week 4 GRS total score. In another embodiment, the invention provides a statistically significant difference, or reduction, or improvement in GRS total score in the Week 4, 8, 12 or along the treatment time in diabetic and idiopathic patients.

In another embodiment, the invention relates to a method to provide statistically significant difference, or reduction, or improvement in the Week 4 GRS total score by administration of velusetrag at a daily dosage from about 0.5 mg to about 30 mg, about 0.5 mg to about 15 mg, about 0.5 mg to about 5 mg, or about 5 mg.

The invention also provides a method for preventing, alleviating, ameliorating, reducing, giving relief to, and/or treating symptoms of gastroparesis by administration of a compound with a direct mechanism through the 5-$HT_4$ receptor complex.

In one embodiment, the invention provides a method for preventing, alleviating, ameliorating, reducing, giving relief to, and/or treating: postprandial fullness/early satiety, bloating, and upper abdominal pain, by the administration of velusetrag at daily dosage from about 0.5 to about 5 mg.

In another embodiment, the invention provides a method for preventing, alleviating, ameliorating, reducing, giving relief to, and/or treating fullness/early satiety, bloating, upper abdominal pain, and epigastric burning wherein a statistically significant LS mean difference higher than 0.4 points is obtained compared to placebo.

In yet another embodiment, the invention relates to a method for preventing, alleviating, ameliorating, reducing, giving relief to, and/or treating gastroparesis symptoms by providing a significant improvement in symptoms associated to gastroparesis in the Week 4 GRS total score with no tachyphylaxis effect with velusetrag from about 0.5 mg/day to about 30 mg/day, about 0.5 mg/day to about 15 mg/day, about 0.5 mg/day to about 5 mg/day, or about 5 mg/day.

In another embodiment, the invention relates to a method for preventing, alleviating, ameliorating, reducing, giving relief to, and/or treating gastroparesis symptoms, wherein at velusetrag daily dosage of about 5 mg, the reduction of symptoms of baseline GRS (Factor 1: fullness/early satiety, bloating, upper abdominal pain, epigastric burning) is higher than 0.2 for all the treatment time.

In yet another embodiment, the invention provides a method for preventing, alleviating, ameliorating, reducing, giving relief to, and/or treating gastroparesis symptoms in idiopathic patients, wherein at velusetrag daily dosage of about 5 mg, the reduction of symptoms of baseline GRS (Factor 1) is higher than 0.5 for all the treatment time.

In a further embodiment, the reduction of symptoms in velusetrag administration at daily dosage from about 0.5 mg to about 30 mg, are greater than 0.1 to 1.5 points from baseline in level of total symptom burden from severe symptoms to moderate/mild symptoms, or from moderate to mild/no symptoms.

In one embodiment, the invention relates to a method to normalize the gastric function by the administration of velusetrag at daily dosage from about 0.5 mg to about 30 mg.

In one embodiment, the invention provides a method for preventing, reducing, ameliorating, alleviating, giving relief to, and/or treating, nausea and vomiting wherein a statistically significant LS mean difference higher than 0.2 points compared to placebo.

The invention also relates to methods of preventing, alleviating, ameliorating, reducing, giving relief to, and/or treating symptoms associated to gastroparesis comprising administering a therapeutically amount of velusetrag to a subject in need thereof, in an amount from about 0.5 mg/day to about 30 mg/day or higher intended to treat a subset of core symptoms without to worsening the remaining symptoms of gastroparesis.

BRIEF DESCRIPTION OF THE DRAWINGS

Various aspects of the present invention are illustrated by reference to the accompanying drawings.

FIG. 4A illustrates GCSI-24H Total score by Age at 4 weeks.

FIG. 4B illustrates GCSI-24H Total score by Age at 12 weeks.

FIG. 15A illustrates GCSI-24H Responder Odd Ratio by Baseline Total score at 4 weeks.

FIG. 15B illustrates GCSI-24H Responder Odd Ratio by Baseline Total score at 12 weeks.

FIG. 21A illustrates GRS Total Score by type of Gastric Emptying Screening Test, historical and prospective at 4 weeks.

FIG. 21B illustrates GRS Total Score by type of Gastric Emptying Screening Test, historical and prospective at 12 weeks.

FIG. 23A illustrates GRS Total Score by Screening GES and GEBT Severity at 4 weeks.

FIG. 23B illustrates GRS Total Score by Screening GES and GEBT Severity at 12 weeks.

DETAILED DESCRIPTION OF THE INVENTION

Figure 1:
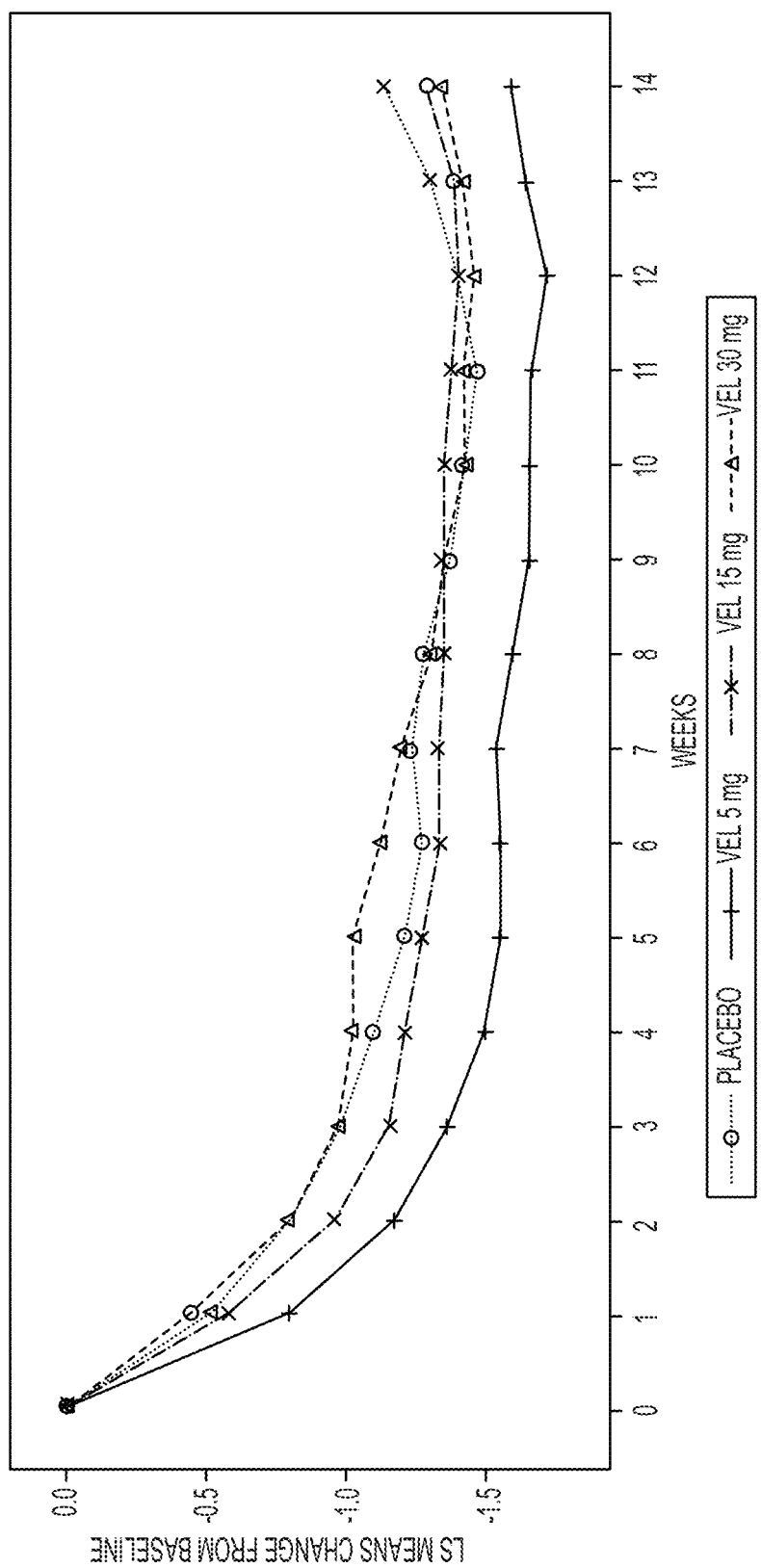
FIG. 1 illustrates the LS Mean differences in each sub-group change from baseline in weekly GCSI-24H I at week 4 and week 12. LS was calculated based on repeated measures mixed model with change from baseline in weekly GCSI-24H total score as dependent, variable, treatment, gastroparesis type (diabetic vs idiopathic), GE test time (historical vs. prospective), baseline GCSI total score, time (categorical), interaction effect of treatment by time, baseline GCSI total score by time, treatment by gastroparesis type and treatment by time by gastroparesis type as fixed effect, a random effect of subject within site, using an unstructured covariance structure.
Figure 2A:
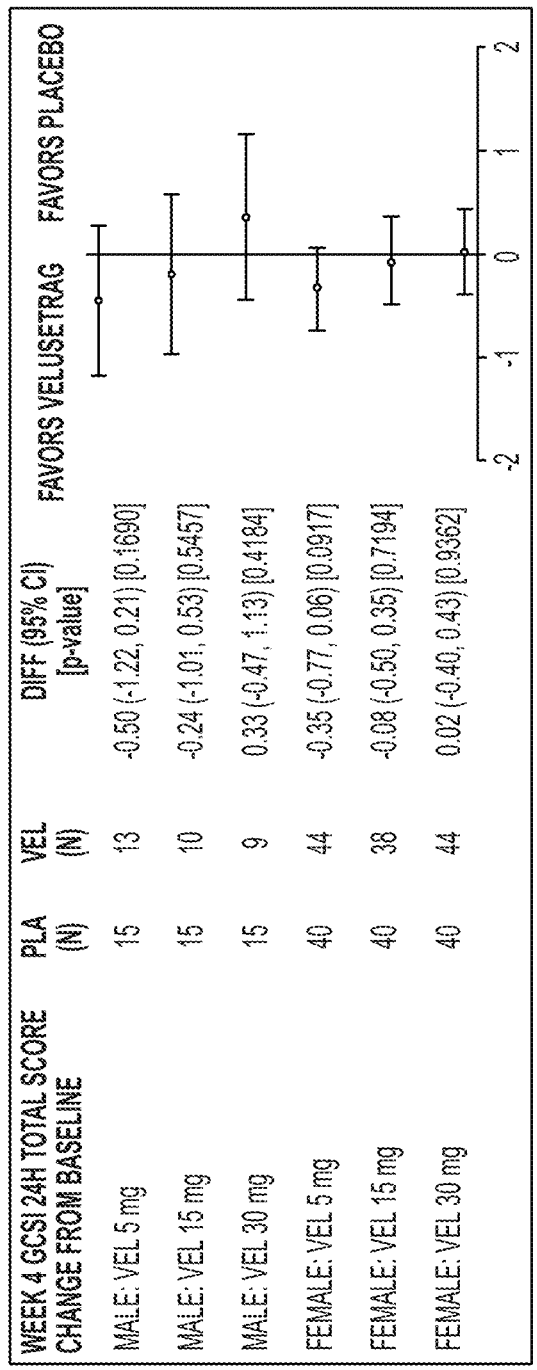
FIG. 2A illustrates GCSI-24H Total score by Sex at 4 weeks.
Figure 2B:
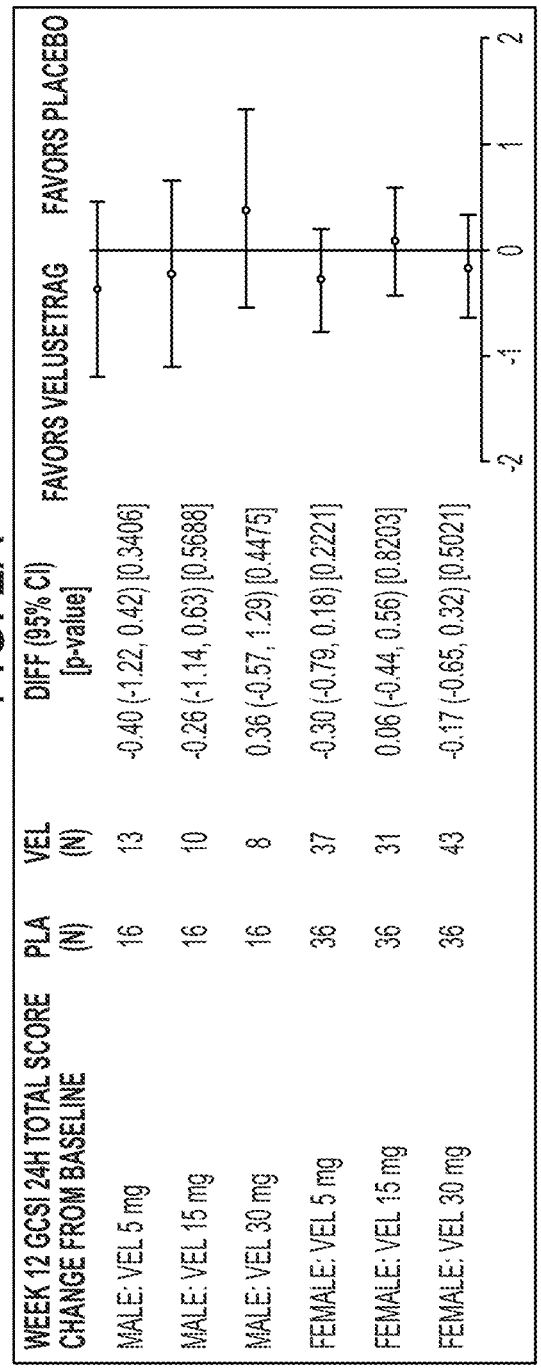
FIG. 2B illustrates GCSI-24H Total score by Sex at 12 weeks.
Figure 3A:
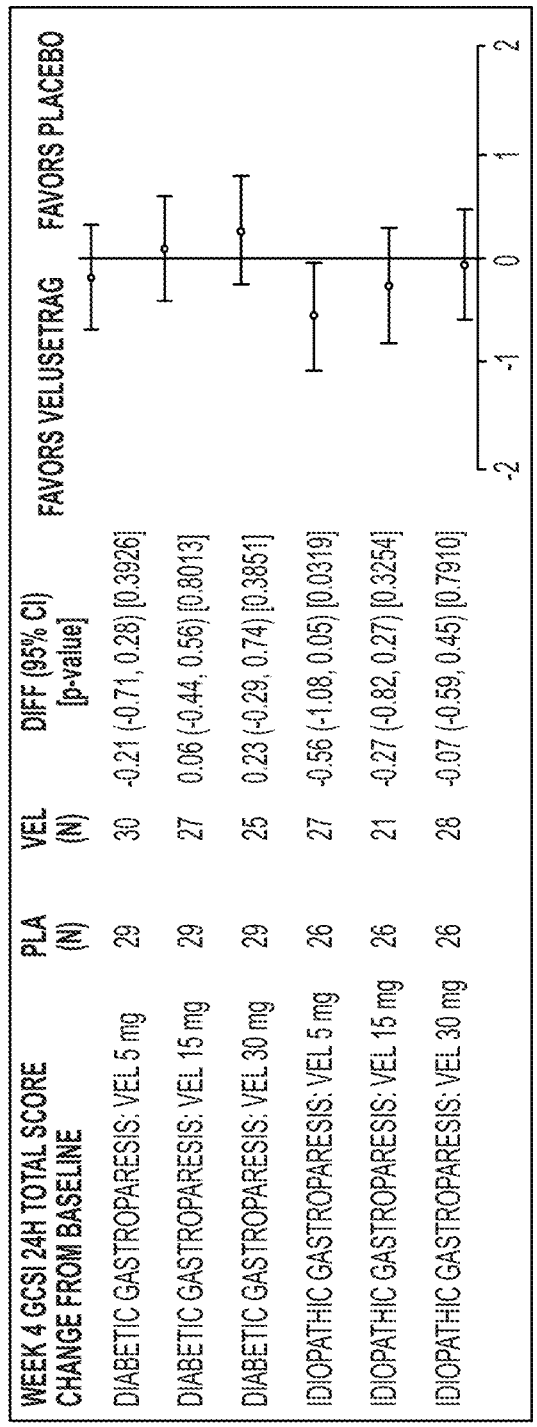
FIG. 3A illustrates GCSI-24H Total score by Gastroparesis Type at 4 weeks.
Figure 3B:
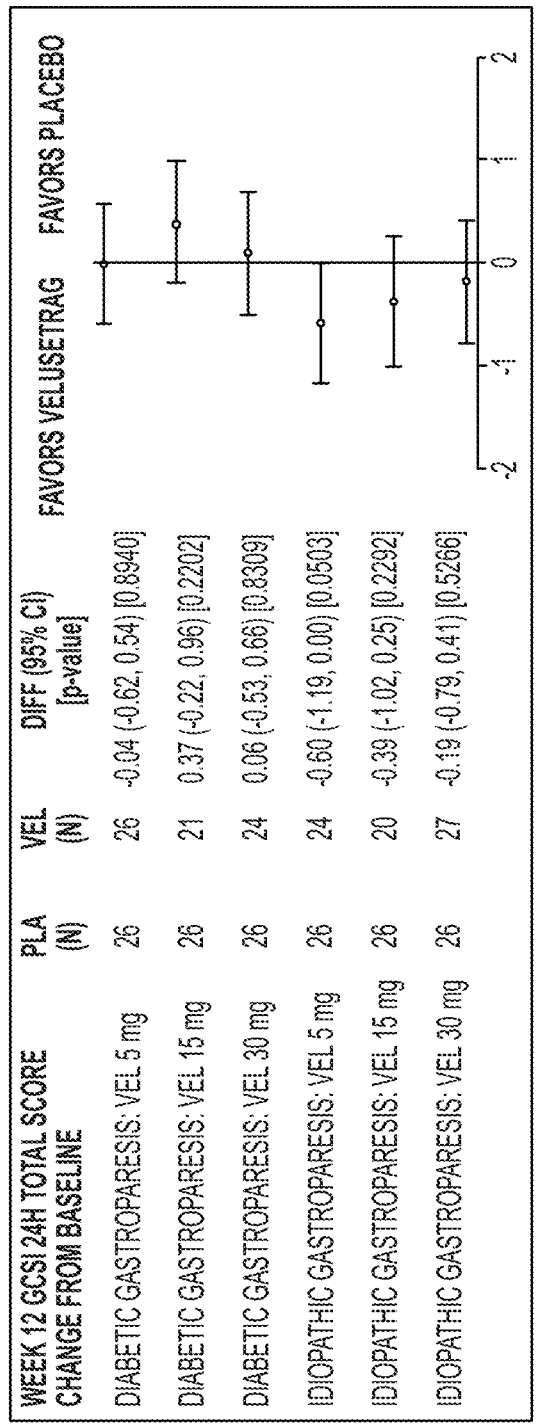
FIG. 3B illustrates GCSI-24H Total score by Gastroparesis Type at 12 weeks.
Figure 5A:
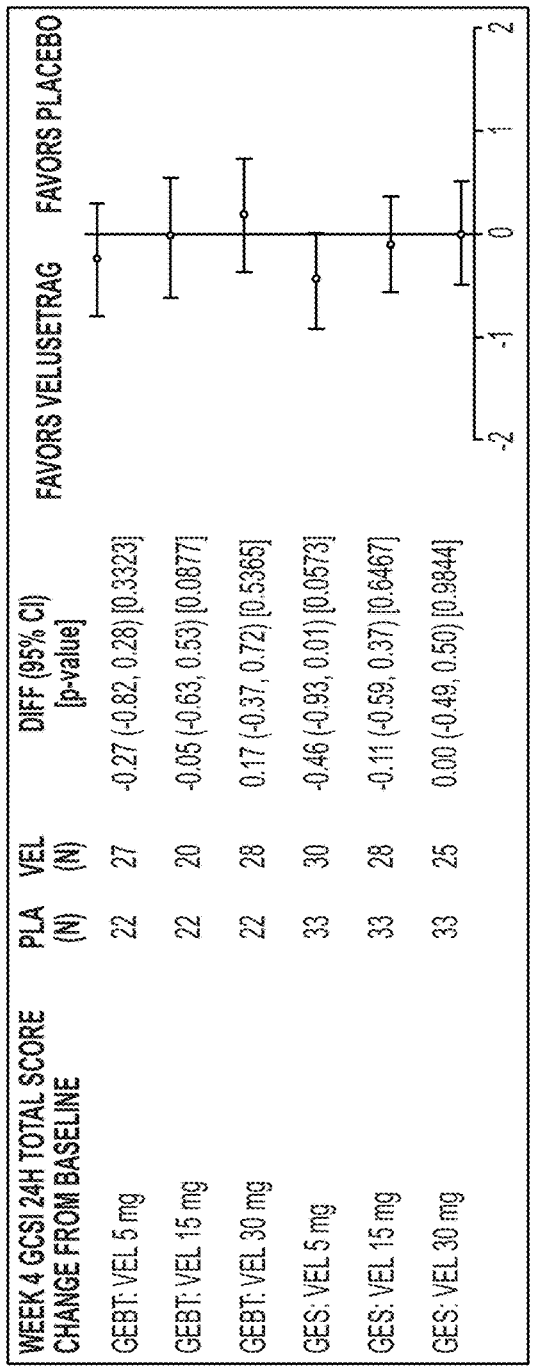
FIG. 5A illustrates GCSI-24H Total Score by type of Gastric Emptying Screening Test at 4 weeks.
Figure 5B:
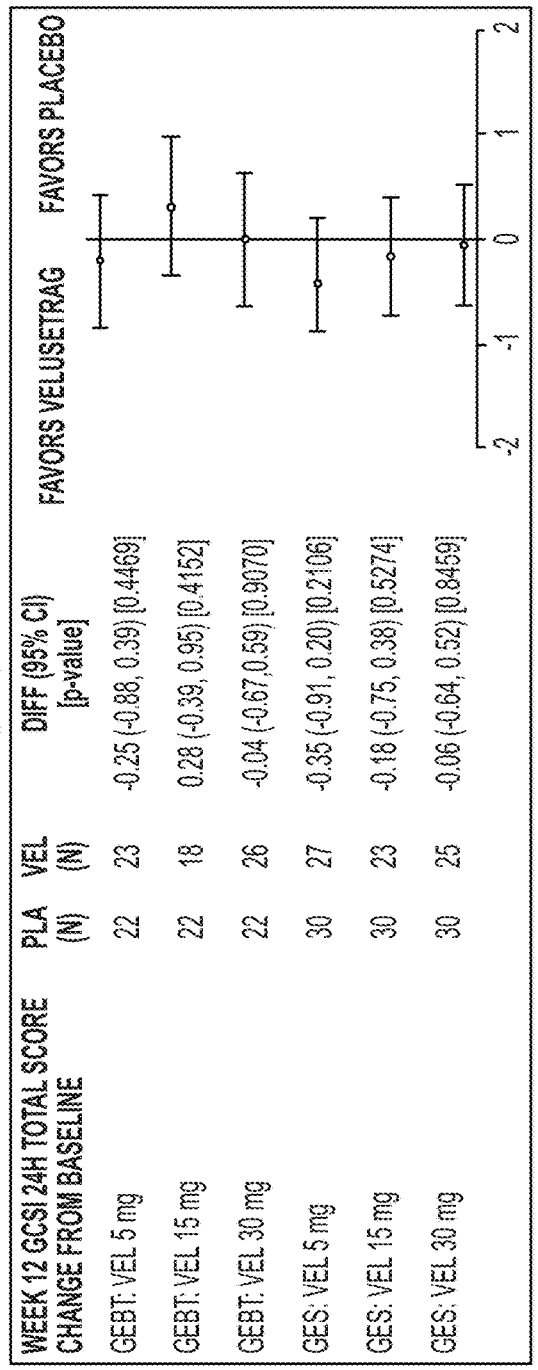
FIG. 5B illustrates GCSI-24H Total Score by type of Gastric Emptying Screening Test at 12 weeks.
Figure 6A:
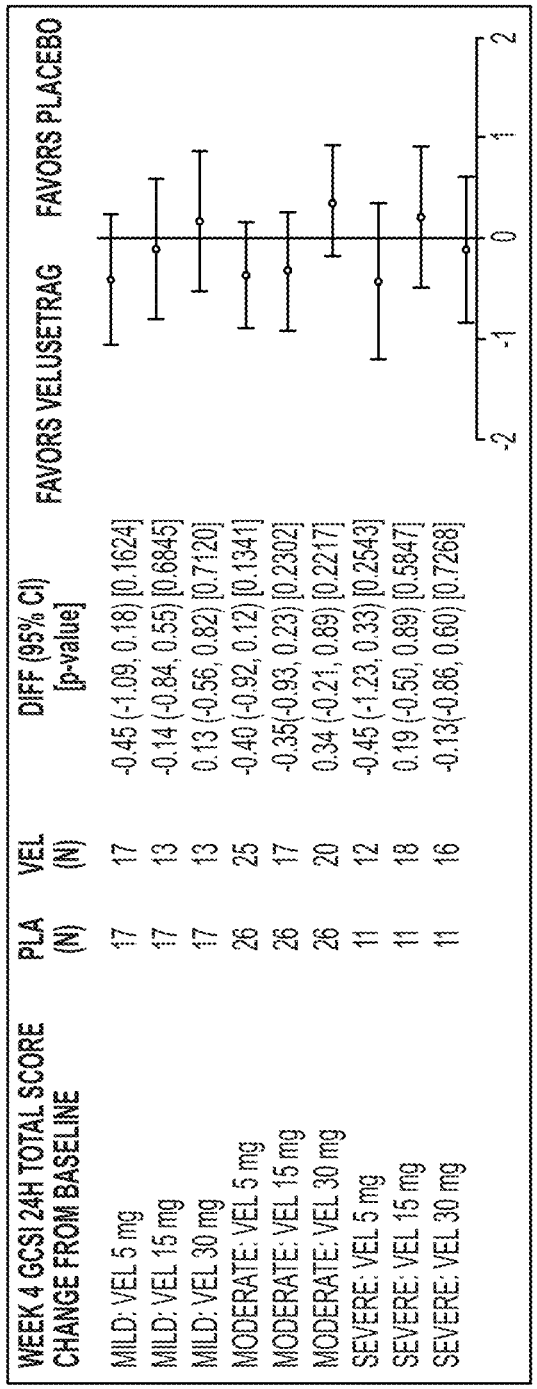
FIG. 6A illustrates GCSI-24H Total score by Screening GES and GEBT Severity at 4 weeks.
Figure 6B:
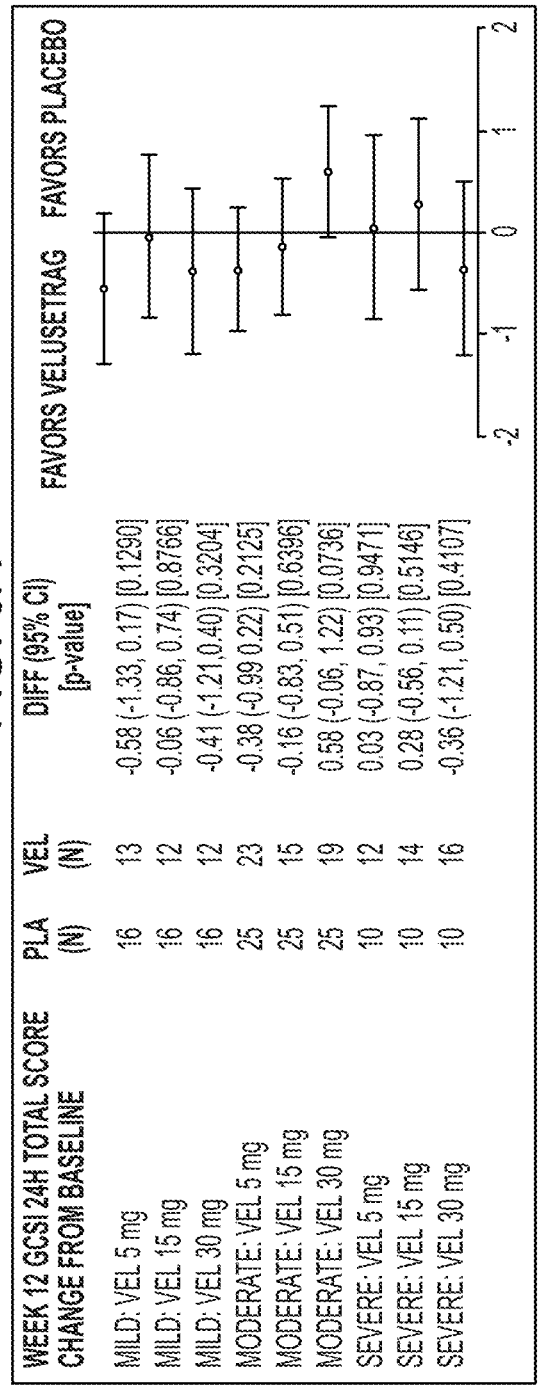
FIG. 6B illustrates GCSI-24H Total score by Screening GES and GEBT Severity at 12 weeks.
Figure 7A:
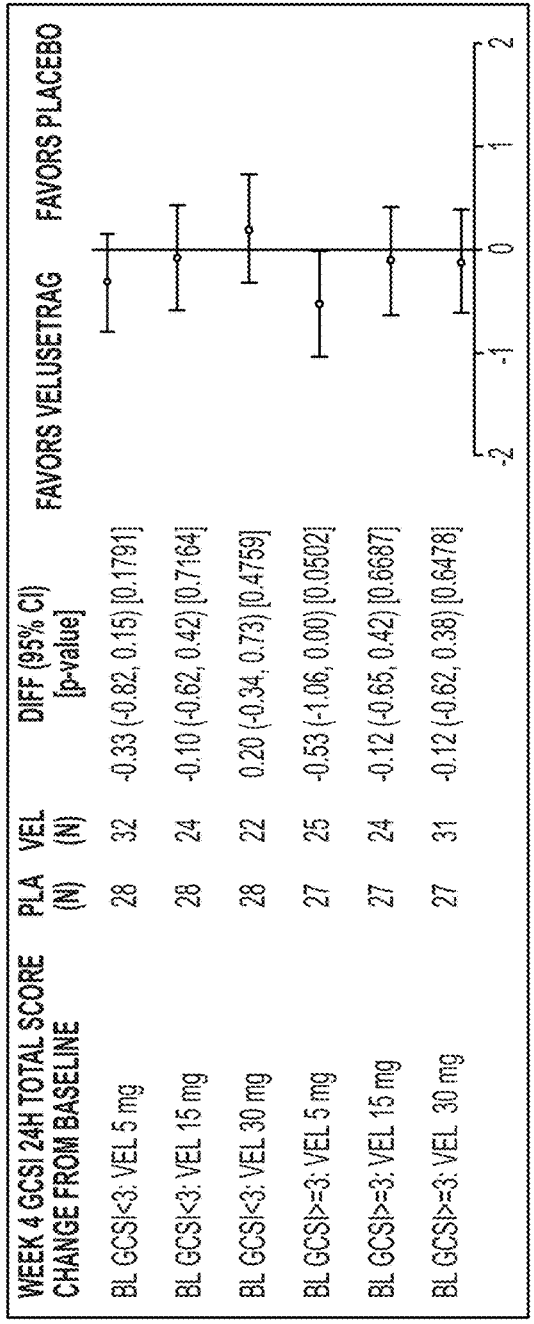
FIG. 7A illustrates GCSI-24H, Total Score by Baseline Total score at 4 weeks.
Figure 7B:
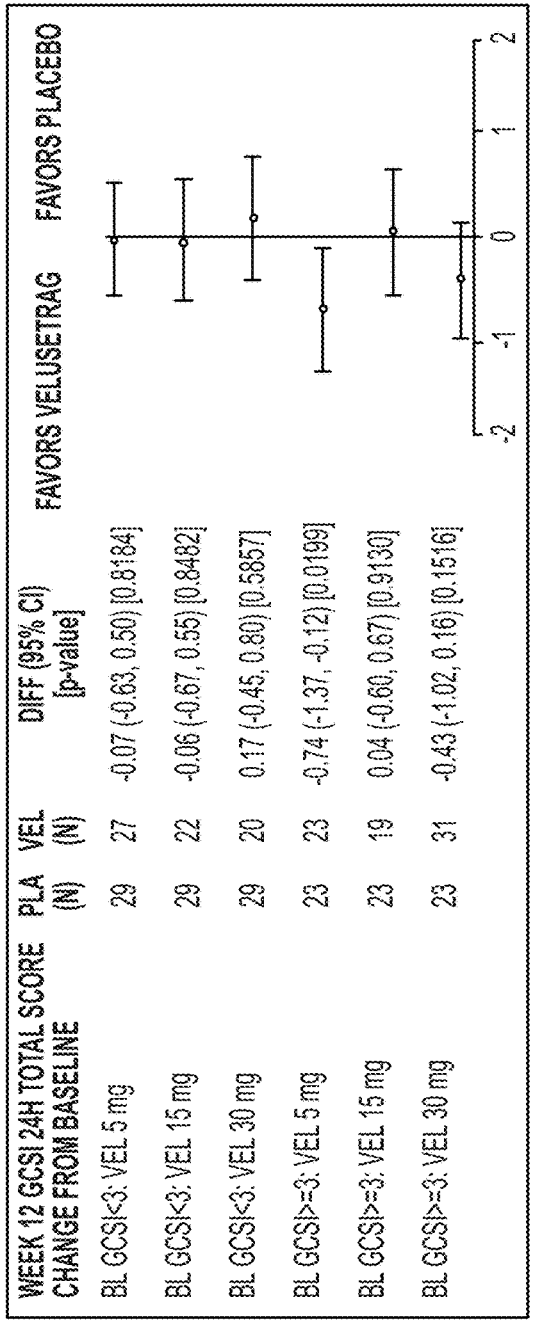
FIG. 7B illustrates GCSI-24H, Total Score by Baseline Total score at 12 weeks.
Figure 8A:
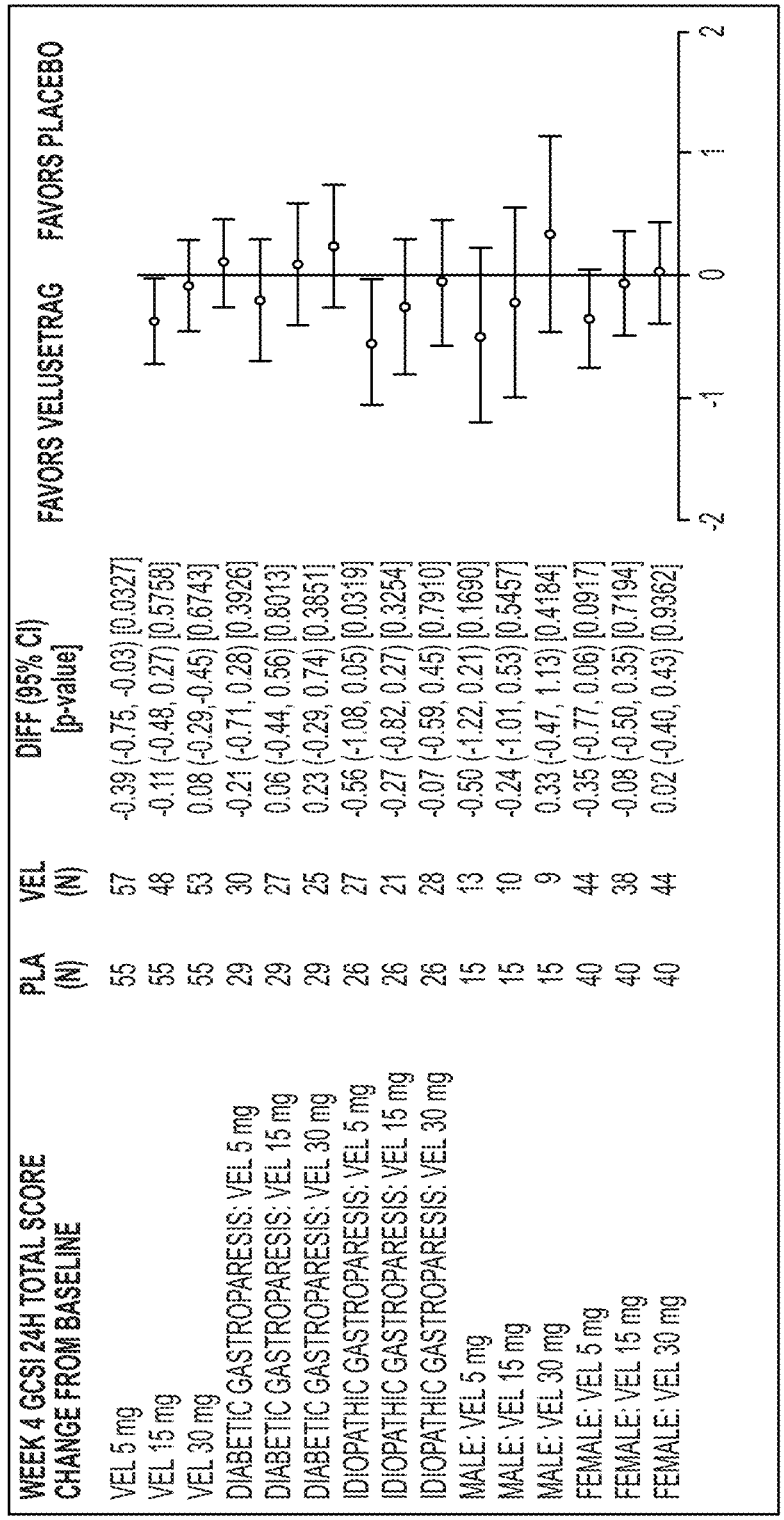
FIG. 8A illustrates GCSI-24H Total Score at 4 weeks by diabetic and idiopathic gastroparesis type and by sex.
Figure 8B:
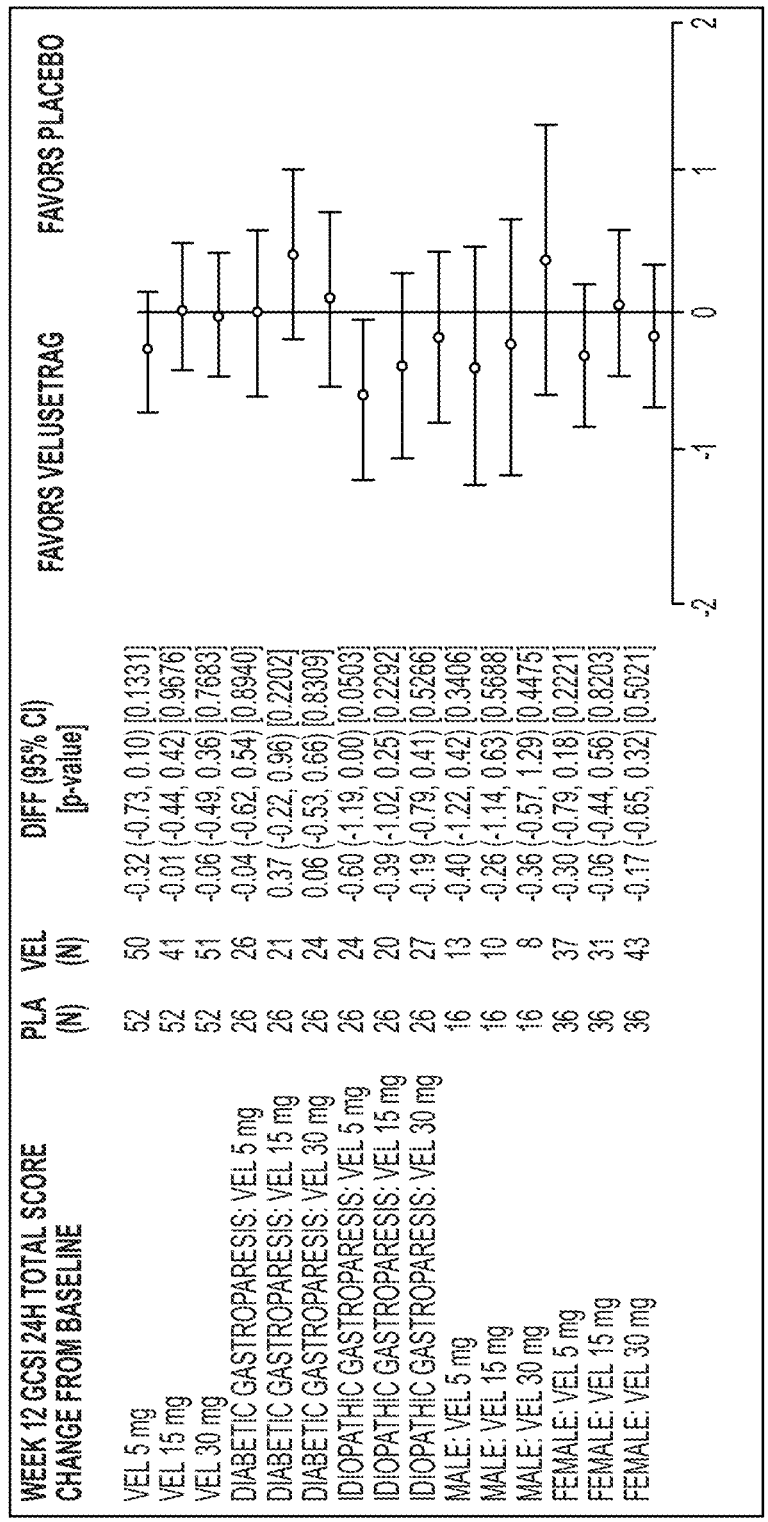
FIG. 8B illustrates GCSI-24H Total Score at 12 weeks by diabetic and idiopathic gastroparesis type and by sex.
Figure 9A:
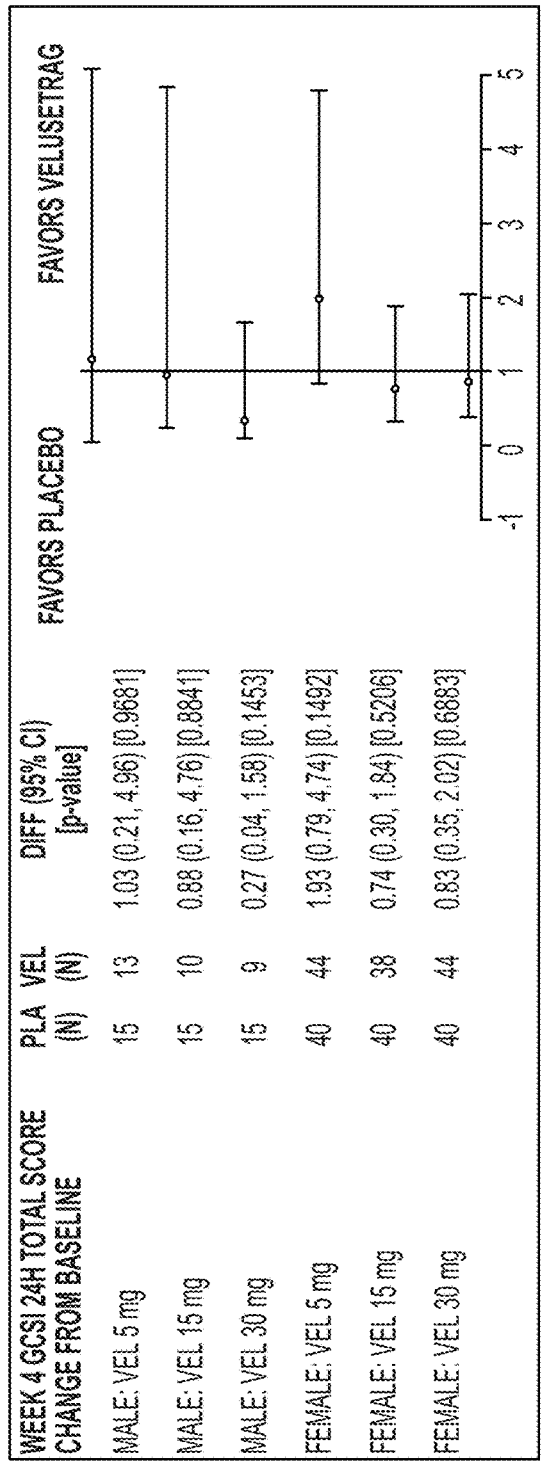
FIG. 9A illustrates GCSI-24H Responder Odd Ratio by Sex at 4 weeks.
Figure 9B:
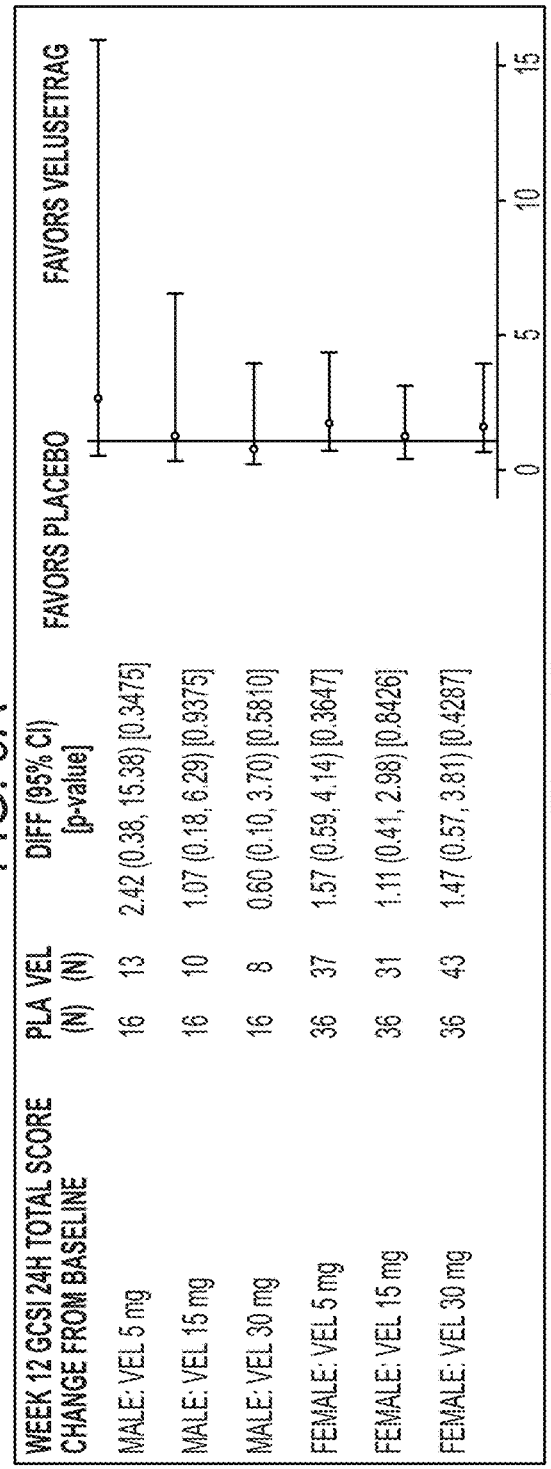
FIG. 9B illustrates GCSI-24H Responder Odd Ratio by Sex at 12 weeks.
Figure 10A:
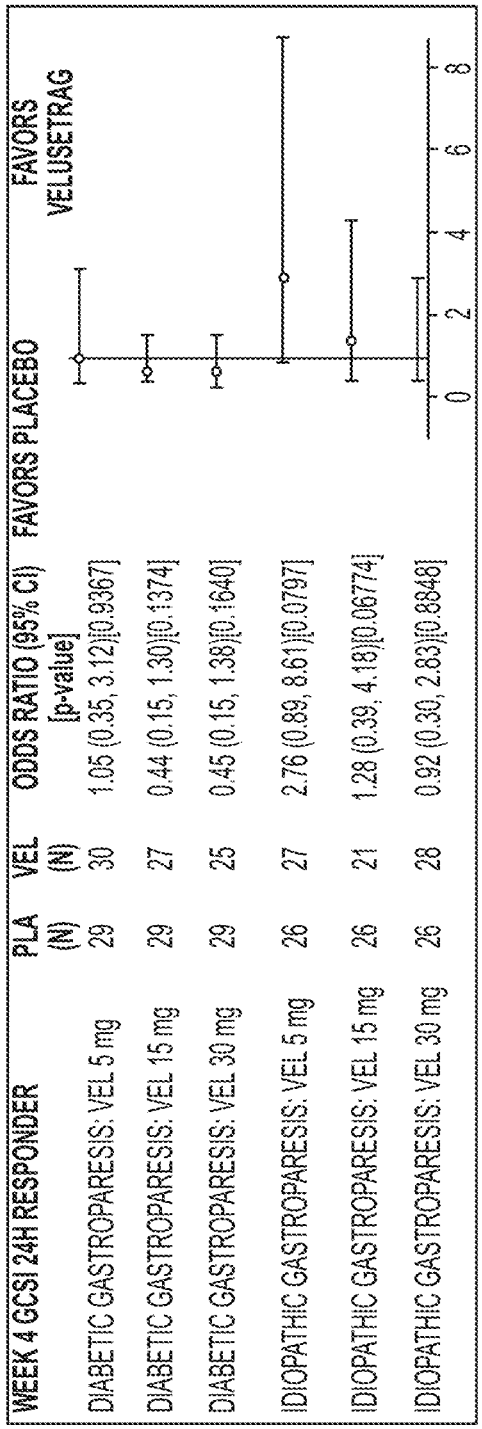
FIG. 10A illustrates GCSI-24H Responder Odd Ratio by Gastroparesis Type at 4 weeks.
Figure 10B:
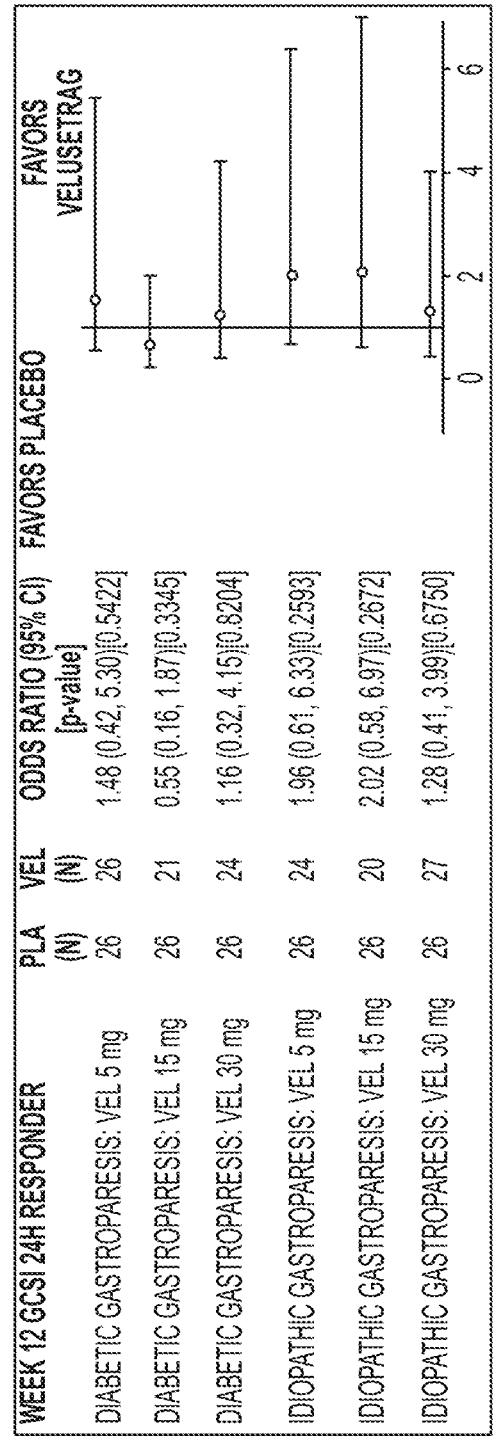
FIG. 10B illustrates GCSI-24H Responder Odd Ratio by Gastroparesis Type at 12 weeks.
Figure 11A:
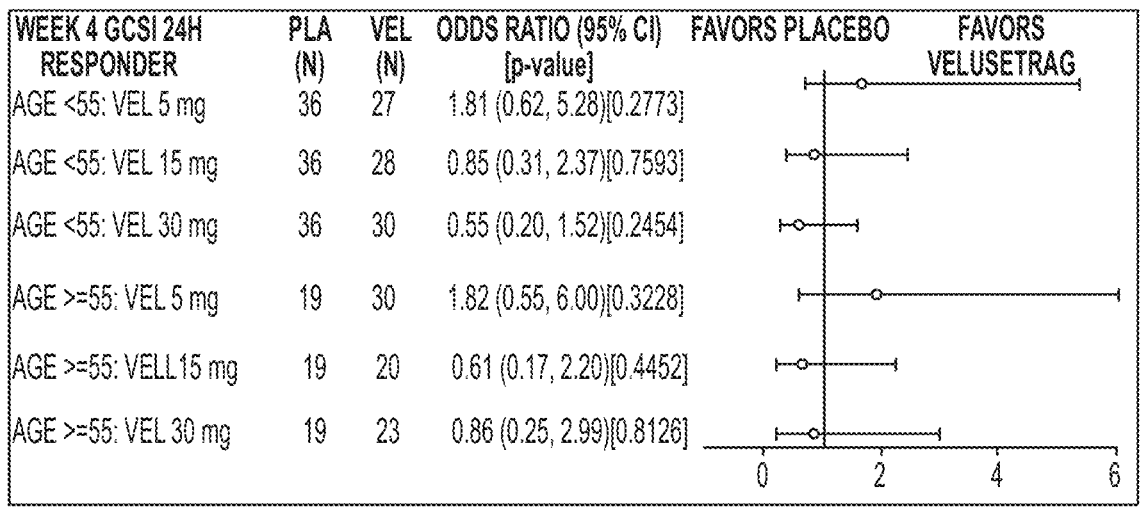
FIG. 11A illustrates GCSI-24H Responder Odd Ratio by Age at 4 weeks.
Figure 11B:
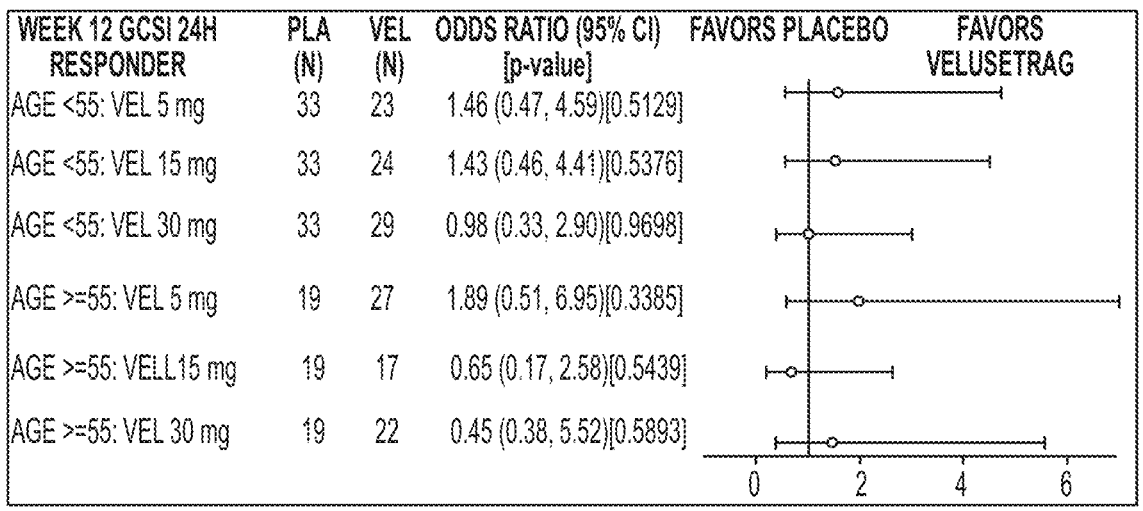
FIG. 11B illustrates GCSI-24H Responder Odd Ratio by Age at 12 weeks.
Figure 12A:
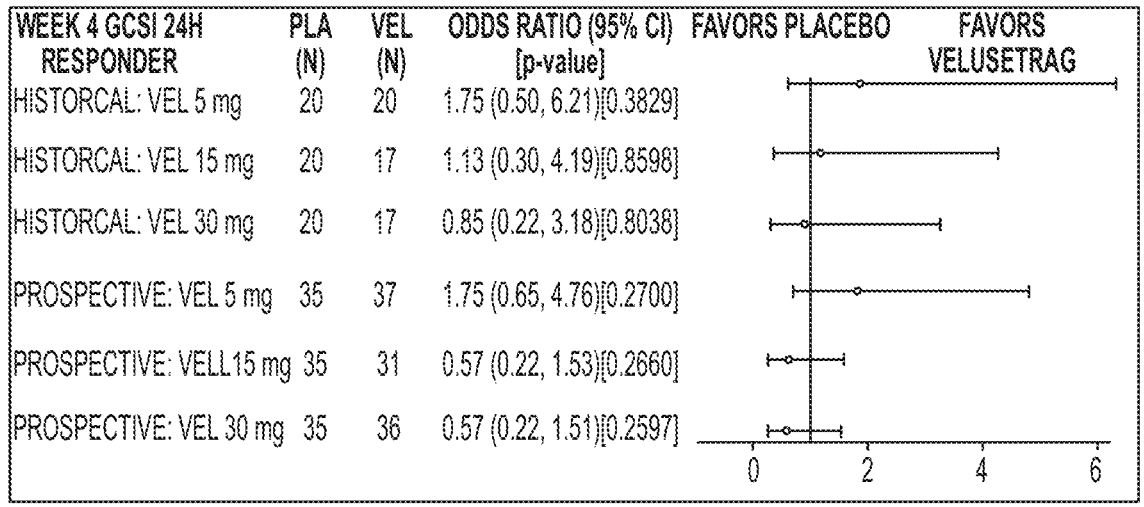
FIG. 12A illustrates GCSI-24H Responder Odd Ratio by type of Gastric Emptying Screening Test, historical and prospective at 4 weeks.
Figure 12B:
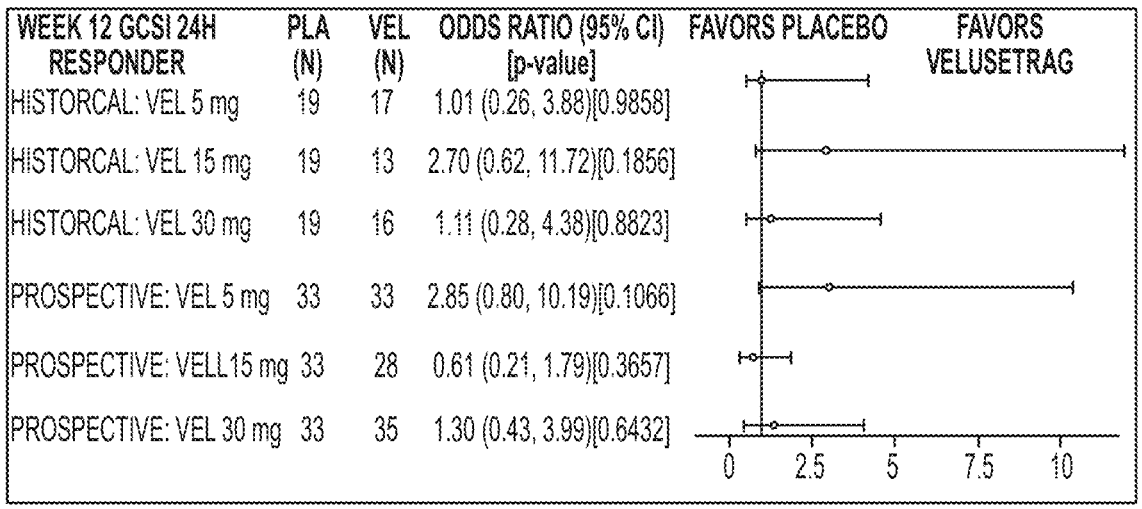
FIG. 12B illustrates GCSI-24H Responder Odd Ratio by type of Gastric Emptying Screening Test, historical and prospective at 4 weeks.
Figure 13A:
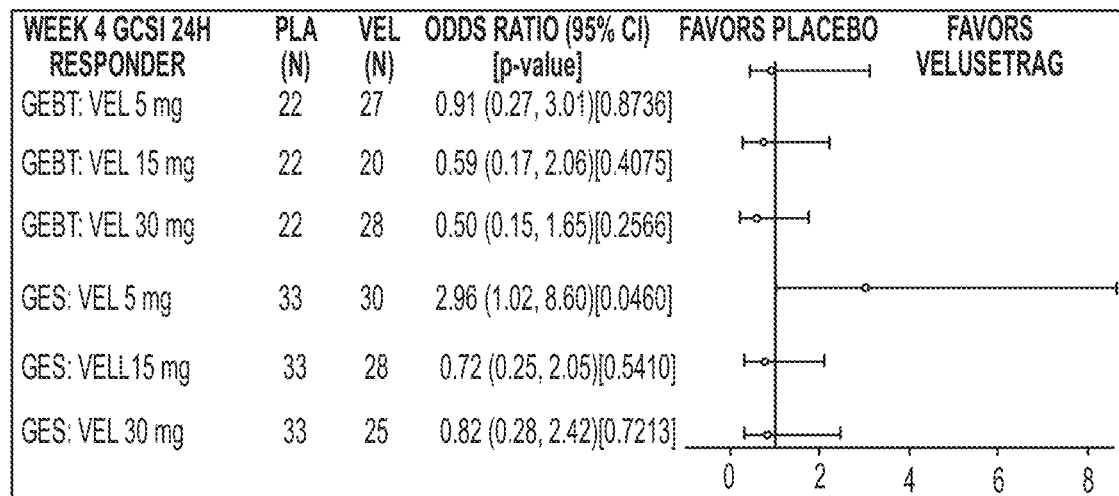
FIG. 13A illustrates GCSI-24H Responder Odd Ratio by type of Gastric Emptying Screening Test at 4 weeks.
Figure 13B:
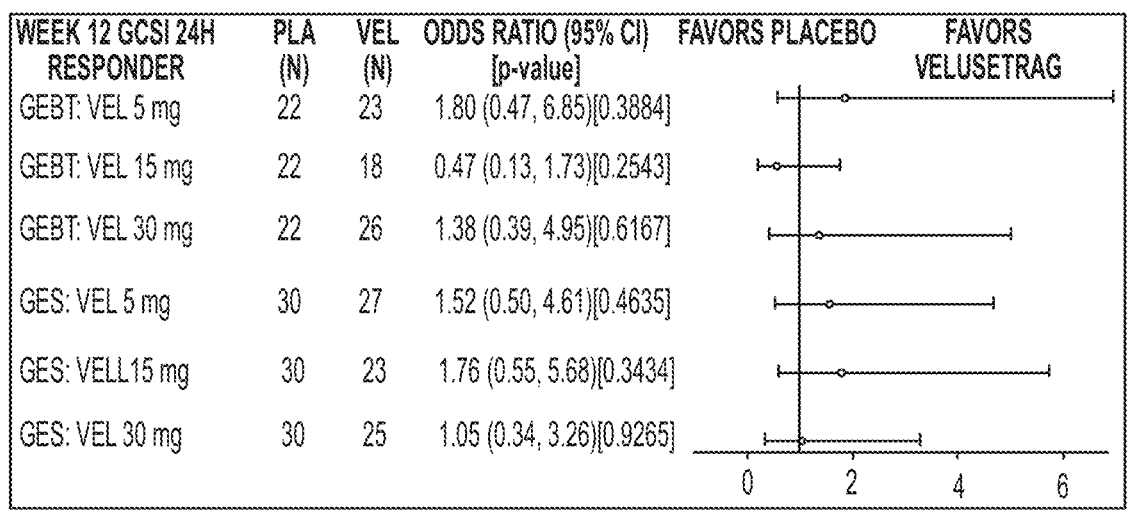
FIG. 13B illustrates GCSI-24H Responder Odd Ratio by type of Gastric Emptying Screening Test at 12 weeks.
Figure 14A:
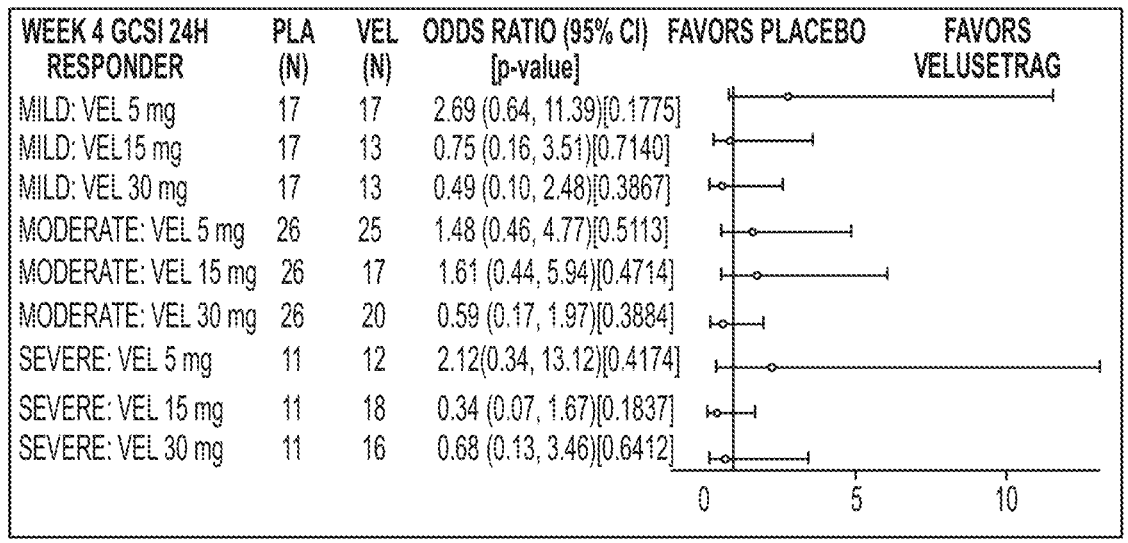
FIG. 14A illustrates GCSI-24H Responder Odd Ratio by Screening GES and GEBT Severity at 4 weeks.
Figure 14B:
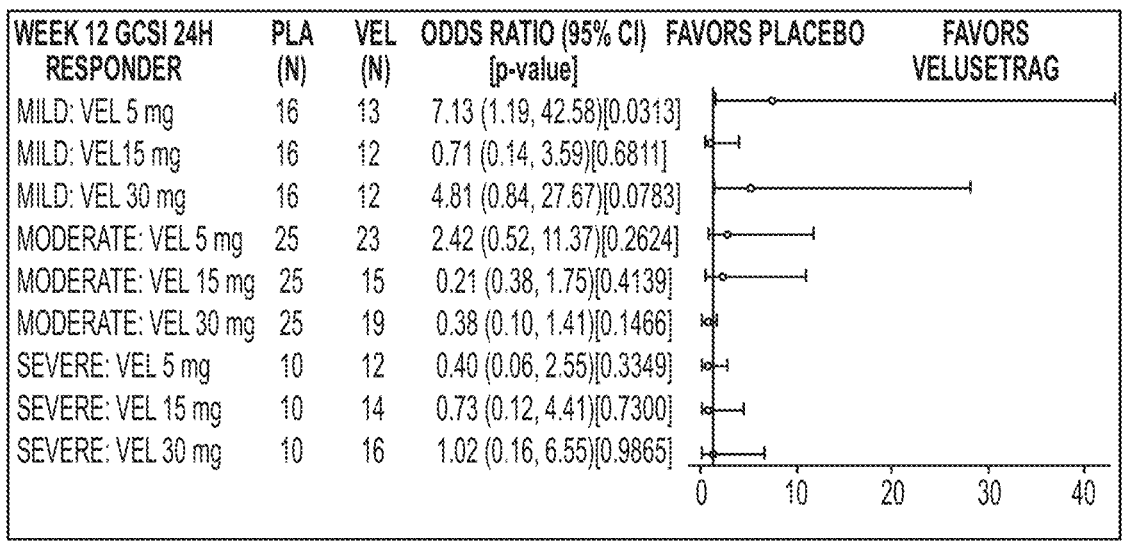
FIG. 14B illustrates GCSI-24H Responder Odd Ratio by Screening GES and GEBT Severity at 12 weeks.
Figure 16A:
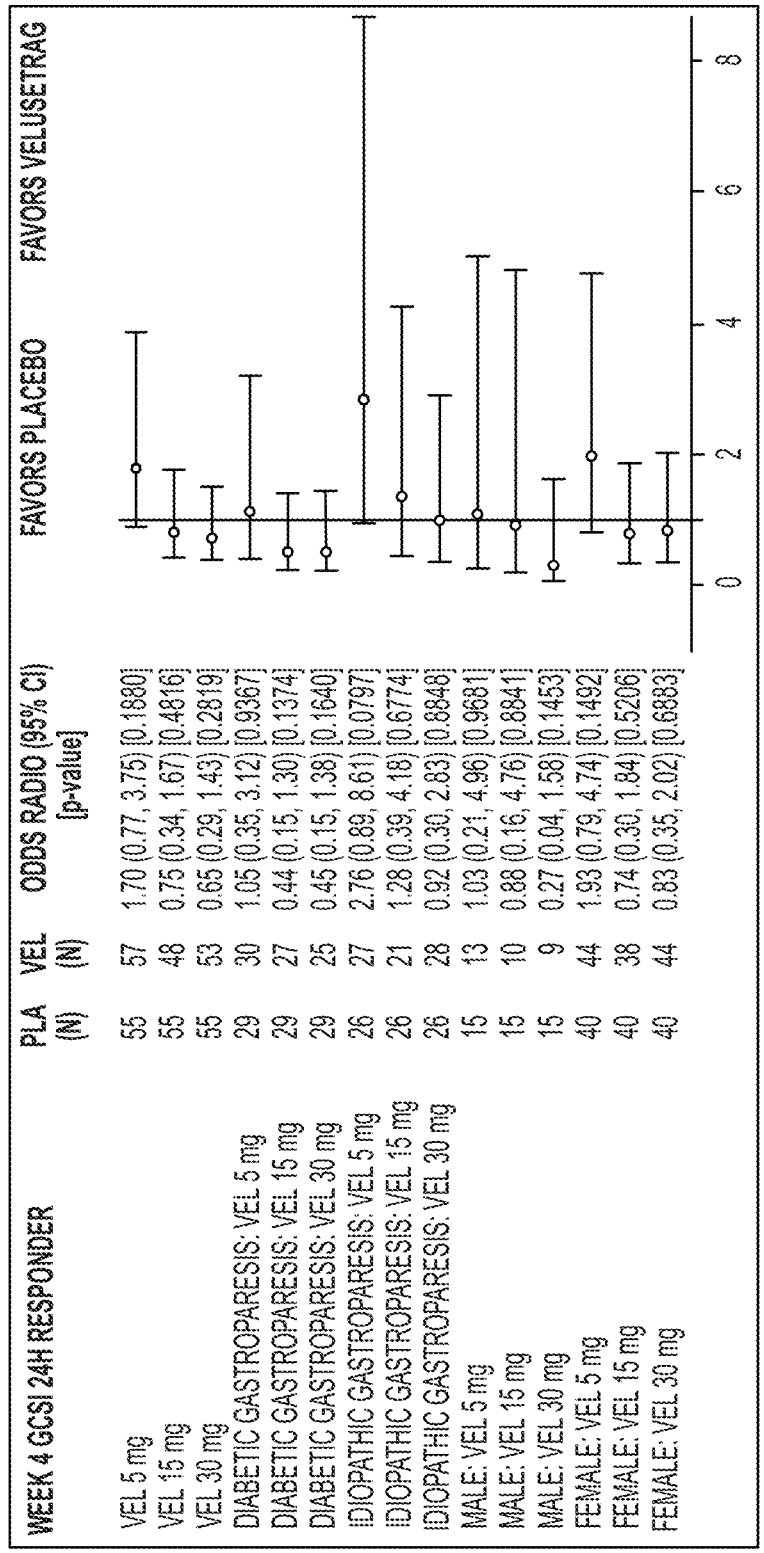
FIG. 16A illustrates GCSI-24H Responder Odd Ratio by diabetic and idiopathic gastroparesis type and by sex at 4 weeks.
Figure 16B:
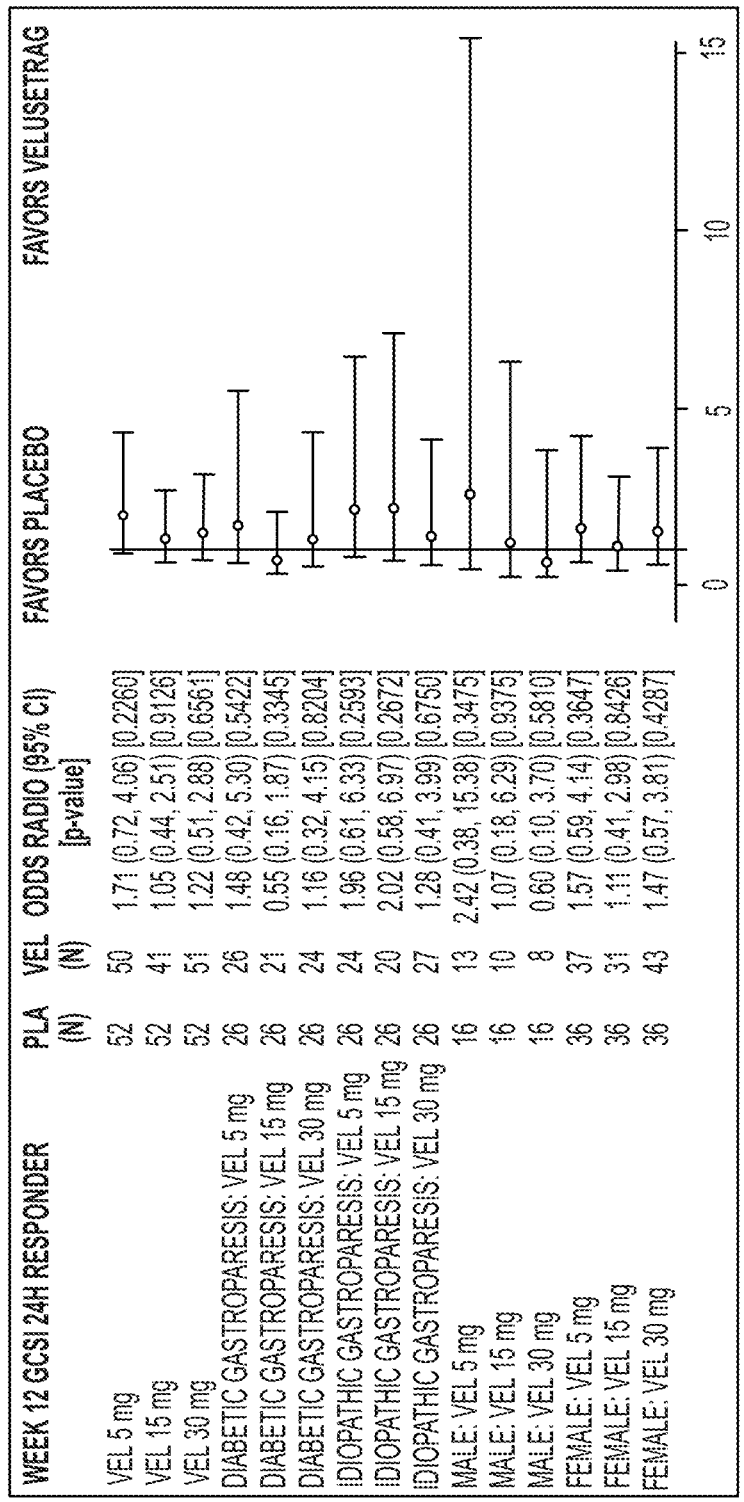
FIG. 16B illustrates GCSI-24H Responder Odd Ratio by diabetic and idiopathic gastroparesis type and by sex at 12 weeks.

Velusetrag is a compound of Formula I and forms a crystalline hydrochloride salt as shown in Formula II:

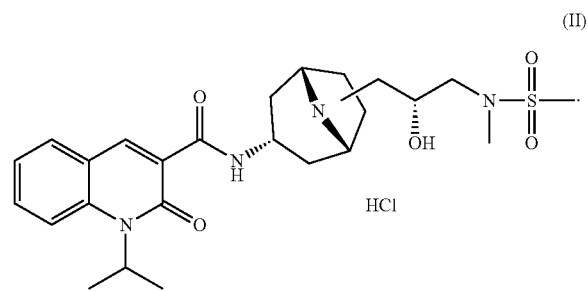

(II)

Velusetrag, and its pharmaceutically-acceptable salt, is a highly selective 5-hydroxytryptamine subtype 4 (5-HT$_4$) useful for treatment of gastroparesis, chronic idiopathic constipation, as well as other indications, see, e.g., indications found in U.S. Pat. Nos. 7,375,114, 7,728,004, and 8,404,711.

The current invention relates in part to treatment of symptoms associated with gastroparesis in a human patient with the hydrochloride salt of velusetrag at a dose between about 0.5 mg and 30 mg, 0.5 mg to 15 mg, 0.5 mg to 5 mg, or about 5 mg, daily As noted above, gastroparesis is a multi-symptom disorder of the stomach characterized by delayed gastric emptying in the absence of mechanical obstruction (Parkman, H. P., et al., *Gastroenterology*, 2004, 127(5), 1592-1622). The underlying gastric delay is thought to be the mechanism through which the symptoms arise, although the exact relationship between functional delay and symptomology has not been demonstrated consistently (Ardila-Hani, et al., *Dig. Dis. Sci.*, 2013, 58(2), 478-487).

In order to assess the symptoms of gastroparesis, a Phase 2b (DIGEST I) study was conducted. The study enrolled a total of 233 patients with gastroparesis, with approximately 50% having diabetic gastroparesis and 50% having idiopathic gastroparesis.

In the evaluation of the efficacy of velusetrag, the enrollment of the idiopathic patients allowed for selection and evaluation of the symptoms and their decrease.

A pharmaceutically effective amount or therapeutically effective amount for the method described herein may also be used to treat gastroparesis in a human patient. This daily dosage may be between about 0.5 mg and about 15 mg, including 0.5 mg, 1 mg, 1.2 mg, 1.4 mg, 1.6 mg, 1.8 mg, 2.0 mg, 2.2 mg, 2.4 mg, 2.6 mg, 2.8 mg, 3.0 mg, 3.2 mg, 3.4 mg, 3.6 mg, 3.8 mg, 4.0 mg, 4.2 mg, 4.4 mg, 4.6 mg, 4.8 mg, 5.0 mg, 5.2 mg, 5.4 mg, 5.6 mg, 5.8 mg, 6.0 mg, 6.2 mg, 6.4 mg, 6.6 mg, 6.8 mg, 7.0 mg, 7.2 mg, 7.4 mg, 7.6 mg, 7.8 mg, 8.0 mg, 8.2 mg, 8.4 mg, 8.6 mg, 8.8 mg, 9.0 mg, 9.2 mg, 9.4 mg, 9.6 mg, 9.8 mg, 10.0 mg, 10.2 mg, 10.4 mg, 10.6 mg, 10.8 mg, 11.0 mg, 11.2 mg, 11.4 mg, 11.6 mg, 11.8 mg, 12.0 mg, 12.2 mg, 12.4 mg, 12.6 mg, 12.8 mg, 13.0 mg, 13.2 mg 13.4 mg, 13.6 mg, 13.8 mg, 14.0 mg, 14.2 mg, 14.4 mg, 14.6 mg, or 14.8 mg of velusetrag. Alternatively, the daily dosage may be between about 1 mg and about 15 mg, including 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg, 12.0 mg, 12.5 mg, 13.0 mg, 13.5 mg, 14.0 mg, or 14.5 mg of velusetrag. In a preferred embodiment, velusetrag, optionally in the form of a pharmaceutically-acceptable salt thereof, is administered at a daily dose of 5 mg. If a pharmaceutically-acceptable salt of velusetrag is used, the amount of velusetrag listed above is adjusted for the weight of the salt.

In one embodiment, the pharmaceutically-acceptable salt of velusetrag is a hydrochloride salt of velusetrag. A crystalline hydrochloride salt of the invention typically contains between about 0.8 and about 1.2 molar equivalents of hydrochloric acid per molar equivalent of the compound of formula I, including between about 0.9 and about 1.1 molar equivalents of hydrochloric acid per molar equivalent of the compound of formula I.

In addition to its salt form, velusetrag may be in crystalline and/or hydrated form. In yet another embodiment, velusetrag is in a crystalline form as described in U.S. Pat. No. 7,728,004 and described herein in the Examples.

Gastroparesis can occur secondary to various chronic diseases such as diabetes, neurological disorders (Parkinson's disease, Myotonic dystrophy, migraines, and autonomic dysfunction), collagen vascular diseases (scleroderma or Ehlers-Danlos Syndrome), and chronic fatigue syndrome. Gastroparesis can also occur following surgery (Nissen fundoplication, Whipple, transplant) or viral infection. More commonly, the cause of gastroparesis is unknown or idiopathic. Diabetic and idiopathic gastroparesis comprise the majority of patients (Soykan, I., et al., *Dig Dis Sci.*, 1998, 43(11), 2398-2404; Karamanolis, et al., *Gut,* 2007, 56(1), 29-36). Additionally, there is significant overlap between idiopathic gastroparesis and functional dyspepsia such that 37% of patients who met Rome II criteria for functional dyspepsia have delayed gastric emptying (Tack, J., et al., *Gastroenterology,* 2004, 127(4), 1239-1255).

In one embodiment of the invention, the method of treatment focuses on the symptoms connected with diabetic or idiopathic gastroparesis. In yet another embodiment, the administration of velusetrag in the diabetic gastroparesis patient results in little to no increase in hyperglycemia and/or glucose.

Gastroparesis symptoms are typically chronic with episodic exacerbation and can be highly burdensome to both the individual (morbidity and mortality) and society (healthcare utilization) (Parkman, H. P., et al., *Gastroenterology,* 2004, 127(5), 1592-1622; Parkman, H. P., et al., *Clin. Gastroenterol. Hepatol.,* 2011, 9(12), 1056-1064; Jung, et al., *Gastroenterology,* 2009, 136(4), 1225-1233). In an analysis of subjects enrolled in a gastroparesis registry, 89% of subjects had chronic symptoms with 75% of those subjects having a worsening of symptoms over time or periodic exacerbations. Only 11% of subjects rated their symptoms as cyclic in nature where a short term therapeutic option, such as metoclopramide, is likely to be of benefit (Parkman, H. P., et al., *Clin. Gastroenterol. Hepatol.,* 2011, 9(12), 1056-1064).

The cardinal gastroparesis symptoms include nausea, vomiting, bloating, postprandial fullness, early satiety, and upper abdominal pain (Soykan, I., et al., *Dig Dis Sci.*, 1998, 43(11), 2398-2404). Patients may experience any combination of symptoms with varying degrees of severity across each symptom. Nausea is a nearly universal symptom, to some degree, in patients with gastroparesis and is the most common reason for gastroparesis evaluation (Parkman, H. P., et al., *Clin. Gastroenterol. Hepatol.,* 2011, 9(12), 1056-1064). Nausea and upper abdominal pain are reported by up to 90% of patients (Soykan, I., et al., *Dig Dis Sci.*, 1998, 43(11), 2398-2404; Cherian, D., et al., *Clin. Gastroenterol. Hepatol.*, 2010, 8(8), 676-681); these patients also frequently report daily vomiting, early satiety, postprandial fullness, and bloating (Hasler, W., *Nat. Rev. Gastroenterol. Hepatol.*, 2011, 8(8), 438-453). In particular, pain and bloating are considered the most restrictive symptoms in terms of quality of life (QOL) and impact on ability to maintain employment; their intensity is often correlated with the severity of other symptoms (Hasler, W., *Nat. Rev. Gastroenterol. Hepatol.*, 2011, 8(8), 438-453; Hasler, W., et al., *Am. J. Gastroenerol.*, 2011, 106(8), 1492-1502).

The incidence and prevalence of gastroparesis are not well described; however, the number of individuals affected by symptoms in the United States (U.S.) is estimated to be greater than 4 million (Stein, B., et al., *J. Clin. Gastroenterol.*, 2015, 49(7)). This condition predominantly affects young adult females into adulthood. The incidence, specified as typical symptoms and delayed gastric emptying confirmed by scintigraphy, in a community-based study (1996-2006) was 2.4/100,000 for men and 9.8/100,000 for women (Jung, et al., *Gastroenterology*, 2009, 136(4), 1225-1233).

While there are challenges in the correlation of severity of delays in gastric emptying by scintigraphy and symptoms, the Gastroparesis Consortium has reported that early satiety and postprandial fullness are common symptoms in patients. Increasing severity of these symptoms was associated with increasing gastric retention of a solid meal and decreased volume during water load test. In addition, these symptoms were also associated with other gastroparesis symptoms including nausea/vomiting, early satiety/postprandial fullness, bloating, and upper abdominal pain and gastroesophageal reflux disease (GERD) sub scores. Increasing severity of early satiety and postprandial fullness were also associated with increasing gastroparesis severity, decreased body-mass-index (BMI), and decreased quality of life (QOL) from Patient Assessment of Upper Gastrointestinal Symptom Severity Index (PAGI)-QOL and short form (SF)-36 physical health survey (Parkman, H. P., et al., *Neurogastroenterol. Motil.*, 2017, 29(4).

The impact of gastroparesis on overall QOL and employment stability are not inconsequential. Abdominal pain, bloating, and nausea are considered the most restrictive symptoms of gastroparesis. Importantly, their intensity is often correlated with the severity of other symptoms that ultimately can markedly impair health-related QOL (Hasler, W., *Nat. Rev. Gastroenterol. Hepatol.*, 2011, 8(8), 438-453; Hasler, W., et al., *Am. J. Gastroenerol.*, 2011, 106(8), 1492-1502; Jaffe, J. K., et al., *J. Clin Gastroenterol.*, 2011, 45(4), 317-321). Not only do the symptoms significantly affect QOL, but the clinical consequences can be serious. For example, once a patient develops protracted nausea and vomiting, providing adequate nutrition, hydration, and access to therapeutics can present a substantive challenge to clinicians (Parrish, C. R., *Gastroenterol. Clin. North Am.*, 2015, 44(1), 83-95). In addition, patients with diabetic gastroparesis may have increasing difficulty controlling blood glucose due to unpredictable gastric emptying and altered absorption of orally administered hypoglycemic and prokinetic drugs (Alam, U., et al., *Diabetes Ther.*, 2010, 1(1), 32-43; O'Donovan, D., et al., *Curr. Treat. Options Gastroenterol.*, 2003, 6(4), 299-309). Severe symptoms may cause complications such as malnutrition, dehydration, metabolic derangements, esophagitis, and Mallory-Weiss tears which can result from retching and vomiting (O'Donovan, D., et al., *Curr. Treat. Options Gastroenterol.*, 2003, 6(4), 299-309; Parrish, C. R., *Gastroenterol. Clin. North Am.*, 2015, 44(1), 83-95; Parkman, H. P., and Schwartz, S. S., *Arch. Intern. Med.*, 1987, 147(8), 1477-1480; Younes, Z., and Johnson, D. A., *J. Clin. Gastroenterol.*, 1999, 29(4), 306-317). There are many other examples of the health consequences of gastroparesis, including hospitalizations and morbidity.

Prior to the completion and analysis of DIGEST I, the data supported a dose-dependent improvement in symptom score going from 5 mg to 15 mg to 30 mg velusetrag, consistent with the objective gastric emptying seen in an early Phase 2a study. Thus, an important objective of the instant invention was to provide evidence of dose-dependent symptom relief as shown by patient-reported symptom score measured by the Gastroparesis Cardinal Symptom Index (GCSI) after 4 weeks of dosing, by Gastroparesis Rating Score (GRS) at 4 and 12 weeks, the Patient Assessment of Upper Gastrointestinal Symptom Severity Index (PAGI-SYM) and objective measurement of improved gastric emptying time. Symptoms measured in the clinical setting include, but are not limited to, nausea, bloating, postprandial fullness, early satiety, vomiting, upper abdominal pain, epigastric burning, gastric reflux with or without burning, and bowel movements. The patient reported outcomes for once-daily administration of velusetrag was monitored for 14 weeks at placebo, 5 mg velusetrag, 15 mg velusetrag, and 30 mg velusetrag, and the change from baseline in weekly GRS total score was evaluated over 14 weeks, with the last two weeks reflecting scores where the patient was off therapy.

Surprisingly, it has now been discovered that when velusetrag is used to treat gastroparesis in diabetic or idiopathic adult patients, symptom relief as reported by the patient is not correlated with increase motility.

Management goals for patients with gastroparesis include correction of the nutritional state, reduction in symptoms, improvement of gastric emptying, and in diabetics, achieving glycemic control (Camilleri, M., et al., *Am. J. Gastroenterol.*, 2013, 108(1), 18-37). There are limited safe and effective pharmacologic therapies for patients suffering from gastroparesis who do not respond to dietary changes and other non-pharmacologic options. Thus, with the current approaches and therapies, management goals are often unmet, and there is an urgent medical need for development of drugs with a favorable risk-benefit profile to treat patients with gastroparesis (FDA Draft Guidance, July 2015).

This invention presents an evaluation of the efficacy of velusetrag on symptoms in subjects with gastroparesis. Those symptoms include nausea, bloating, postprandial fullness, early satiety, vomiting, abdominal pain, epigastric burning, gastric reflux with or without burning, and bowel movements evaluated at different levels of gastric emptying. Patient reported outcomes were measured by psychometric properties of CGSI-24 H and GRS as discussed below.

Definition of Terms and Conventions Used

Throughout this specification and in the claims that follow, the following terms are defined with the following meanings, unless explicitly stated otherwise.

The singular forms "a," "an," and "the" include the corresponding plural forms unless the context of use clearly dictates otherwise.

The term "about" or "approximately" when used in the context of dosage amount is defined by a margin of error that is typically about twice the standard deviation or the half-width of a 95 percent confidence interval. The term "approximate" in other areas of the disclosure may be used to indicate standard deviation or the amount of variation or dispersion of a set of data values. All numbers expressing quantities herein are to be understood as being modified in all instances by the term "about," unless otherwise indicated. The term "about" or "approximately" when used in the context of dosage amount is typically±0.5 mg, preferably ±0.2 mg. Each number should be construed in light of the reported significant digits and by applying ordinary rounding techniques.

The terms "all symptoms" includes the following: nausea, bloating, postprandial fullness, early satiety, vomiting, abdominal pain, epigastric burning, gastric reflux with or without burning, and bowel movements. The terms "all symptoms" are defined as at least 3 of the total symptoms above, preferably 5 of the total symptoms, and most preferably 9 of the total symptoms.

The terms "comprising", "including," and "having" are intended to be inclusive and mean that there may be additional elements other than the listed elements.

Gastroparesis Cardinal Symptom Index (GCSI) is a patient reported outcome that measures 3 symptoms: (1) nausea/vomiting as a single symptom, (2) postprandial fullness/early satiety as one symptom; and (3) bloating, using up to 9 questions assessing the severity of each symptom domain.

Gastroparesis Rating Score is a patient reported outcome that measures 9 symptoms: (1) nausea, (2) bloating, (3) postprandial fullness, (4) early satiety, (5) vomiting, (6) abdominal pain, (7) epigastric burning, (8) gastric reflux with or without burning, and (9) bowel movements, using up to 27 questions assessing the severity of the symptom, the daily frequency of the symptom, the length of time on a daily basis of the symptom, and whether the symptom continues over a 24-hour period.

The term "human patient" includes pediatric, adolescent and adult patients.

Patient Assessment of Upper Gastrointestinal Symptom Severity Index (PAGI-SYM) is defined as a 2-week recall patient reported outcome that assesses gastroparesis, functional dyspepsia and gastro-esophageal reflux disease with 20 symptom severity items that cover the following symptoms: (1) nausea, (2) vomiting, (3) postprandial fullness, (4) early satiety, (5) bloating, (6) upper abdominal pain, (7) lower abdominal pain, (8) heartburn, and (9) regurgitation.

Gastric emptying and gastric emptying delay is defined using the following criteria based on the assessment used: gastric emptying half time (GE $t_{1/2}$), estimated time in which half the stomach contents are emptied after a test meal, exceeding 180 minutes for a 4-hour octanoic breathe test, percentage of solid meal retention in the stomach over 10% at hour 4 after a test meal for gastric emptying scintigraphy, rate of $^{13}CO_2$ excretion per minute after consumption of a test meal below the following thresholds, 12.9 at 45 minutes, 26.9 at 90 minutes, 34.4 at 12 minutes, 39.5 at 150 minutes, 43 at 180 minutes and 35 at 240 minutes, for the spirulina breath test.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). Pharmaceutically acceptable salts can be derived from pharmaceutically acceptable inorganic or organic bases and from pharmaceutically acceptable inorganic or organic acids. In addition, when a compound contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "treating" or "treatment" includes preventing, alleviating ameliorating, giving relief to symptoms associated to gastroparesis.

The term "unit dosage form" refers to a physically discrete unit suitable for dosing a patient, i.e., each unit containing a predetermined quantity of active agent calculated to produce the desired therapeutic effect either alone or in combination with one or more additional units.

Pharmaceutical Compositions and Formulations

The invention also relates to pharmaceutical compositions for use in the treatment of gastroparesis. The crystalline hydrochloride salt forms of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a crystalline hydrochloride salt of a compound of Formula I. Optionally, such pharmaceutical compositions may contain other therapeutic and/or formulating agents if desired.

The pharmaceutical compositions of the invention typically contain a therapeutically effective amount of a crystalline salt of the present invention. Typically, such pharmaceutical compositions will contain from about 0.1 to about 95% by weight of the active agent; including from about 1 to about 70% by weight, such as from about 5 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. For example, such unit dosage forms may be capsules, tablets, pills, and the like.

In a preferred embodiment, the pharmaceutical compositions of the invention are suitable for oral administration.

Suitable pharmaceutical compositions for oral administration may be in the form of capsules, tablets, pills, lozenges, cachets, sachets, stick-packs, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid, methacrylic acid ester, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

Formulation Example A

Hard gelatin capsules for oral administration are prepared as follows:

| Ingredients | Amount |
| --- | --- |
| Velusetrag salt | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

Formulation Example B

Hard gelatin capsules for oral administration are prepared as follows:

| Ingredients | Amount |
| --- | --- |
| Velusetrag salt | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

Formulation Example C

Capsules for oral administration are prepared as follows:

| Ingredients | Amount |
| --- | --- |
| Velusetrag salt | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

Formulation Example D

Tablets for oral administration are prepared as follows:

| Ingredients | Amount |
| --- | --- |
| Velusetrag salt | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60EC and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

Formulation Example E

Tablets for oral administration are prepared as follows:

| Ingredients | Amount |
| --- | --- |
| Velusetrag salt | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

Formulation Example F

Single-scored tablets for oral administration are prepared as follows:

| Ingredients | Amount |
| --- | --- |
| Velusetrag salt | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of composition per tablet).

Formulation Example G

A suspension for oral administration is prepared as follows:

| Ingredients | Amount |
| --- | --- |
| Velusetrag salt | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

Formulation Example H

A dry powder for administration by inhalation is prepared as follows:

| Ingredients | Amount |
| --- | --- |
| Velusetrag salt | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

Formulation Example I

A dry powder for administration by inhalation in a metered dose inhaler is prepared as follows:
Representative Procedure: A suspension containing 5 wt. % of a salt of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example J

An injectable formulation is prepared as follows:

| Ingredients | Amount |
| --- | --- |
| Velusetrag salt | 0.2 g |
| Sodium acetate buffer solution (0.4M) | 40 mL |
| HCl (0.5N) or NaOH (0.5N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Formulation Example K

Capsules for oral administration are prepared as follows:

| Ingredients | Amount |
| --- | --- |
| Velusetrag salt | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

Formulation Example L

Capsules for oral administration are prepared as follows:

| Ingredients | Amount |
| --- | --- |
| Velusetrag salt | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

Routes of Administration

The invention also relates to an acceptable route of administration of velusetrag to the human patient, including, but not limited to, oral, parenteral, buccal, sublingual, rectal, intraperitoneal, or endotracheal routes of administration. For example, parenteral administration may be by infusion, injection, or implantation. Parenteral may also include percutaneous administration via subcutaneous, intramuscular, intravenous, transdermal, or by implantation routes. If velusetrag is administered parenterally, it may be in the form of a liquid, solid or gel. Similarly, if velusetrag is administered orally, it may be in the form of a liquid, capsule, tablet, chewable tablet or dissolvable film.

The following examples are illustrative in purpose without limiting the scope of the invention described herein.

EXAMPLES AND EXPERIMENTAL 1.0 Clinical Study Materials
1.1 Preparation of Crystalline Velusetrag Hydrochloride Salt The preparation of velusetrag can be found in U.S. Pat. No. 7,375,114 B2 and velusetrag hydrochloride salt can be found in U.S. Pat. No. 7,728,004 B2. In a 1 L flask, 1-isopropyl-2-oxo-1,2-dihydroquinoline-3-carboxylic acid {(1S,3R,5R)-8-[(R)-2-hydroxy-3-(methanesulfonyl-methylamino)propyl]-8-aza-bicyclo[3.2.1]oct-3-yl}amide (34.7 g, 0.069 mol) was suspended in absolute ethanol (210 mL). Concentrated HCl (1.1 eq) was added at room temperature with stirring. The mixture was stirred at reflux for 30 min and cooled to room temperature and stirred for 2 h. The solid was filtered and the wet cake was washed with cold absolute ethanol (3×50 mL). The solid was dried under vacuum at 30° C. for 48 h to provide the title compound (34.5 g, 93.7% yield, water content by Karl Fischer method 0.13%) %).

1.2 Preparation of Crystalline Velusetrag Hydrochloride Salt Hydrate

The preparation of the hydrate of velusetrag hydrochloride salt can also be found in U.S. Pat. No. 7,728,004 B2. 1-Isopropyl-2-oxo-1,2-dihydroquinoline-3-carboxylic acid {(1S,3R,5R)-8-[(R)-2-hydroxy-3-(methanesulfonyl-methylamino)propyl]-8-aza-bicyclo[3.2.1]oct-3-yl}amide hydrochloride (139 mg, 0.28 mmol) was dissolved in sterilized water for injection (2 mL). Over a few hours, the solution became a cloudy suspension. The suspension was stirred and allowed to sit overnight at ambient temperature resulting in a white precipitate. The solid was collected by filtration and dried for 2 min at ambient conditions (approximately 40-50% relative humidity) to provide the title compound (130 mg, 91% yield).

1.3 Preparation of Formulations for Clinical Studies

The pharmaceutical composition tested in the clinical setting was a solid blend consisting essentially of drug substance (velusetrag HCl), hydroxypropyl methylcellulose, microcrystalline cellulose, lactose monohydrate, and magnesium stearate. Three blended formulations, each having 5 mg, 15 mg, or 30 mg velusetrag, were manufactured at Novast Lab.

The compositions of the blended formulations are shown in Table 1 below:

TABLE 1

Velusetrag, Blended Capsule Batch Formula for Strengths

| Ingredient | Weight (mg)/Capsule | | |
|---|---|---|---|
| Strength (FBE) | 5 mg | 15 mg | 30 mg |
| Velusetrag HCl Drug Substance[b] | 5.35 | 16.06 | 32.12 |
| Hydroxypropyl Methylcellulose | 6.25 | 6.25 | 6.25 |
| Microcrystalline Cellulose | 100 | 100 | 100 |
| Lactose Monohydrate[a] | 137.15 | 126.44 | 110.38 |
| Magnesium Stearate | 1.25 | 1.25 | 1.25 |
| Total | 250 | 250 | 250 |

[a]Excipient levels are adjusted to accommodate different dosage strengths.
[b]The velusetrag HCl salt weight is corrected for free base.

2.0 Clinical Studies
2.1 Phase 2a Study and Trial Results

A Phase 2a study was conducted as a multicenter, randomized, double-blind, placebo-controlled, incomplete 3-period fixed sequence crossover Phase 2 study evaluating the effects of velusetrag on gastric emptying (assessed by [$^{13}$C]-octanoate breath testing over a 4-hour period) in patients with diabetic (n=18) or idiopathic (n=16) gastroparesis. Velusetrag (5 mg [n=26], 15 mg [n=25], or 30 mg [n=25]) was administered once-daily in three, 1-week treatment periods, with a 1-week washout period between each treatment period. Randomized subjects required documentation of the symptoms of gastroparesis for at least 3 months prior to study entry. A key inclusion criterion for the study was the documentation of gastric emptying delay at screening. Delay is defined as gastric emptying half-time (GE $t_{1/2}$)>180 mins (the upper bound of the 95% confidence interval for healthy subjects) for the octanoate breathe test. Gastric emptying half-time is defined as the estimated time, through the gastric emptying curve, when half the stomach contents are considered to have been emptied.

On the intent-to-treat (ITT) population, including both idiopathic and diabetic gastroparesis subjects, the proportion of subjects with at least a clinically relevant 20% reduction from baseline at Day 7 in GE $t_{1/2}$ was numerically higher in all of the velusetrag treatment groups compared with placebo, achieving statistical significance (P=0.002) in the patients treated with velusetrag 30 mg (52% of subjects vs. 5% of subjects; velusetrag 30 mg and placebo, respectively). Velusetrag 5 mg and 15 mg numerically increased the proportion of subjects with a 20% reduction in GE $t_{1/2}$ from baseline to 26% and 20%, respectively, although neither increase was statistically significant.

The least squares (LS) mean absolute reduction, in minutes and percentage of baseline (%), in GE $t_{1/2}$ were reported as 13 mins (2%) for placebo and 35 mins (11%), 34 mins (8%), and 52 mins (21%) for velusetrag 5-, 15-, and 30-mg, respectively, which represent clinically relevant changes in gastric emptying for the velusetrag treatment groups, with the 30 mg dose being statistically significant.

Most adverse events (AEs) were mild in severity. The most frequent treatment-emergent AEs (TEAEs) were diarrhea, nausea, abdominal pain, constipation, flatulence, and headache. The majority of TEAEs were reported following velusetrag 5- and 15-mg, with one subject receiving velusetrag 5 mg withdrawing from the study due to mild diarrhea, dyspepsia, and nausea. Most AEs were reported during treatment with velusetrag 5- and 15-mg, but may have been due to desensitization related to administration of velusetrag 30 mg last in the treatment sequence.

All doses of velusetrag resulted in a reduction in the GE $t_{1/2}$ from baseline in both the diabetic and idiopathic gastroparesis subgroups. Larger reductions from baseline were observed in the diabetic gastroparesis subgroup compared to the idiopathic gastroparesis subgroup (39 mins, 47 mins, 72 mins for velusetrag 5-, 15-, and 30-mg for the diabetic gastroparesis subgroup and 26 mins, 15 mins, and 26 mins for velusetrag 5-, 15-, and 30-mg for the idiopathic gastroparesis subgroup, respectively).

The Phase 2a clinical study demonstrated that velusetrag accelerated gastric emptying in subjects with diabetic or idiopathic gastroparesis and was well tolerated in these populations. Patients receiving the 30 mg dose of velusetrag had the greatest amount of gastric emptying and least amount of AEs.

2.2 DIGEST I Study and Trial Results

DIGEST I was a global Phase 2b, 12-week, multicenter, randomized, double-blind, placebo-controlled, parallel 4-group study to evaluate 3 dose levels of velusetrag (5 mg, 15 mg, and 30 mg) compared to placebo when administered once daily for approximately 12 weeks in subjects with diabetic or idiopathic gastroparesis (GP). The total duration of study participation for each completed subject was approximately 19 weeks including:

Screening period: up to 5 weeks, including one week baseline period;

Treatment period: 12 weeks; and

Follow-up: 2 weeks.

Subject underwent assessment during the screening period to determine their eligibility for the study. These assessments included completion of several PRO measures, including the Patient Assessment of Upper Gastrointestinal Symptoms (PAGI-SYM) questionnaire (a 2-week recall instrument that included the Gastroparesis Cardinal Symptoms Index [GCSI, designated as GCSI-2W in this study] (Gastroparesis: Clinical Evaluation of drugs for treatment Guidance for Industry-July 2015) and the Screening Treatment Satisfaction Questionnaire, safety laboratory test, and electrocardiograms (ECGs). Subjects also underwent a gastric emptying test (either a 4-hour technetium-labelled Sulphur colloid [$^{99m}$Tc] gastric emptying scintigraphy [GES] or 4-hours $^{13}$C-spirulina Gastric Emptying Breath Test [GEBT] during the screening period unless the subjects had a comparable, qualifying gastric emptying test performed within one year of screening. The study was designed to have at least 50% of the subjects enrolled qualify for enrollment by a gastric emptying test performed during the screening period instead of relying on a qualifying historical test.

To qualify for entry into the Baseline Period of the study, subjects had to have: a) a composite score of 2 and <5 points on nausea, bloating, feeling excessively full after meals, and not able to finish a normal-sized meal on the GCS1-2W; b) a score of ≥3 points for at least 2 of these 4 symptoms on the GCS1-2W at Screening; and c) delayed gastric emptying as determined by either a 4-hour $^{99m}$Tc GES or GEBT. If a subject failed either the GES or GEBT at Screening, then a second gastric emptying test could have been performed during the Screening Period using the GEBT in order to qualify for the study. Subjects who were eligible for further study participation completed the 2 daily PRO measures (the Gastroparesis Rating Scale [GRS] and a daily version of the GCSI, designated the Gastroparesis Cardinal Symptoms Index—24-Hour Recall [GCS1-24H] in this study) over a 7-day period to establish baselines.

After the 1-week Baseline Period, subjects were required to have a 7-day mean score of ≥2.5 and <5 points on the GCS.1-24H at Day 1 to be eligible for entry. Eligible subjects completed the Patient Assessment of Upper Gastrointestinal Quality of Life (PAG1-QOL) questionnaire to establish baseline QOL metrics at Day 1. Subjects were then randomized in a 1:1:1:1 ratio to receive 1 of 3 dose levels of velusetrag or placebo; both study drugs were administered once daily in a double-blind manner for approximately 12 weeks.

During the treatment period, subjects were instructed to take 1 capsule of study drug once daily approximately 30 minutes prior to eating at approximately the same time each morning and to record the time of drug ingestion in the electronic diary. Subjects also completed the GCS1-24H and GRS on a daily basis using an electronic diary. At specified times, subjects also completed the PAG1-QOL questionnaire to assess QOL metrics and the Treatment Satisfaction Questionnaire. In addition, subjects and clinicians completed the Overall Treatment Effect (OTE) and Overall Gastroparesis Severity (OGS) instruments to serve as anchor instruments for the psychometric evaluation of the GRS measure. Subjects returned to the study center for safety and efficacy assessments as detailed in the Schedule of Study Procedures.

The primary objectives of the study were to evaluate the effect of velusetrag on the symptoms of gastroparesis and gastric emptying. Approximately half the patients were intended to be diabetic with the other half idiopathic gastroparetic.

A daily proprietary patient reported outcome (PRO) tool was used to assess GP symptoms, the Gastroparesis Rating Scale (GRS), developed according to the current FDA PRO guidance. The GRS covers the following cardinal symptom domains: (1) nausea, (2) vomiting, (3) postprandial fullness/early satiety, (4) bloating, (5) upper abdominal pain, (6) gastric reflux/burning, and (7) bowel movements. The GRS symptom domains may be also categorized or grouped into Factor 1 (fullness, early satiety, bloating, upper abdominal pain, and epigastric burning) and Factor 2 (nausea and vomiting).

Standard safety and tolerability monitoring was also evaluated. Specifically, velusetrag was studied in idiopathic and diabetic gastroparesis patients in order to evaluate: (1) the effect of oral velusetrag (5 mg, 15 mg and 30 mg), compared with placebo, administered once daily over a 12-week treatment period on symptoms in patients with either diabetic or idiopathic gastroparesis; (2) the effect of oral velusetrag (5 mg, 15 mg and 30 mg), compared with placebo on gastric emptying; and (3) the safety of oral velusetrag (5 mg, 15 mg and 30 mg), compared with placebo over 12 weeks of treatment.

All the Adverse Events (AEs) were assessed by the investigators and recorded in the eCRF, including the dates of onset and resolution, severity, relationship to study drug, outcome, and action taken with study drug.

Clinical severity was recorded and granted as follow:

Mild: awareness of sign or symptoms, but easily tolerated;

Moderate: discomfort sufficient to cause interference with usual activities; and Severe: Incapacitation with inability to work or perform usual activities.

All the subjects were permitted to continue regularly prescribed medications for treatment of preexisting medical conditions: proton pump inhibitors, serotonin (5-HT$_3$) antagonist, other antiemetics, benzodiazepine derivatives, propulsive, antipropulsive, diphenulmethane derivatives, H$_2$-receptor antagonists.

2.3 Study Population

A total of 233 patients were randomized to receive one of three doses of velusetrag (5 mg, 15 mg, or 30 mg) or placebo administered once-daily (QD) for 12 weeks in the morning with or without food as reported in Table 2.

TABLE 2

Study Population

| | Placebo (N = 59) | VEL 5 mg (N = 59) | VEL 15 mg (N = 57) | VEL 30 mg (N = 58) | Total (N = 233) |
|---|---|---|---|---|---|
| Subjects Randomized, n (%) | 59 (100.00) | 59 (100.0) | 57 (100.0) | 58 (100.0) | 233 (100.0) |
| Subjects Randomized and Treated with Study Drug, n (%) | 59 (100.0) | 59 (100.0) | 56 (98.2) | 58 (100.0) | 232 (99.6) |
| Subjects Randomized but Not Treated, n (%) | 0 | 0 | 1 (1.8) | 0 | 1 (0.4) |
| Subjects Who Completed Study Treatment Period, n (%) | 50 (84.7) | 49 (83.1) | 44 (77.2) | 51 (87.9) | 194 (83.3) |
| Subjects Who Did Not Complete Study Treatment Period, n (%) | 9 (15.3) | 10 (16.9) | 12 (21.1) | 7 (12.1) | 38 (16.3) |
| Adverse Event | 5 (8.5) | 2 (3.4) | 6 (10.5) | 4 (6.9) | 17 (7.3) |
| Lost to Follow-Up | 0 | 1 (1.7) | 0 | 0 | 1 (0.4) |
| Physician Decision | 1 (1.7) | 0 | 1 (18) | 1 (1.7) | 3 (1.3) |
| Withdrawal by Subject | 3 (5.1) | 7 (11.9) | 5 (8.8) | 1 (1.7) | 16 (6.9) |
| Other | 0 | 0 | 0 | 1 (1.7) | 1 (0.4) |

TABLE 3

Key Demographic and Clinical Characteristics

| | Placebo (N = 59) | VEL 5 mg (N = 59) | VEL 15 mg (N = 53) | VEL 30 mg (N = 57) | Total (N = 228) |
|---|---|---|---|---|---|
| Age, mean (SD) | 47.0 (13.91) | 51.8 (13.29) | 50.2 (14.28) | 52.2 (12.01) | 50.3 (13.46) |
| Sex (female), n (%) | 43 (72.9) | 46 (78.0) | 42 (79.2) | 48 (84.2) | 179 (78.5) |
| Race (white), n (%) | 53 (89.8) | 52 (88.1) | 44 (83.0) | 52 (91.2) | 201 (88.2) |
| BMI, mean (SD) | 28.9 (6.80) | 29.9 (6.27) | 30.3 (5.52) | 28.9 (5.26) | 29.5 (6.00) |
| Gastroparesis Type (diabetic), n (%) | 32 (54.2) | 30 (50.8) | 29 (54.7) | 26 (45.6) | 117 (51.3) |
| GES Hour 4 Retention, mean (SD) | 32.8 (20.68) | 28.5 (17.93) | 38.7 (21.27) | 29.7 (14.59) | 32.5 (19.17) |
| HbA1c level (Diabetics), mean (SD) | 7.7 (1.47) | 6.9 (1.25) | 7.4 (1.57) | 6.9 (1.30) | 7.3 (1.43) |
| Baseline Weekly GCSI 24 H, mean (SD) | 3.0 (0.40) | 3.1 (0.54) | 3.1 (0.48) | 3.3 (0.59) | 3.1 (0.51) |
| Baseline Weekly Factor 1, mean (SD) | 2.7 (0.53) | 2.8 (0.52) | 2.7 (0.50) | 2.9 (0.54) | 2.7 (0.52) |
| Baseline Weekly Factor 2, mean (SD) | 1.6 (0.54) | 1.6 (0.69) | 1.6 (0.70) | 1.7 (0.66) | 1.6 (0.65) |

The highest baseline symptom scores were for postprandial fullness/early satiety and bloating with mean scores in the 3.6-3.7 points range. The nausea and/or vomiting subscale(s) was the lowest in severity with a mean of 1.7 to 2.1 points. The GCSI-24H did not have a pain subscale as the original GCSI-2 week recall PRO did not include a pain question. The baseline upper abdominal pain sub score was derived from the GRS PRO with a mean (SD) score of 3.3 (0.96) points.

TABLE 4

Baseline Symptom Scores for GCSI-24 and GRS PROs (ITT Population)

| Group | Baseline Score | GCSI | GRS |
|---|---|---|---|
| ITT (n = 228) | Total Score[1], mean (SD) | 3.1 (0.51) | 2.7 (0.52)/1.6 (0.65) |
| | Nausea/Vomiting[2], mean (SD) | 1.9 (0.97) | 2.5 (0.83)/0.7 (0.72) |
| | Fullness/Early Satiety, mean (SD) | 3.7 (0.59) | 3.2 (0.55) |
| | Bloating, mean (SD) | 3.7 (0.81) | 2.9 (0.72) |
| | Upper Abdominal Pain | — | 2.7 (0.77) |
| | Burning | — | 2.2 (0.92) |
| Diabetic (n = 117) | Total Score, mean (SD) | 3.1 (0.51) | 2.7 (0.51)/1.7 (0.67) |
| | Nausea/Vomiting[2], mean (SD) | 2.1 (0.96) | 2.5 (0.80)/0.9 (0.78) |
| | Fullness/Early Satiety, mean (SD) | 3.6 (0.57) | 3.1 (0.55) |
| | Bloating, mean (SD) | 3.7 (0.73) | 2.8 (0.67) |
| | Upper Abdominal Pain | — | 2.6 (0.76) |
| | Burning | — | 2.3 (0.87) |
| Idiopathic (n = 111) | Total Score, mean (SD) | 3.1 (0.51) | 2.8 (0.54)/1.5 (0.61) |
| | Nausea/Vomiting[2], mean (SD) | 1.8 (0.96) | 2.5 (0.86)/0.6 (0.61) |
| | Fullness/Early Satiety, mean (SD) | 3.8 (0.59) | 3.3 (0.54) |
| | Bloating, mean (SD) | 3.7 (0.89) | 2.9 (0.78) |
| | Upper Abdominal Pain | — | 2.7 (0.79) |
| | Burning | — | 2.2 (0.97) |

[1]total score for GRS is Factor 1 score/Factor 2 score 2.4 Changes in Symptoms by GCSI-24 H Total Score A total score was used to assess the GCSI PRO, which comprised a mean of 3 means symptoms domain score. The LS mean GCSI-24 H total score and changes from baseline are summarized in Table 5.

TABLE 5

Summary Least Square Mean Change from baseline and placebo of Weekly GCSI-24 H Total Score (ITT Analysis Set)

|  | Placebo (N = 59) | VEL 5 mg (N = 59) | VEL 15 mg (N = 53) | VEL 30 mg (N = 57) |
| --- | --- | --- | --- | --- |
| Week 4 Change from Baseline GCSI-24 H Total Score | | | | |
| LS Mean (SE) | −1.1 (0.13) | −1.5 (0.13) | −1.2 (0.14) | −1.0 (0.13) |
| LS Mean Difference (SE) | — | −0.4 (0.18) | −0.1 (0.19) | 0.1 (0.19) |
| 95% CI for LS Mean Difference | — | −0.75, −0.03 | −0.48, 0.27 | −0.29 (0.45) |
| p-value vs. Placebo | — | 0.0327 | 0.5758 | 0.6743 |
| Hochberg Adjusted p-value vs. Placebo | — | 0.0980 | 0.6743 | 0.6743 |
| Week 8 Change from Baseline GCSI-24 Total Score | | | | |
| LS Mean (SE) | −1.3 (0.14) | −1.6 (0.14) | −1.3 (0.15) | −1.3 (0.14) |
| LS Mean Difference (SE) | — | −0.3 (0.20) | −0.1 (0.21) | −0.0 (0.20) |
| 95% CI for LS Mean Difference | — | −0.71, 0.07 | −0.48, 0.34 | −0.43, 0.37 |
| p-value vs. Placebo | — | 0.1067 | 0.7323 | 0.8948 |
| Week 12 Change from Baseline GCSI-24 H Total Score | | | | |
| LS Mean (SE) | −1.4 (0.15) | −1.7 (0.15) | −1.4 (0.16) | −1.5 (0.15) |
| LS Mean Difference (SE) | — | −0.3 (0.21) | −0.0 (0.22) | −0.1 (0.22) |
| 95% CI for LS Mean Difference | — | −0.73, 0.10 | −0.44, 0.42 | −0.49, 0.36 |
| p-value vs. Placebo | — | 0.1331 | 0.9676 | 0.7683 |

A reverse dose response is observed in the Week 4 GCSI-24H total score with larger treatment effects observed with 5 mg dose group compared to 15 mg and 30 mg dose groups. Velusetrag 5 mg showed nominally statistically significant differences (reductions signifying improvements) in the Week 4 GCSI-24H total score of −0.4 points (95% CI: −0.75, −0.03, −0.03; p=0.0327) compared to placebo for the ITT analysis set. After multiplicity adjustment, no statistically significance was observed after Week 4 for the GCSI-24H. The trend for symptom improvement in all groups, including placebo, continued past Week 4 and stabilized starting from Week 6 to Week 8 through End of treatment at Week 12. A clear separation in symptoms total score was observed with the 5 mg velusetrag group relative to the 2 higher doses and the placebo group through the full 12 weeks of treatment (FIG. 1).

Initial analysis of a 3-factor model was based on the 3 domains: nausea/vomiting (Q1: nausea, Q2: retching, Q3: vomiting), postprandial fullness/early satiety (Q4: stomach fullness, Q5: not able to finish a normal sized meal, Q6: excessively full, Q7: loss appetite), and bloating (Q8: bloating and Q9 stomach feels larger).

Each individual domain was evaluated. No evidence of tachyphylaxis or diminution of effects was observed over the 12 weeks of treatment. FIGS. 2-8 show the results demonstrating the efficacy of velusetrag versus placebo administration in reducing and alleviating the symptoms associated with gastroparesis by GCSI-24H total score. LS Mean Differences in each subgroup are calculated based on repeated measures mixed effect model with change from baseline in weekly GCSI-24H total score as dependent variable, treatment, gastroparesis type (diabetic vs. idiopathic), GE test time (historical vs. prospective), baseline GCSI 24H total score, time, subgroup variable, interaction effect of treatment by time, baseline GCSI 24H total score by time, treatment by subgroup variable, time by subgroup variable and treatment by time by subgroup variable as fixed effect, a random effect of subject within site, using an unstructured covariance structure. For GCSI baseline subgroup analysis, baseline 24H total score is replaced with GCSI baseline categorical variable.

FIGS. 9-16 show the results of velusetrag administration versus placebo in reducing and alleviating the symptoms associated with gastroparesis by GCSI-24H responder Odds Ratio. These results demonstrate the efficacy of velusetrag administration. The responder is intended to decrease of at least 1 point from baseline. Odd ratios in each subgroup are calculated based on logistic repeated measures mixed effect model using binomial distribution with responders (Y/N) in weekly GCSI-24H total score as dependent variable, treatment, gastroparesis type (diabetic vs. idiopathic), GE test time (historical vs. prospective), baseline GCSI 24H total score, time, subgroup variable, interaction effect of treatment by time, baseline GCSI 24H total score by time, treatment by subgroup variable, time by subgroup variable and treatment by time by subgroup variable as fixed effect, a random effect of subject within site, using an autoregressive covariance structure. For GCSI baseline subgroup analysis, baseline 24H total score is replaced with GCSI baseline categorical variable. Nominal p-value are reported without multiplicity adjustment.

2.4a Efficacy of Velusetrag at Different Daily Dosage in Idiopathic and Diabetic Patients Compared with Placebo Tables 6 and 7 report the Least Squares Mean Change from baseline and placebo at Weeks 4, 8 and 14 GCSI-24 Total Score in idiopathic subgroup and diabetic subgroups.

TABLE 6

Summary of Least Squares Mean Change from Baseline and Placebo
in Weekly GCSI-24 H Total Score in Idiopathic Patients

|  | Placebo (N = 28) | VEL 5 mg (N = 29) | VEL 15 mg (N = 24) | VEL 30 mg (N = 31) |
|---|---|---|---|---|
| Week 4 | | | | |
| LS Mean (SE) | −0.9 (0.19) | −1.5 (0.18) | −1.2 (0.20) | −1.0 (0.18) |
| LS Mean Difference (SE) | — | −0.6 (0.26) | −0.3 (0.28) | −0.1 (0.26) |
| 95% CI for LS Mean Difference | — | −1.08 −0.05 | −0.82 0.27 | −0.59 0.45 |
| P-value vs. Placebo | — | 0.0319 | 0.3254 | 0.7910 |
| Week 8 | | | | |
| LS Mean (SE) | −1.0 (0.21) | −1.6 (0.20) | −1.5 (0.22) | −1.3 0.20) |
| LS Mean Difference (SE) | — | −0.6 (0.28) | −0.4 (0.30) | −0.2 (0.29) |
| 95% CI for LS Mean Difference | — | −1.11 0.01 | −1.00 0.19 | −0.78 0.35 |
| P-value vs. Placebo | — | 0.0546 | 0.1784 | 0.4556 |
| Week 12 | | | | |
| LS Mean (SE) | −1.1 (0.22) | −1.7 (0.21) | −1.5 (0.24) | −1.3 (0.21) |
| LS Mean Difference (SE) | — | −0.6 (0.30) | −0.4 (0.32) | −0.2 (0.30) |
| 95% CI for LS Mean Difference | — | −1.19 0.00 | −1.02 0.25 | −0.79 0.41 |
| P-value vs. Placebo | — | 0.0503 | 0.2292 | 0.5266 |
| Week 14 | | | | |
| LS Mean (SE) | −1.0 (0.21) | −1.4 (0.21) | −1.2 (0.23) | −1.0 (0.20) |
| LS Mean Difference (SE) | — | −0.4 (0.30) | −0.1 (0.31) | 0.0 (0.29) |
| 95% CI for LS Mean Difference | — | −1.01 0.15 | −0.76 0.47 | −0.59 0.57 |
| P-value vs. Placebo | — | 0.1488 | 0.6381 | 0.9833 |

TABLE 7

Summary of Least Squares Mean Change from Baseline and Placebo
in Weekly GCSI-24 H Total Score in Diabetic Patients

|  | Placebo (N = 31) | VEL 5 mg (N = 30) | VEL 15 mg (N = 29) | VEL 30 mg (N = 26) |
|---|---|---|---|---|
| Week 4 | | | | |
| LS Mean (SE) | −1.3 (0.18) | −1.5 (0.18) | −1.2 (0.18) | −1.0 (0.19) |
| LS Mean Difference (SE) | — | −0.2 (0.25) | 0.1 (0.25) | 0.2 (0.26) |
| 95% CI for LS Mean Difference | — | −0.71 0.28 | −0.44 0.56 | −0.29 0.74 |
| P-value vs. Placebo | — | 0.3926 | 0.8013 | 0.3851 |
| Week 8 | | | | |
| LS Mean (SE) | −1.5 (0.20) | −1.6 (0.19) | −1.2 (0.20) | −1.3 (0.21) |
| LS Mean Difference (SE) | — | −0.1 (0.27) | 0.3 (0.28) | 0.2 (0.28) |
| 95% CI for LS Mean Difference | — | −0.63 0.45 | −0.29 0.82 | −0.40 0.72 |
| P-value vs. Placebo | — | 0.7429 | 0.3412 | 0.5741 |
| Week 12 | | | | |
| LS Mean (SE) | −1.7 (0.21) | −1.7 (0.21) | −1.3 (0.22) | −1.6 (0.22) |
| LS Mean Difference (SE) | — | −0.0 (0.29) | 0.4 (0.30) | 0.1 (0.30) |
| 95% CI for LS Mean Difference | — | −0.62 0.54 | −0.22 0.96 | −0.53 0.66 |
| P-value vs. Placebo | — | 0.8940 | 0.2202 | 0.8309 |
| Week 14 | | | | |
| LS Mean (SE) | −1.6 (0.20) | −1.7 (0.20) | −1.1 (0.22) | −1.7 (0.22) |
| LS Mean Difference (SE) | — | −0.2 (0.29) | 0.4 (0.30) | −0.1 (0.30) |
| 95% CI for LS Mean Difference | — | −0.75 0.38 | −0.14 1.02 | −0.69 0.48 |
| P-value vs. Placebo | — | 0.5219 | 0.1369 | 0.7236 |

2.5 Psychometric Evaluation of GCSl-24H

Of the 232 subjects who were evaluable for analysis of the GCS1-24H, 2 subjects had missing data and were excluded from analyses. Therefore, a total of 230 subjects were included in the analyses.

Initial analyses of a 3-factor model were based on the 3 domains: nausea/vomiting (01: Nausea, 02: Retching, 03: Vomiting), postprandial fullness/early satiety (04: Stomach Fullness, 05: Not Able to Finish a Normal Sized Meal, 06: Excessively Full, 07: Loss Appetite), and bloating (08: Bloating and 09: Stomach Feels Larger). The 3-factor model had poor fit statistics and included a root mean square error of approximation (RMSEA)=0.150, comparative fit index (CFI)/nonnormed fit index (NNFI)=0.844/0.767, and standardized root mean square residual (SRMR)=0.098. However, these fit statistics improved considerably with the addition of residual correlations of 05 with 06 and 05 with 07 (RMSEA=0.071; CFI/NNFI=0.968/0.948; SRMR 0.069) (Table 8).

The higher order model was also not computable with no convergence even with iterations at 200,000.

Lastly, each of the individual domains by themselves were evaluated. All of these final domain models obtained good fit.

Table 9 provides the summary of the fit statistics for each of the domain-level models. Fit statistics for nausea/vomiting were as follows: RMSEA=<0.001 and CFI/NNFI=1.000. The correlation for Q2 Retching and Q3 Vomiting in this domain was 0.920. Due to the near-perfect fit of the model and the high correlation between the 2 items, another model was evaluated for the nausea/vomiting domain by adding postprandial fullness/early satiety and this demonstrated appropriate fit. Postprandial fullness/early satiety had good fit once residual correlation was included. Because estimated confirmatory factor analysis (CFA) models with only 2 items per domain were troublesome, bloating and postprandial fullness/early satiety were assessed in a single model in order to gain the added strength of the additional items.

TABLE 9

GCSl-24 H CFA Fit Statistics for Each Domain

| Model | CFI | NNFI | SRMR | RMSEA | RMSEA 90% CI |
|---|---|---|---|---|---|
| Nausea/Vomiting | 1.000 | 1.000 | <0.001 | <0.001 | <0.001-<0.001 |
| Nausea/Vomiting with Postprandial Fullness/Early Satiety: Residual correlation of Q4 Stomach Fullness with Q6 Excessively full | 0.977 | 0.959 | 0.060 | 0.068 | 0.029-0.106 |
| Postprandial Fullness/Early Satiety: Residual correlation of Q4 Stomach Fullness with Q6 Excessively Full | 1.000 | 1.015 | 0.003 | <0.001 | 0.000-0.126 |
| Postprandial Fullness/Early Satiety and Bloating: Residual correlation of Q5 Not able to finish mean with Q7 Loss of appetite; Q4 Stomach Fullness with Q6 Excessively Full | 0.984 | 0.959 | 0.044 | 0.087 | 0.038-0.139 |

Abbreviation: CFA, confirmatory factor analysis; CFI, comparative fit index; CI, confidence interval; GCSI-24 H, Gastroparesis Cardinal Symptoms Index 24-H Recall; NNFI, nonnormed fit index; RMSE, room mean square error of approximation; SRMR, standardized root mean square residual.

TABLE 8

GCSl-24 H Analyses of 3-Factor Model

|  |  |  |  | RMSEA | RMSEA 90% CI |
|---|---|---|---|---|---|
| GCSI: 3-factor | 0.844 | 0.767 | 0.098 | 0.150 | 0.127-0.174 |
| GCSI: 3-factor: Residual correlation Q5 Not able to finish meal with Q6 Excessively full; Q5 | 0.968 | 0.948 | 0.069 | 0.071 | 0.043-0.099 |

Abbreviations: CFI, comparative fit index; CI, confidence interval; GCSI-24 H, Gastroparesis Cardinal Symptoms Index - 24-Hour Recall; NNFI, non-normed fit index; RMSEA, room mean square error of approximation; SRMR, standardized root mean square residual.

The validity of the total score of the 3 factors was evaluated using 3 methods: bifactor model, higher order model, and by using domain scores as manifest variables and a latent total score as the single independent latent variable.

The bifactor model was not computable with errors that stated the standard errors of the model parameter estimates could not be computed.

2.6 Change of Symptoms by GRS –24 H Total Score

The primary endpoint evaluation time point was Week 4 with sensitivity analyses conducted at Weeks 8 and 12. Secondary endpoints at 12 weeks were chosen to evaluate the persistence and/or tachiphylaxis of treatment effect.

An inverse dose response pattern was observed with all 3 doses of velusetrag and in the daily symptom PRO where the 5 mg doses showed larger and more consistent symptom improvements versus the two higher doses. This is unexpected given the dose response observed in gastric emptying which is the central attribute which defines gastroparesis.

Velusetrag doses of 5 mg showed statistically nominally significant differences in the Week 4 GRS total score of –0.4 points (95% CI –0.71, –0.07; p=0.0159) compared with placebo for the ITT population with a similar treatment effect and nominal statistical significance at Week 12 (end of treatment) (Table 10).

These symptom changes with velusetrag 5 mg are notable at a patient level and represent a greater than 1 to 1.5 point change in level of symptom severity, from severe symptoms to moderate symptoms, from moderate to mild symptoms.

TABLE 10

Summary of LS mean change from baseline and placebo in Weekly GRS total score (ITT population)

|  | Placebo (N = 59) | Velusetrag 5 mg (N = 59) | Velusetrag 15 mg (N = 53) | Velusetrag 30 mg (N = 57) |
|---|---|---|---|---|
| Week 4 Change from Baseline GRS 24 H Total Score | | | | |
| LS Mean (SE) | −0.9 (0.12) | −1.3 (0.11) | −1.1 (0.12) | −0.8 (0.12) |
| LS Mean Difference (SE) | | −0.4 (0.16) | −0.2 (0.17) | 0.0 (0.17) |
| 95% CI for LS Mean Difference | | −0.71, −0.07 | −0.58, 0.08 | −0.28, 0.37 |
| P-value vs. Placebo | | 0.0159 | 0.1354 | 0.7981 |
| Week 8 Change from Baseline GRS 24 H Total Score | | | | |
| LS Mean (SE) | −1.1 (0.13) | −1.4 (0.13) | −1.2 (0.14) | −1.1 (0.13) |
| LS Mean Difference (SE) | | −0.3 (0.18) | −0.1 (0.19) | −0.1 (0.19) |
| 95% CI for LS Mean Difference | | −0.65, 0.06 | −0.49, 0.25 | −0.44, 0.29 |
| P-value vs. Placebo | | 0.1054 | 0.5221 | 0.6927 |
| Week 12 Change from Baseline GRS 24 H Total Score | | | | |
| LS Mean (SE) | −1.1 (0.13) | −1.5 (0.13) | −1.3 (0.14) | −1.3 (0.13) |
| LS Mean Difference (SE) | | −0.4 (0.18) | −0.2 (0.19) | −0.1 (0.19) |
| 95% CI for LS Mean Difference | | −0.74, −0.01 | −0.54, 0.21 | −0.49, 0.26 |
| P-value vs. Placebo | | 0.0427 | 0.3896 | 0.5344 |

Figure 17:
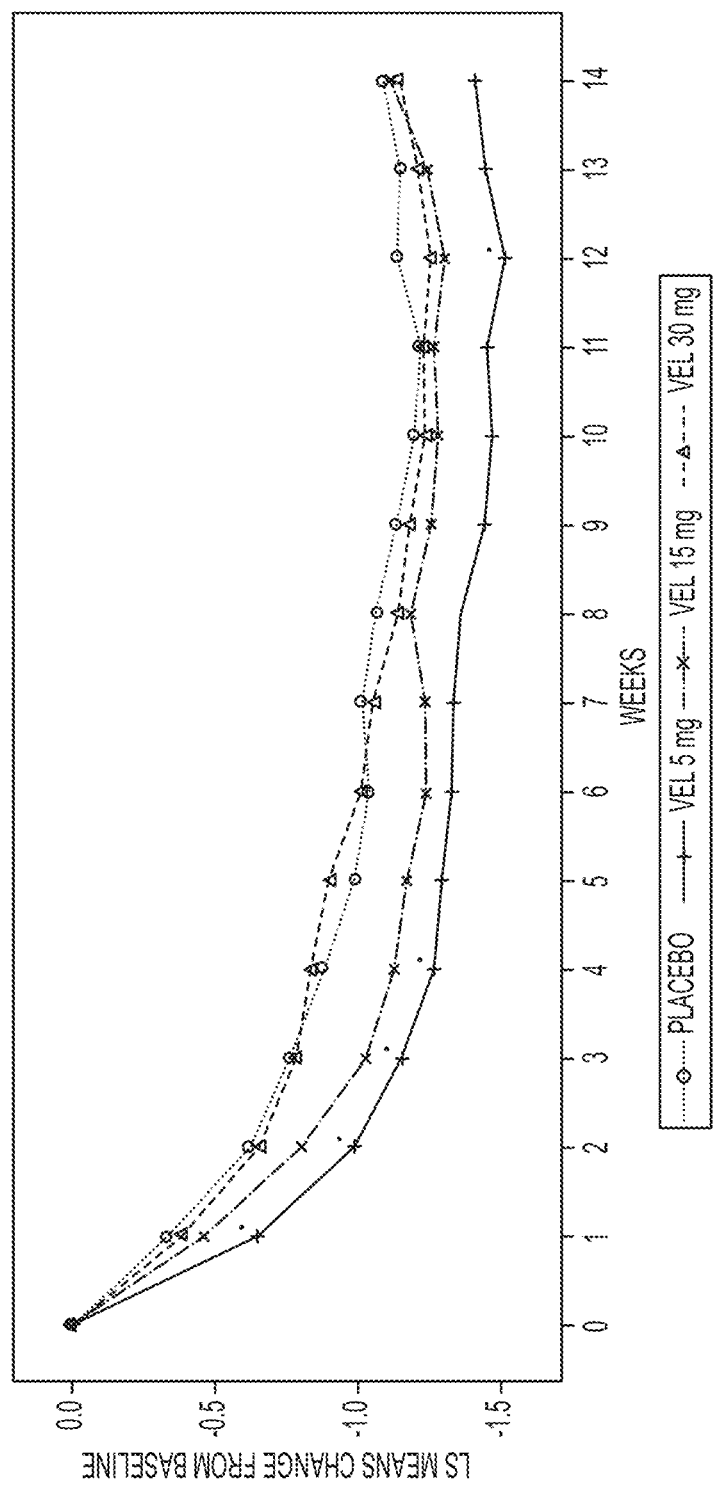
FIG. 17 illustrates the least square (LS) mean change from baseline in weekly GRS total score over 14 weeks for placebo, and 5 mg, 15 mg, and 30 mg velusetrag. LS means was calculated based on repeated measures mixed effect model with change from baseline in weekly GRS total score as dependent variable, treatment, gastroparesis type (diabetic vs. idiopathic), GE test time (historical vs. prospective), baseline GRS total score, time (categorical), interaction effect of treatment by time, baseline GRS total score by time, treatment by gastroparesis type and treatment by time by gastroparesis type as fixed effect, a random effect of subject within site, using an unstructured covariance structure. The asterisks on the 5 mg data set identify those data points that are significant from placebo in change from baseline nominal p-value <0.05.
Figure 18A:
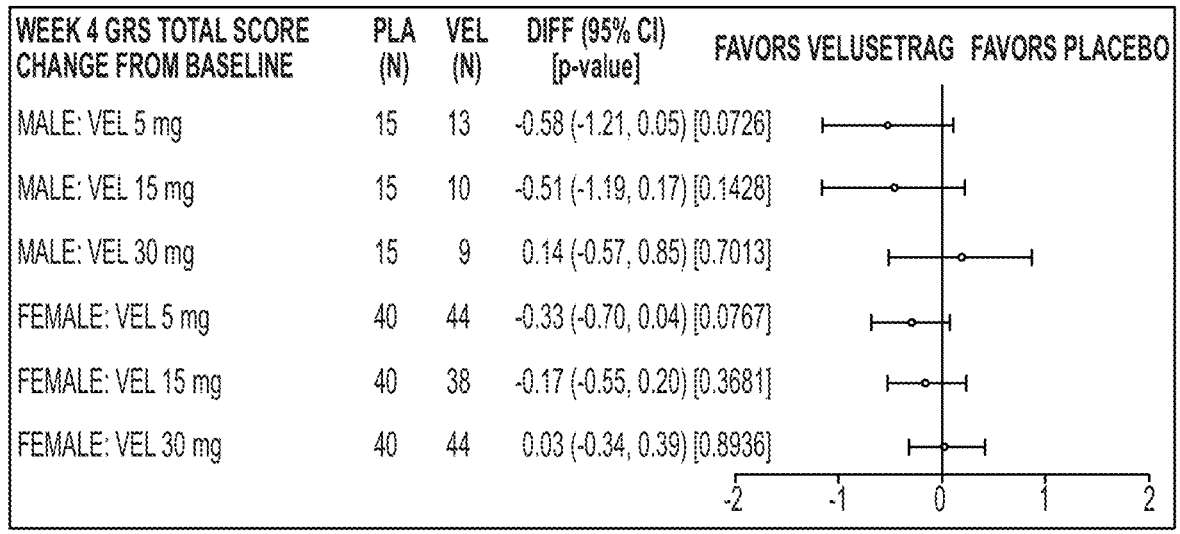
FIG. 18A illustrates GRS Total score by Sex at 4 weeks.
Figure 18B:
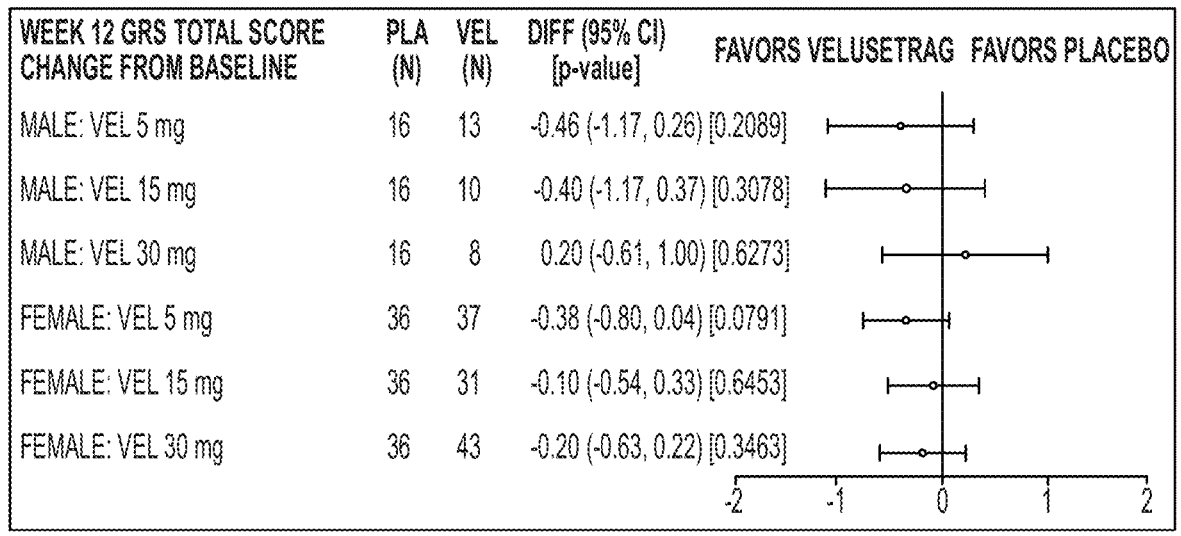
FIG. 18B illustrates GRS Total score by Sex at 12 weeks.
Figure 19A:
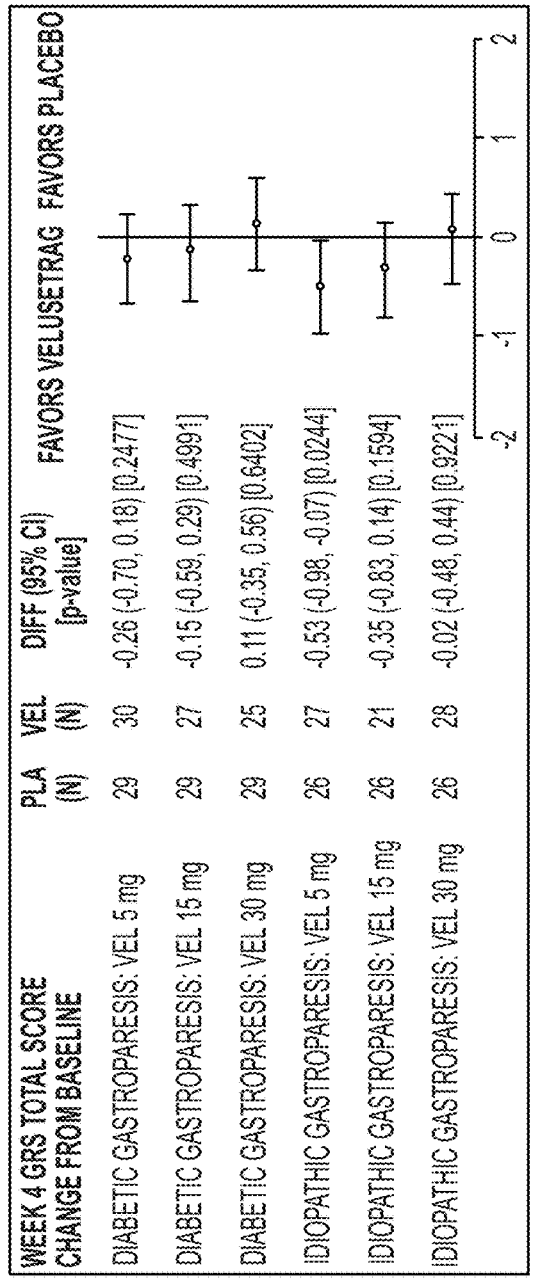
FIG. 19A illustrates GRS Total score by Gastroparesis Type at 4 weeks.
Figure 19B:
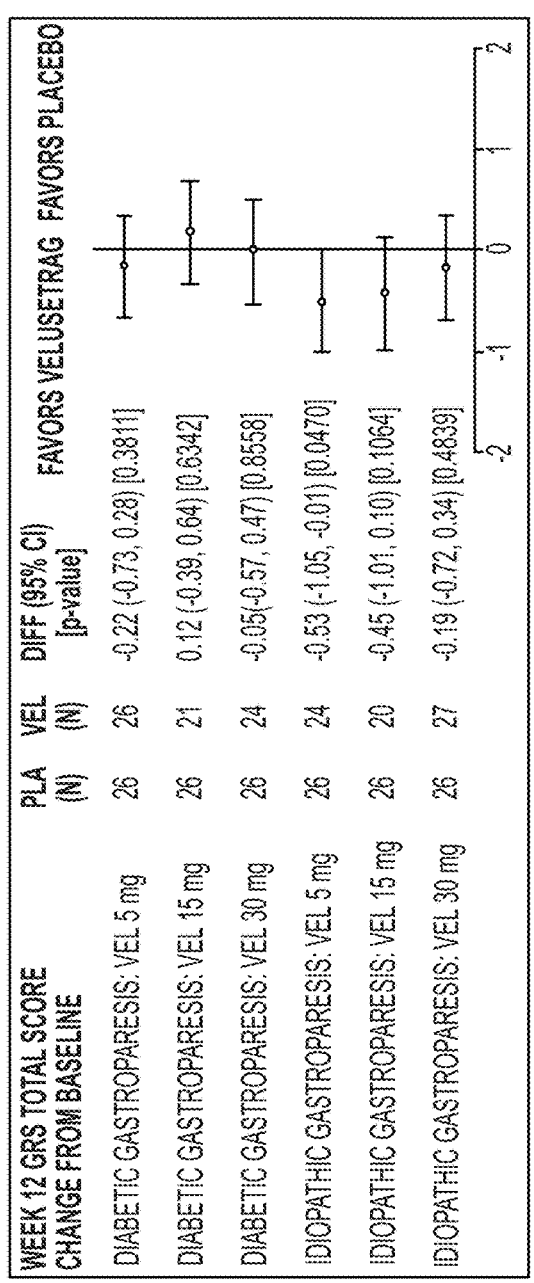
FIG. 19B illustrates GRS Total score by Gastroparesis Type at 12 weeks.
Figure 20A:
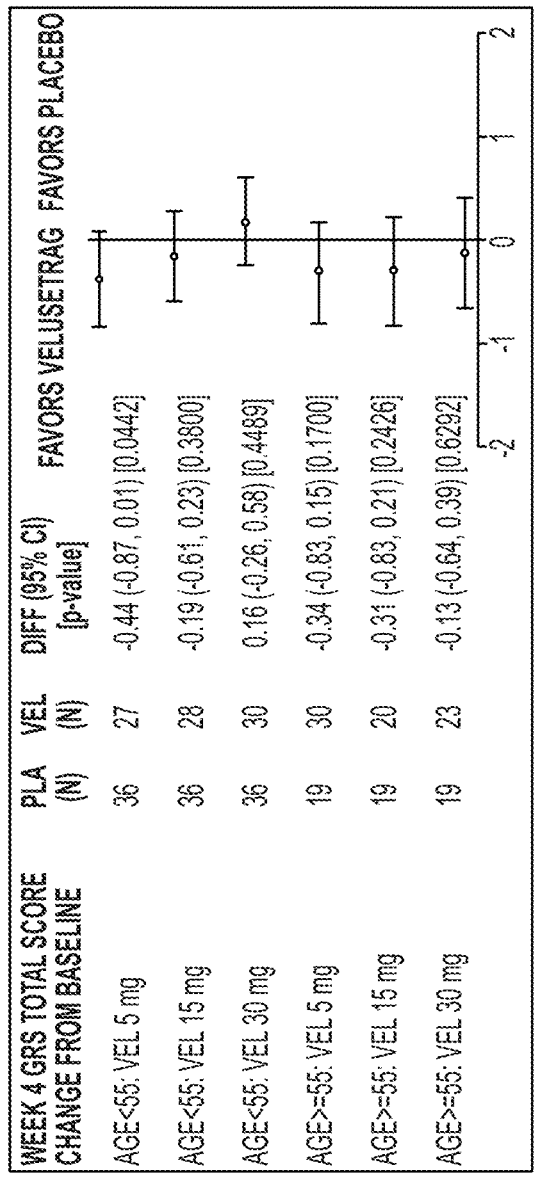
FIG. 20A illustrates GRS Total score by Age at 4 weeks.
Figure 20B:
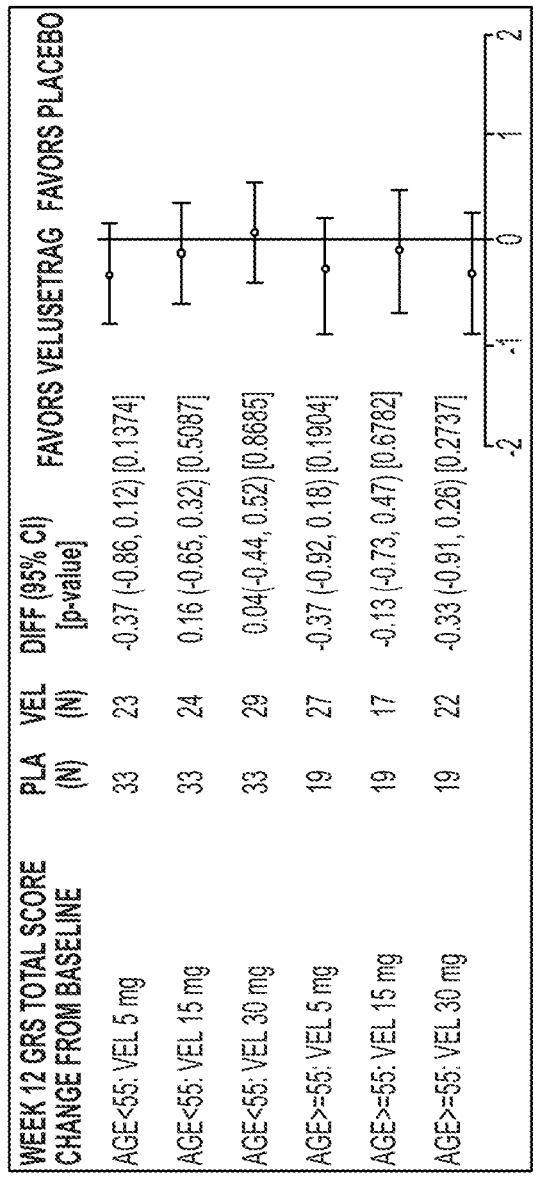
FIG. 20B illustrates GRS Total score by Age at 12 weeks.
Figure 22A:
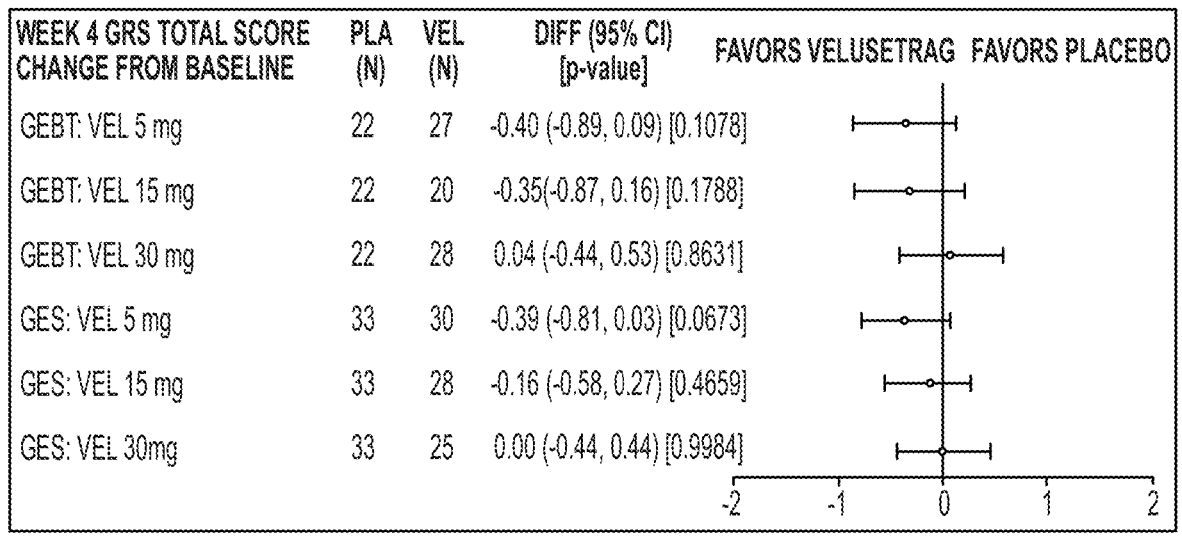
FIG. 22A illustrates GRS Total Score by type of Gastric Emptying Screening Test at 4 weeks.
Figure 22B:
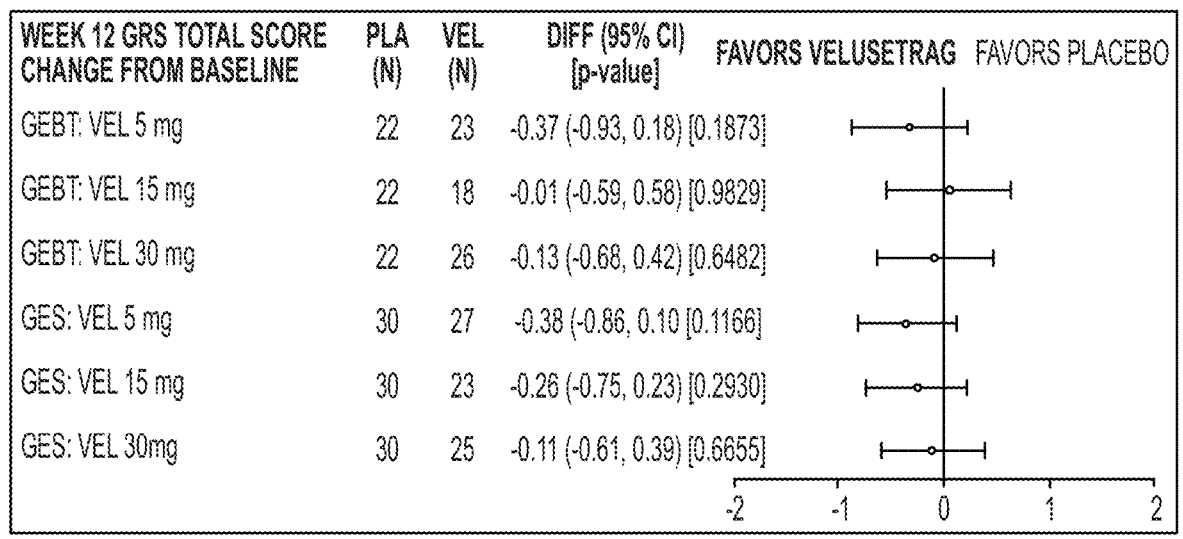
FIG. 22B illustrates GRS Total Score by type of Gastric Emptying Screening Test at 12 weeks.
Figure 24A:
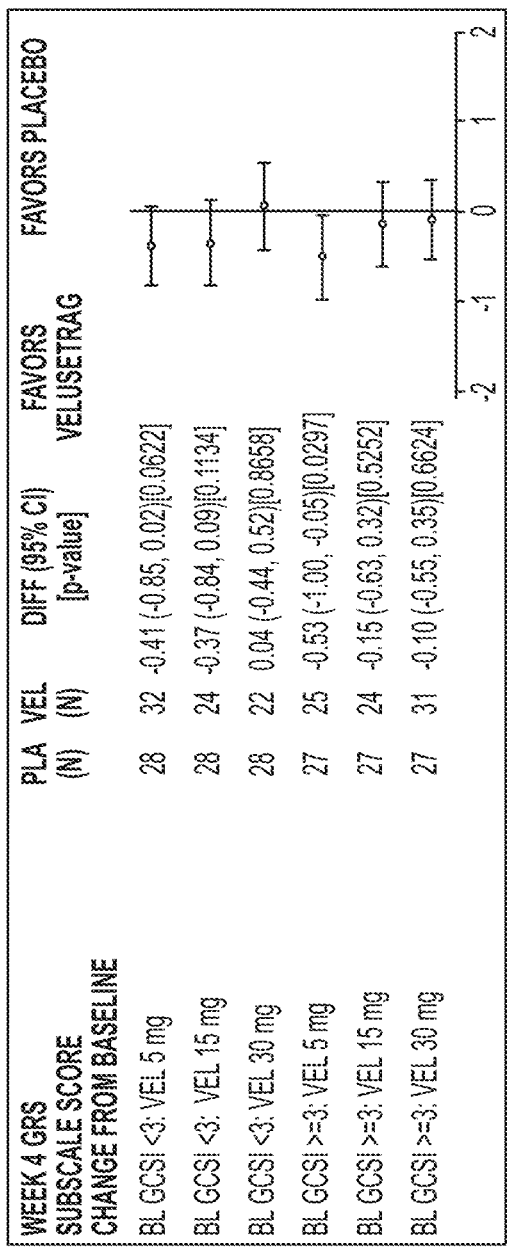
FIG. 24A illustrates GRS Total Score by Baseline Total score at 4 weeks.
Figure 24B:
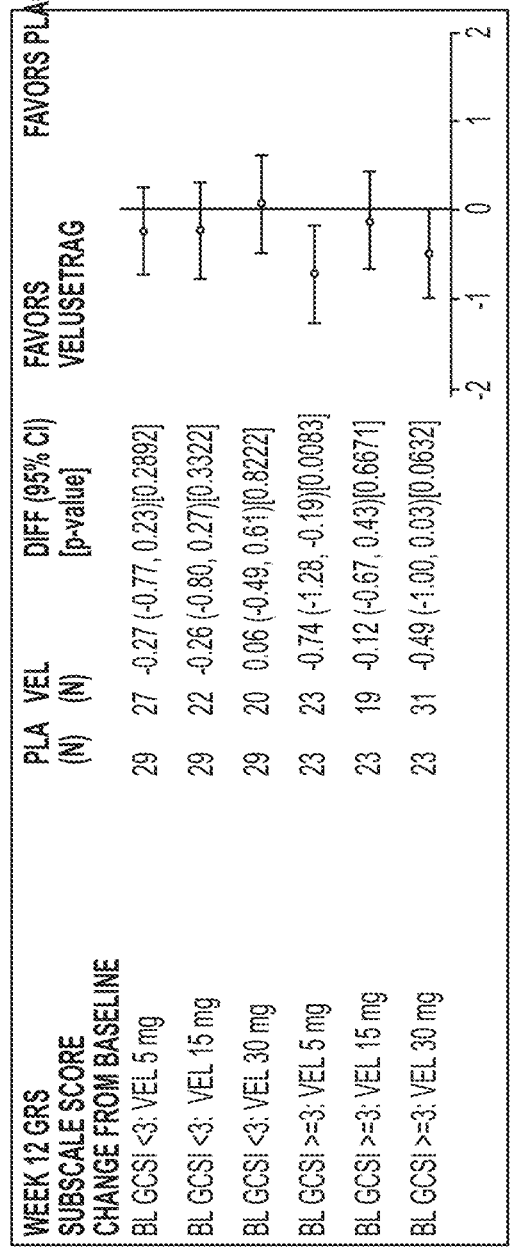
FIG. 24B illustrates GRS Total Score by Baseline Total score at 4 weeks.
Figure 25A:
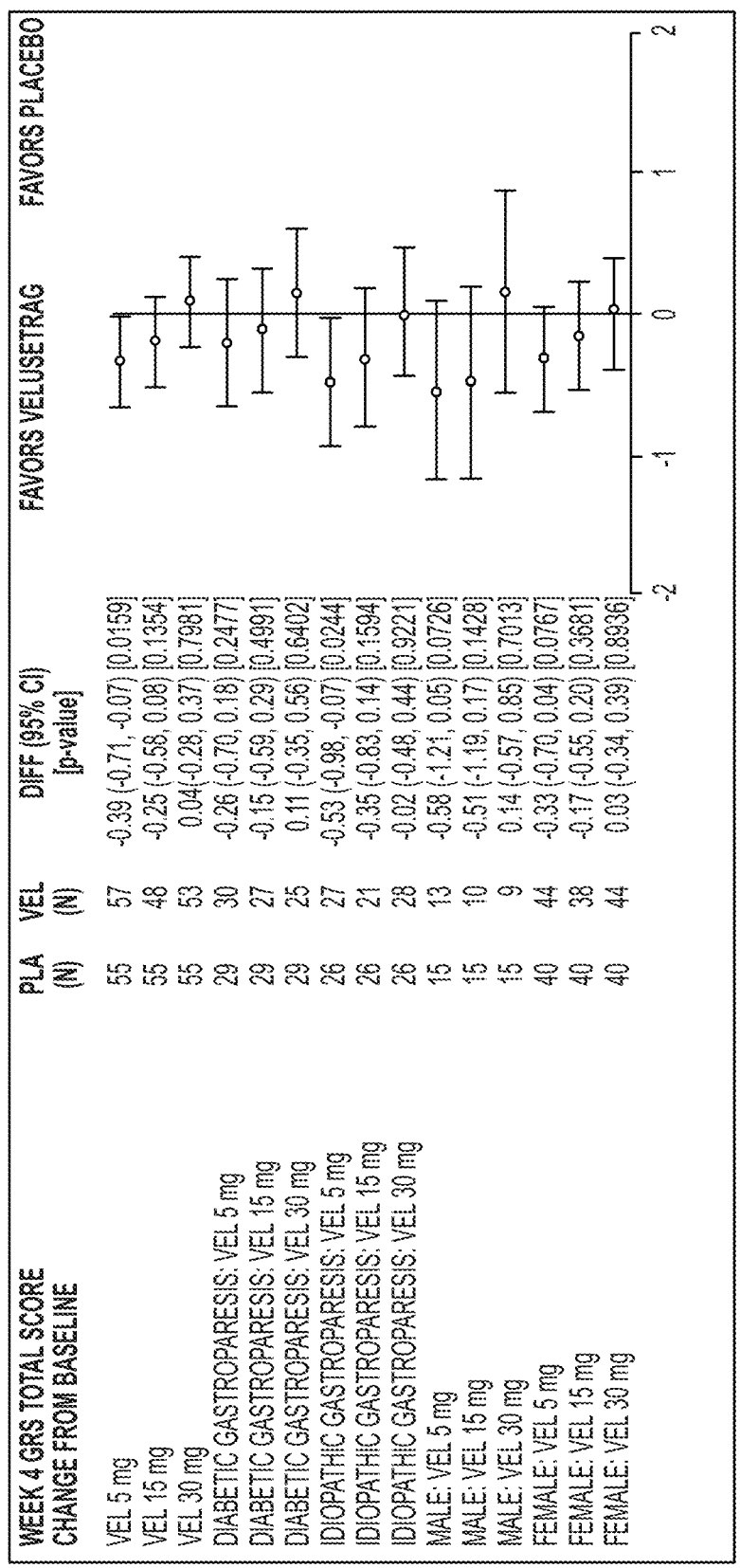
FIG. 25A illustrates GRS total score by diabetic and idiopathic gastroparesis type and by sex at 4 weeks.
Figure 25B:
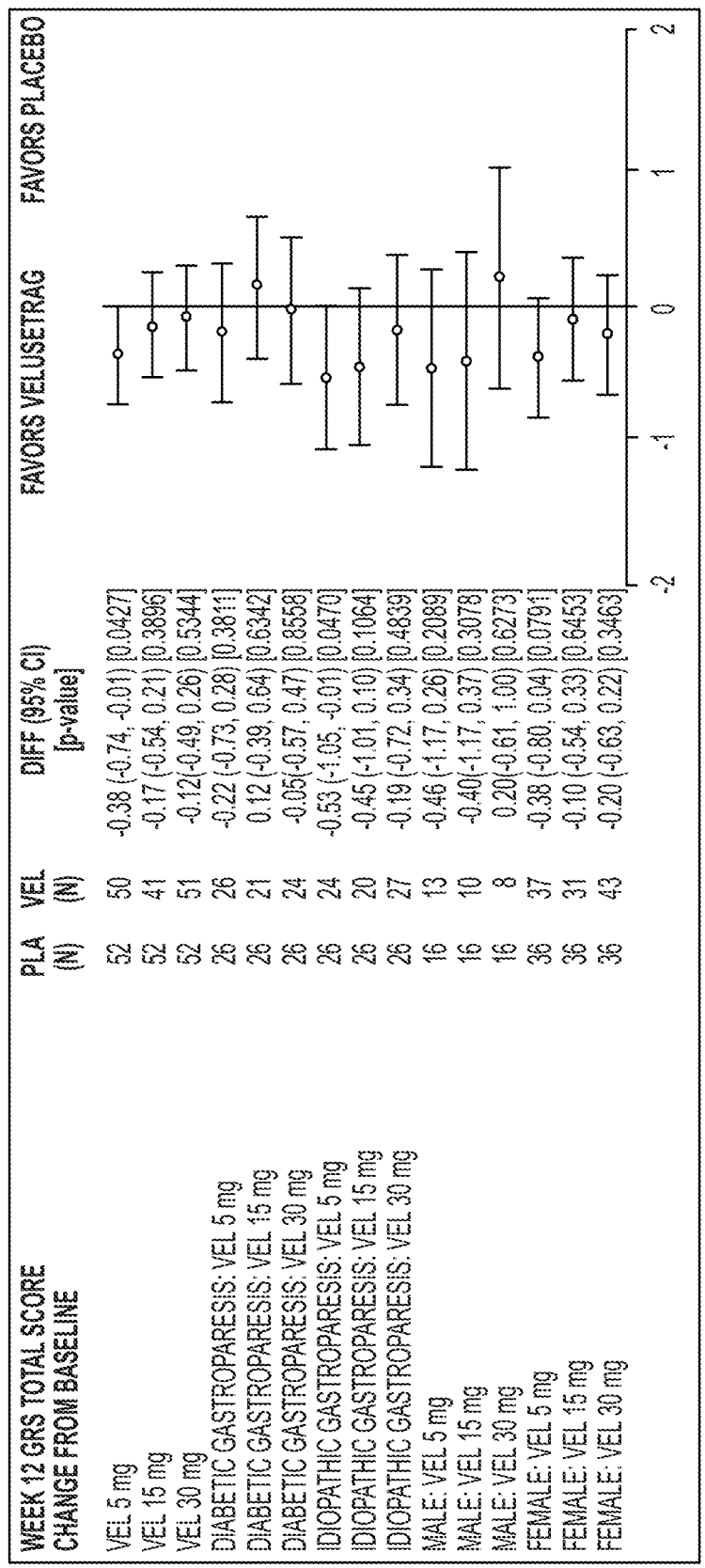
FIG. 25B illustrates GRS total score by diabetic and idiopathic gastroparesis type and by sex at 12 weeks.

A clear separation in GRS symptom total score is observed with the velusetrag 5 mg dose relative to the two higher doses and placebo throughout the full 12 weeks of dosing (FIG. 17). No evidence of tachyphylaxis or diminution of effect is observed over the 12 weeks of dosing. As expected, there is an increase in symptom score in weeks 13 and 14 when subjects were off therapy.

FIGS. 18 to 25 illustrate the results demonstrating the efficacy of velusetrag versus placebo administration in reducing, ameliorating, and alleviating, giving relief to, treating, the symptoms associated with gastroparesis by GRS total score. LS Mean Differences in each subgroup are calculated based on repeated measures mixed effect model with change from baseline in weekly GRS total score as dependent variable, treatment, gastroparesis type (diabetic vs. idiopathic), GE test time (historical vs. prospective), baseline GRS total score, time, subgroup variable, interaction effect of treatment by time, baseline GRS total score by time, treatment by subgroup variable, time by subgroup variable and treatment by time by subgroup variable as fixed effect, a random effect of subject within site, using an unstructured covariance structure.

2.7 Psychometric Evaluation of GRS

In total, 232 subjects were used for the psychometric evaluation of the GRS. After initial psychometric reviews were conducted, 4 items were removed from the scoring of the GRS and another item was moved from one domain to another. The domain for constipation was removed due to interpretation issues. Subsequent psychometric analysis established the unidimensional and proper fit for remaining 6 GRS domains.

GRS Factor 1 (also Summary Score 1) comprised fullness/early satiety, bloating, upper abdominal pain, and epigastric burning domains, whereas GRS Factor 2 (also Summary Score 2) comprised nausea and vomiting domains. Item and scale psychometric at baseline data revealed that no special weighting of the items was required. Item and scale level psychometric at baseline data revealed strong findings for all domains and summary scores, except for a slightly higher than expected equality for variance score for the vomiting domain. Fullness/early satiety domain had low test-retest reliability which may be a characteristic of the symptom.

After the psychometric evaluation the GRS was summarized using two summary scores: Summary Score 1 combined the fullness/early satiety, bloating, upper abdominal pain, and epigastric burning domains and Summary Score 2 combined the nausea and vomiting domains. Larger effects were observed in Summary Score 1 relative to Summary Score 2 as noted in the individual symptom domains where nausea and vomiting were the least affected symptom domains with velusetrag treatment, though trends for improvement were noted in these two symptoms.

For Summary Score 1 at Week 4, Velusetrag 5 mg showed a statistically significant LS mean difference of −0.4 points (95% CI: −0.72, −0.08; p=0.0143) compared to placebo for the ITT analysis set; the numerical effect was maintained at week 12 (End of Therapy) (−0.4 points 95% CI: −0.75, 0.01; p=0.0536). (Table 11)

For Summary Score 2, numerical trends were observed, with an LS mean difference of −0.2 points (95% CI: −0.43, 0.03; p=0.0841) at Week 12, compared to placebo (Table 9).

These symptoms changes with velusetrag 5 mg was notable at a subject level and represented a greater than 1 to 1.5 points change from baseline in level of total symptom burden from severe symptoms to moderate/mild symptoms, or from moderate to mild/no symptoms.

TABLE 11

Summary of LS mean change from baseline and placebo
in Weekly GRS in Summary Score 1 (ITT population)

| | Placebo (N = 59) | Velusetrag 5 mg (N 59) | Velusetrag 15 mg (N = 53) | Velusetrag 30 mg (N = 57) |
|---|---|---|---|---|
| Week 4 Change from Baseline GRS PRO Factor 1 | | | | |
| LS Mean (SE) | −0.9 (0.12) | −1.3 (0.11) | −1.1 (0.12) | −0.8 (0.12) |
| LS Mean Difference (SE) | | −0.4 (0.16) | −0.2 (0.17) | 0.0 (0.17) |
| 95% CI for LS Mean Difference | | −0.72, −0.08 | −0.58, 0.08 | −0.28, 0.37 |
| P-value vs. Placebo | | 0.0143 | 0.0827 | 0.8599 |
| Week 8 Change from Baseline GRS PRO Factor 1 | | | | |
| LS Mean (SE) | −1.1 (0.13) | −1.4 (0.13) | −1.2 (0.14) | −1.1 (0.13) |
| LS Mean Difference (SE) | | −0.3 (0.18) | −0.1 (0.19) | −0.1 (0.18) |
| 95% CI for LS Mean Difference | | −0.69, 0.03 | −0.55, 0.19 | −0.46, 0.27 |
| P-value vs. Placebo | | 0.0684 | 0.4350 | 0.6191 |
| Week 12 Change from Baseline GRS PRO Factor 1 | | | | |
| LS Mean (SE) | −1.1 (0.14) | −1.5 (0.13) | −1.3 (0.15) | −1.2 (0.14) |
| LS Mean Difference (SE) | | −0.4 (0.19) | −0.2 (0.2) | −0.1 (0.2) |
| 95% CI for LS Mean Difference | | −0.75, −0.01 | −0.61, 0.18 | −0.47, 0.30 |
| P-value vs. Placebo | | 0.0536 | 0.2920 | 0.6637 |

TABLE 12

Summary of LS mean change from baseline and placebo
in Weekly GRS in Summary Score 2 (ITT population)

| | Placebo (N = 59) | Velusetrag 5 mg (N = 59) | Velusetrag 15 mg (N = 53) | Velusetrag 30 mg (N = 57) |
|---|---|---|---|---|
| Week 4 Change from Baseline GRS PRO Factor 2 | | | | |
| LS Mean (SE) | −0.7 (0.09) | 0.8 (0.08) | −0.7 (0.09) | −0.6 (0.09) |
| LS Mean Difference (SE) | | −0.1 (0.12) | −0.0 (0.12) | 0.1 (0.12) |
| 95% CI for LS Mean Difference | | −0.38, −0.09 | −0.26, 0.23 | −0.19, 0.29 |
| P-value vs. Placebo | | 0.0143 | 0.0827 | 0.8599 |
| Week 8 Change from Baseline GRS PRO Factor 2 | | | | |
| LS Mean (SE) | −0.8 (0.09) | −0.9 (0.09) | −0.8 (0.10) | −0.8 (0.09) |
| LS Mean Difference (SE) | | −0.1 (0.13) | −0.0 (0.13) | −0.0 (0.13) |
| 95% CI for LS Mean Difference | | −0.69, 0.03 | −0.55, 0.19 | −0.46, 0.27 |
| P-value vs. Placebo | | 0.3705 | 0.9095 | 0.9507 |
| Week 12 Change from Baseline GRS PRO Factor 2 | | | | |
| LS Mean (SE) | −0.8 (0.08) | −1.0 (0.08) | −0.9 (0.09) | −1.0 (0.08) |
| LS Mean Difference (SE) | | −0.2 (0.12) | −0.1 (0.12) | −0.2 (0.12) |
| 95% CI for LS Mean Difference | | −0.43, −0.03 | −0.03, 0.18 | −0.40, 0.070 |
| P-value vs. Placebo | | 0.0841 | 0.6118 | 0.1638 |

A clear separation in GRS Summary Score 1 and GRS Summary Score 2 was observed with the velusetrag 5 mg group to the higher doses and to placebo through the full 12 weeks of treatment. No evidence of tachyphylaxis or diminution of effect was observed over the 12 weeks of treatment. There was a slight increase in symptom score in Weeks 13 and 14 when subjects were off therapy.

2.8 Change in Individual Symptom Domains

Figure 26A:
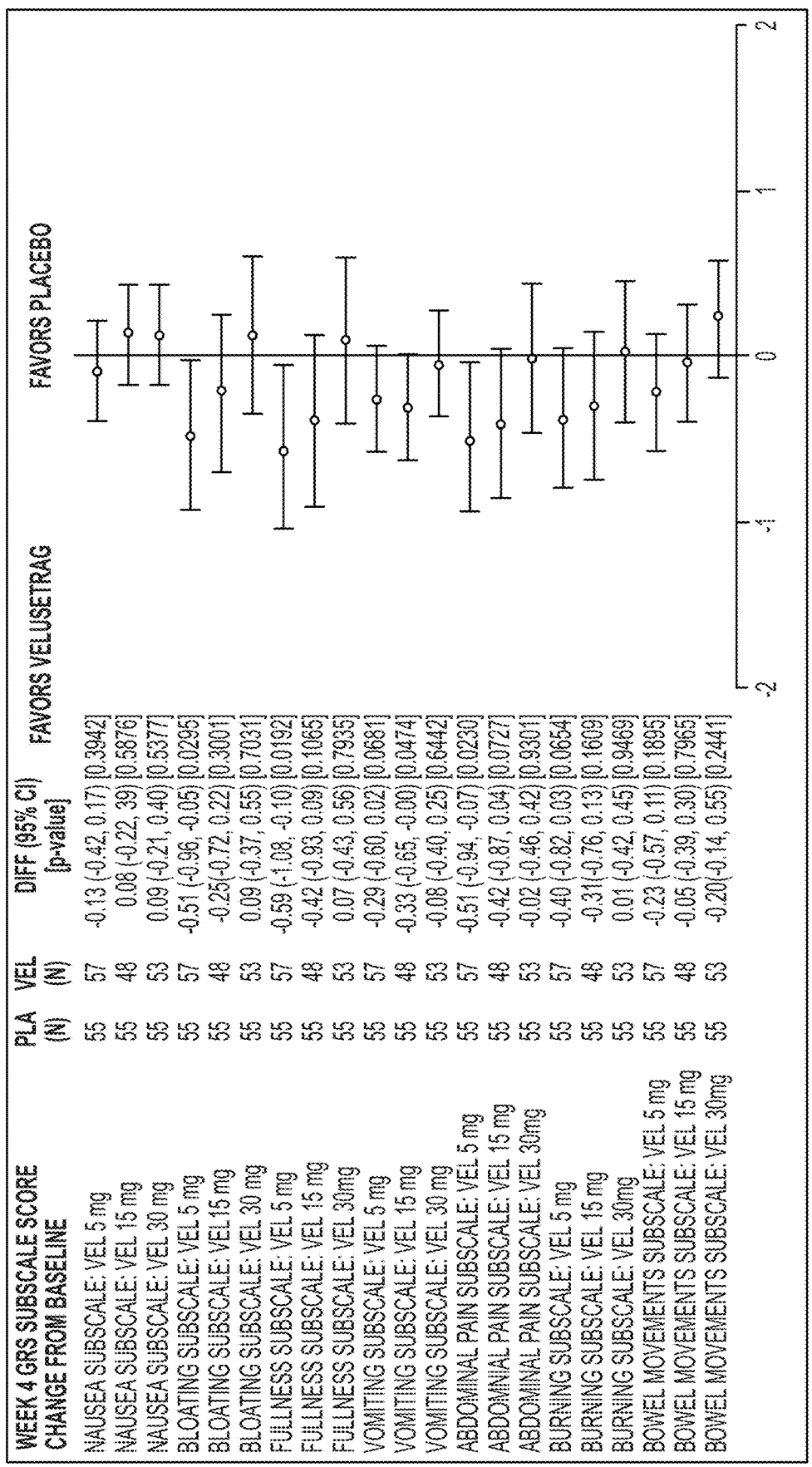
FIG. 26A illustrates Week 4 GRS subscale score by individual symptoms.
Figure 26B:
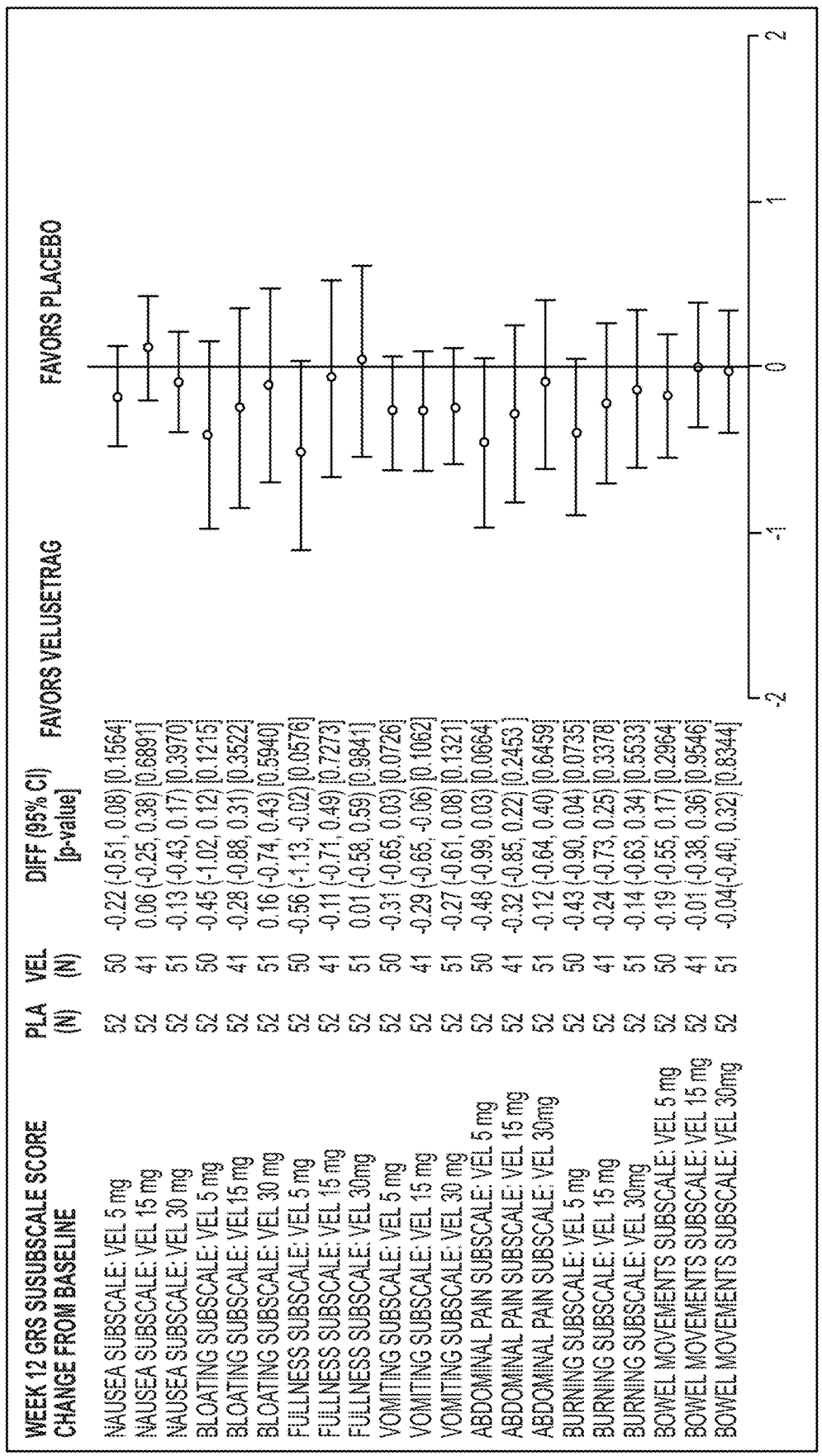
FIG. 26B illustrates Week 12 GRS subscale score by individual symptoms.
Figure 27A:
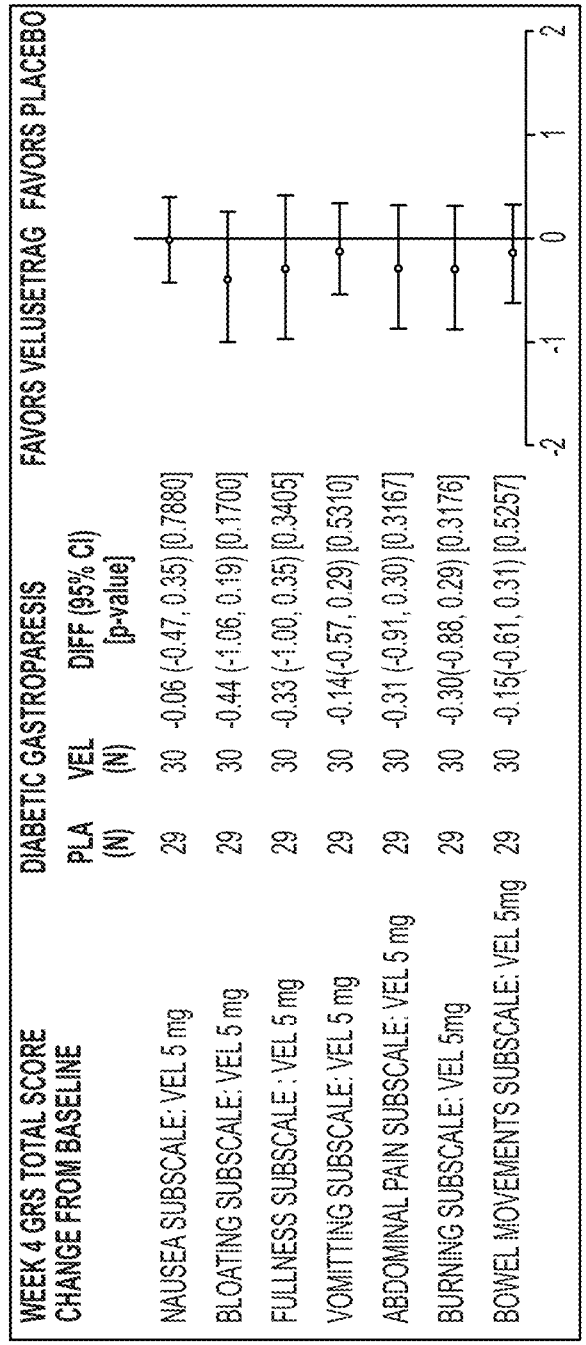
FIG. 27A illustrates Week 4 GRS subscale score by individual symptoms.
Figure 27B:
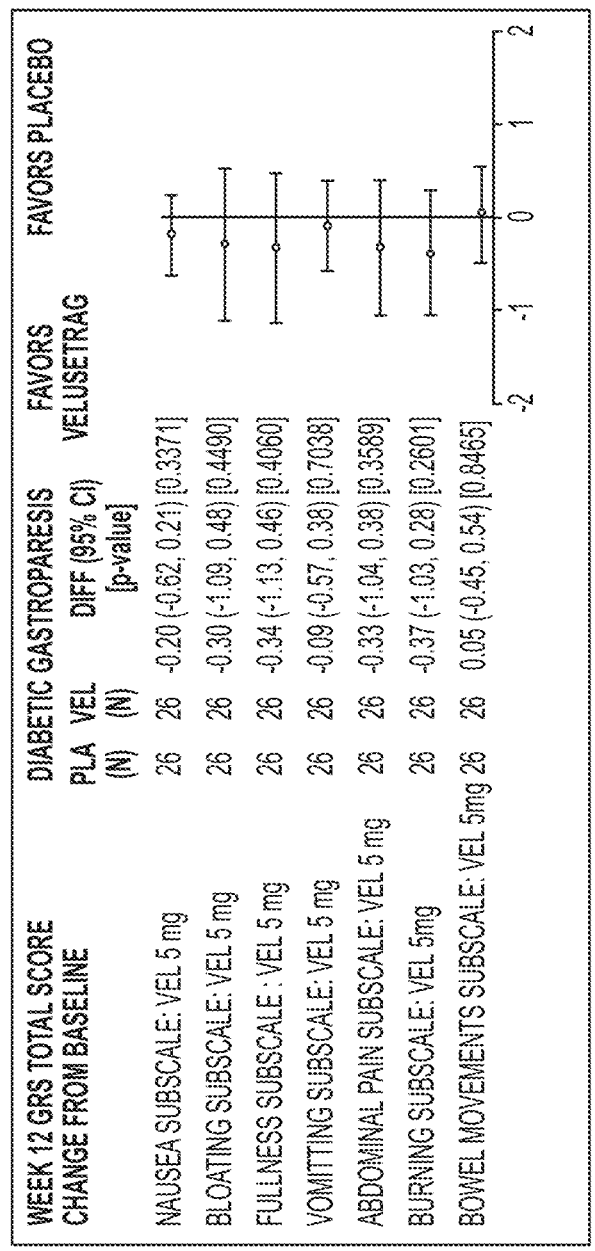
FIG. 27B illustrates Week 12 GRS subscale score by individual symptoms.
Figure 28A:
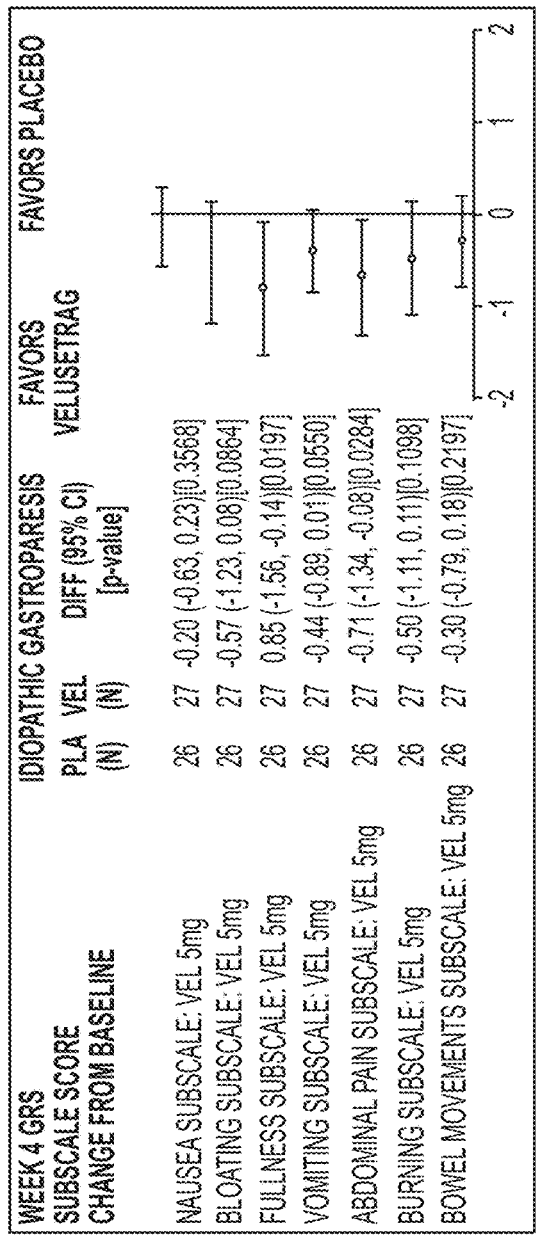
FIG. 28A illustrates Week 4 GRS subscale score by individual symptoms.
Figure 28B:
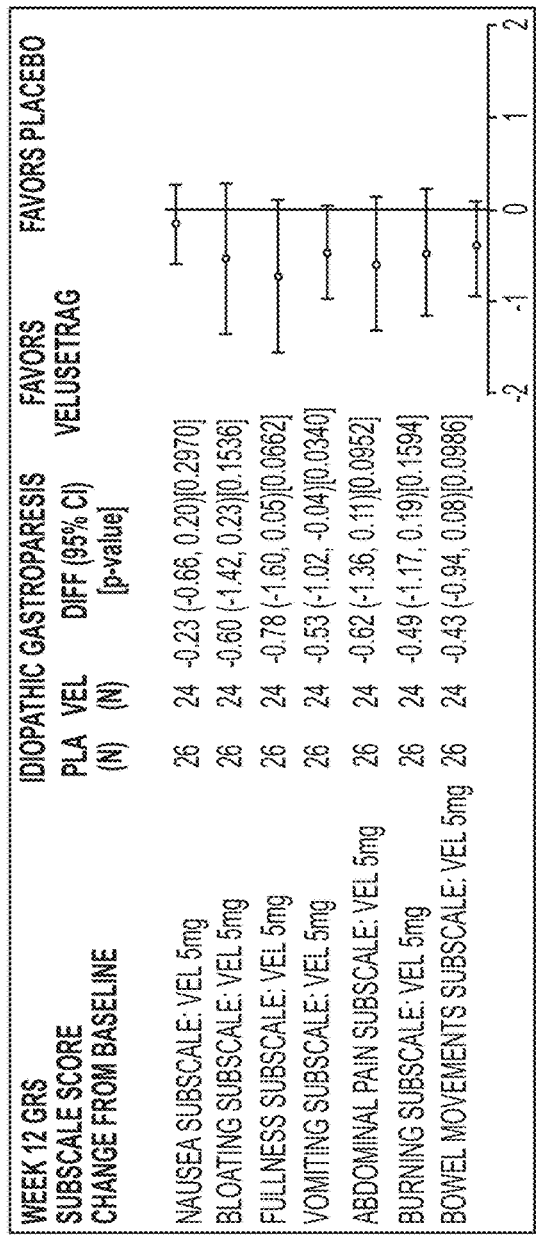
FIG. 28B illustrates Week 12 GRS subscale score by individual symptoms.
Figure 29:
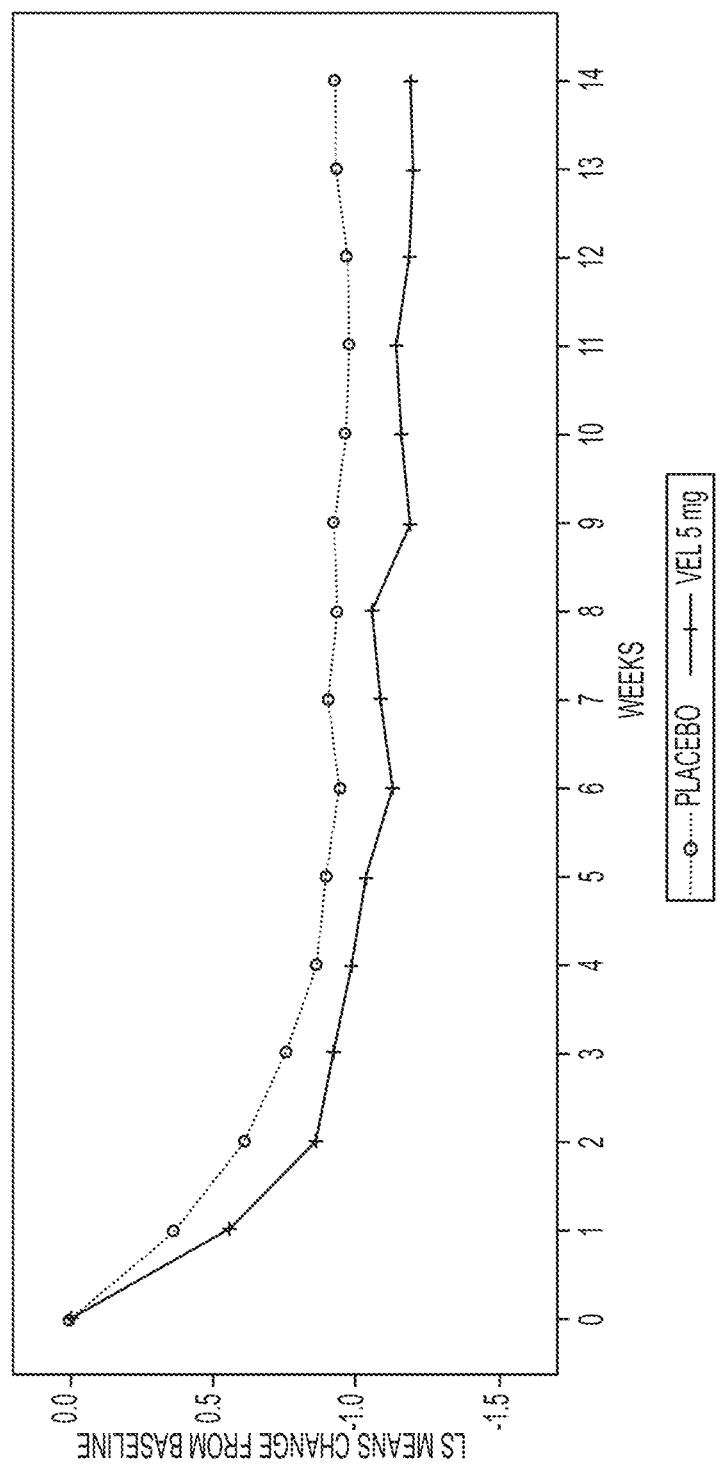
FIG. 29 illustrates LS mean change from baseline in GRS nausea scores, weeks 1-14 (ITT population, placebo and velusetrag 5 mg).
Figure 30:
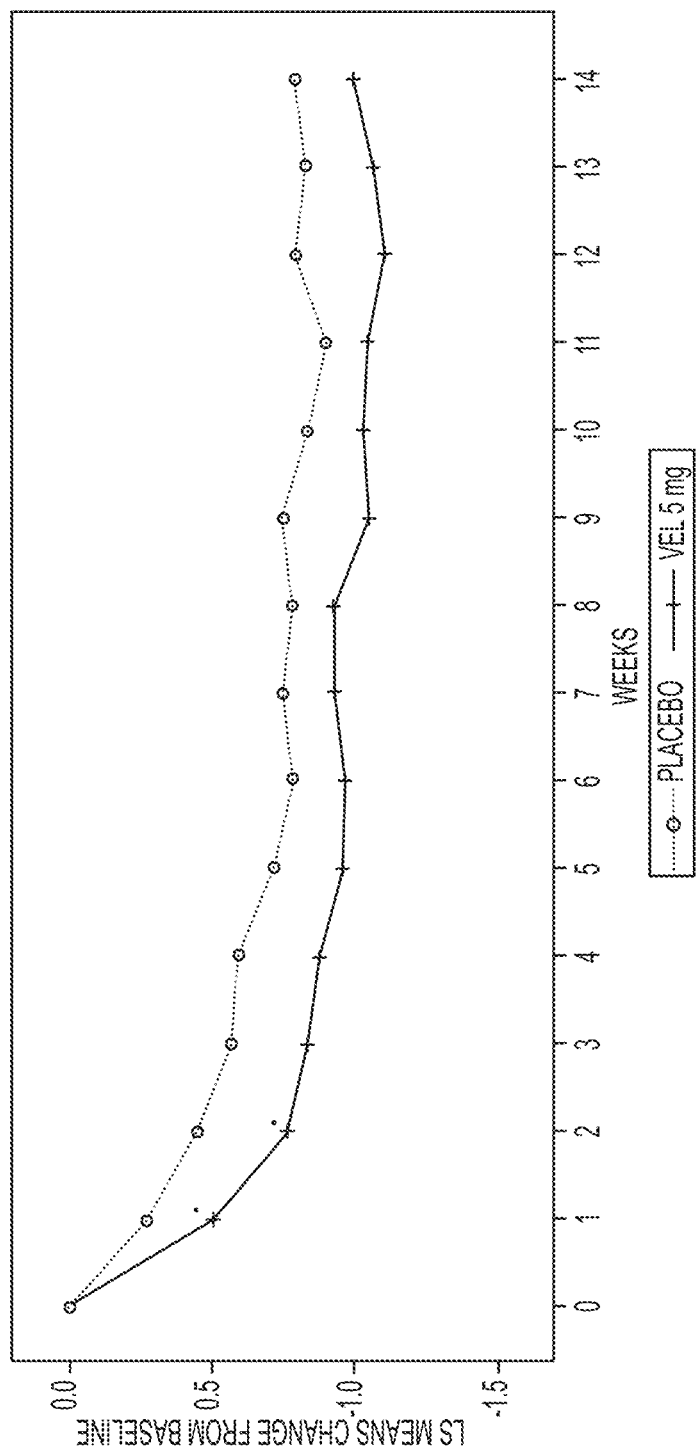
FIG. 30 illustrates LS mean change from baseline in GRS vomiting scores, weeks 1-14 (ITT population, placebo and velusetrag 5 mg).
Figure 31:
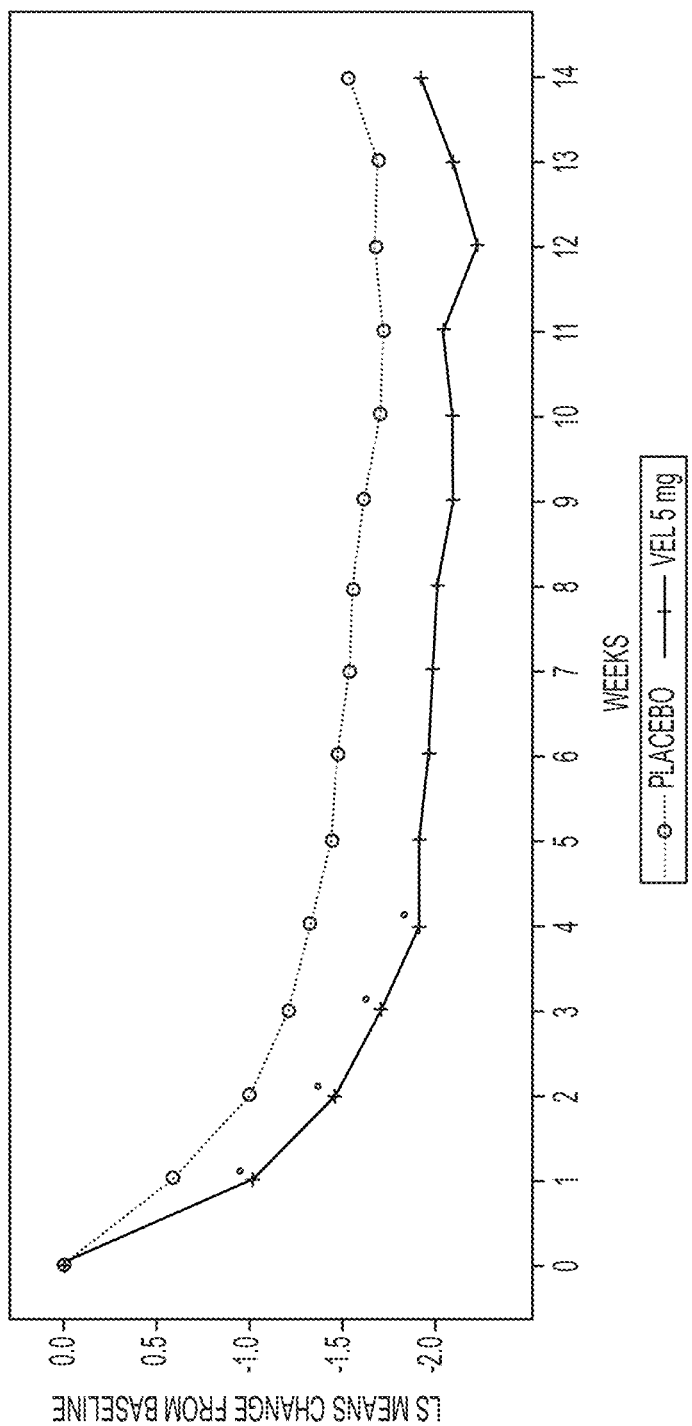
FIG. 31 illustrates LS mean change from baseline in GRS fullness/early satiety scores, weeks 1-14 (ITT population, placebo and velusetrag 5 mg).
Figure 32:
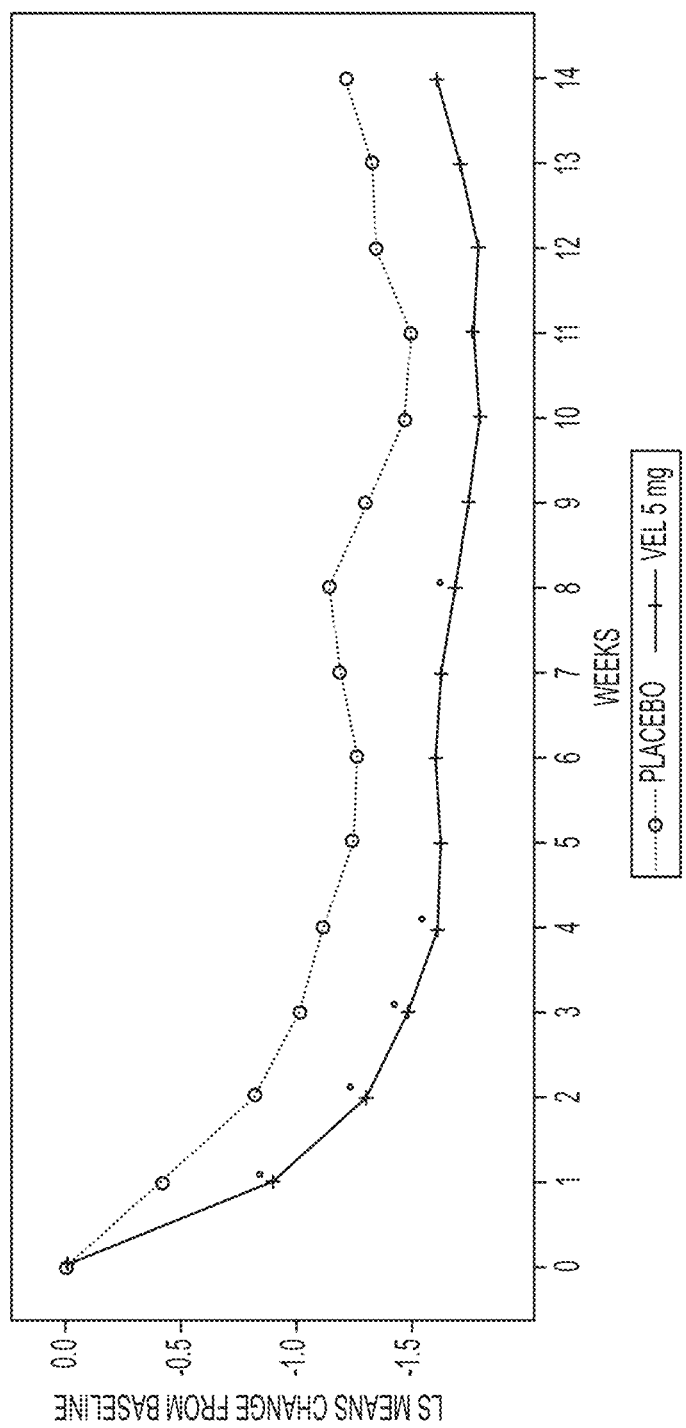
FIG. 32 illustrates LS mean change from baseline in GRS bloating scores, weeks 1-14 (ITT population, placebo and velusetrag 5 mg).
Figure 33:
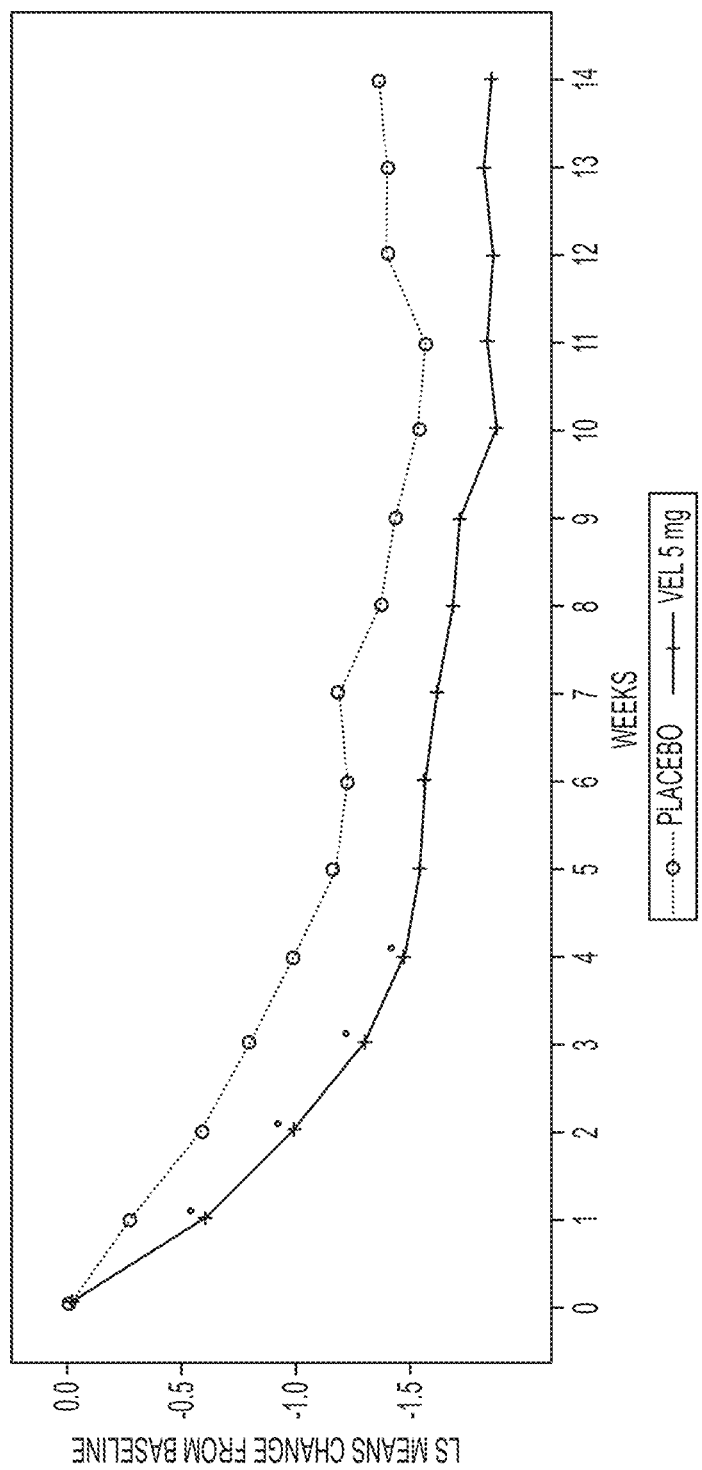
FIG. 33 illustrates LS mean change from baseline in GRS upper abdominal pain scores, weeks 1-14 (ITT population, placebo and velusetrag 5 mg).
Figure 34:
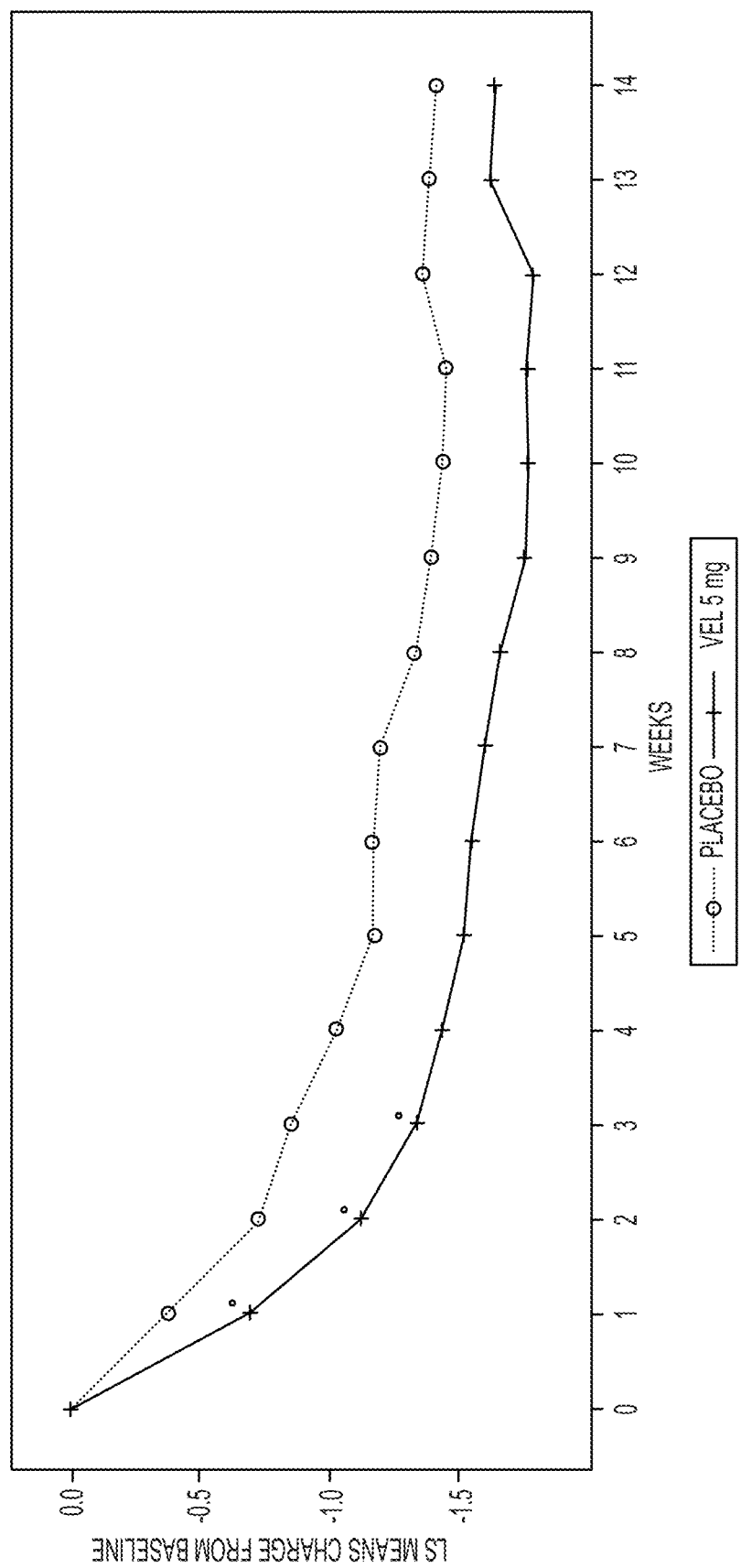
FIG. 34 illustrates LS mean change from baseline in GRS gastrointestinal (GI) burning scores, weeks 1-14 (ITT population, placebo and velusetrag 5 mg).
Figure 35:
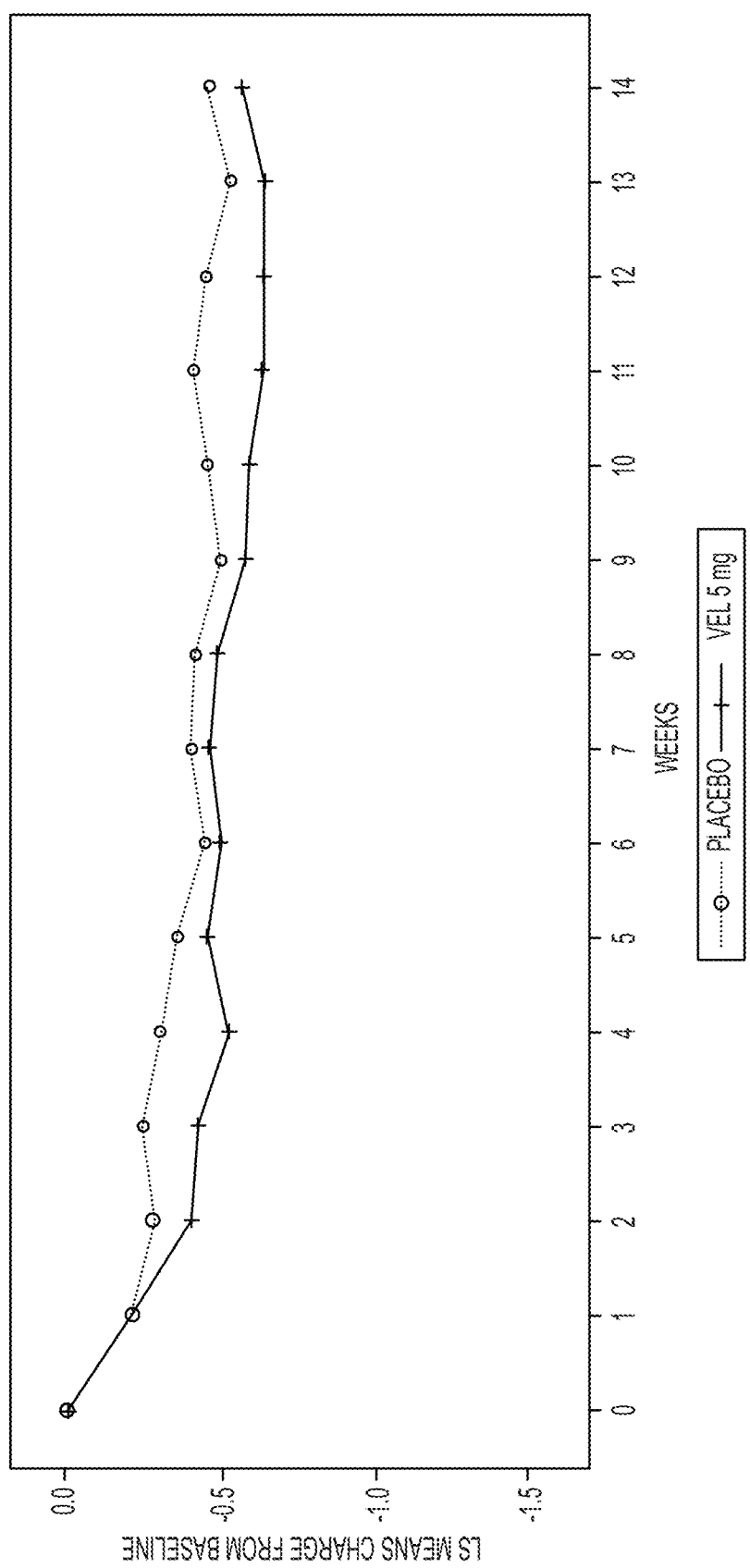
FIG. 35 illustrates LS mean change from baseline in GRS bowel movement scores, weeks 1-14 (ITT population, placebo and velusetrag 5 mg).
Figure 36:
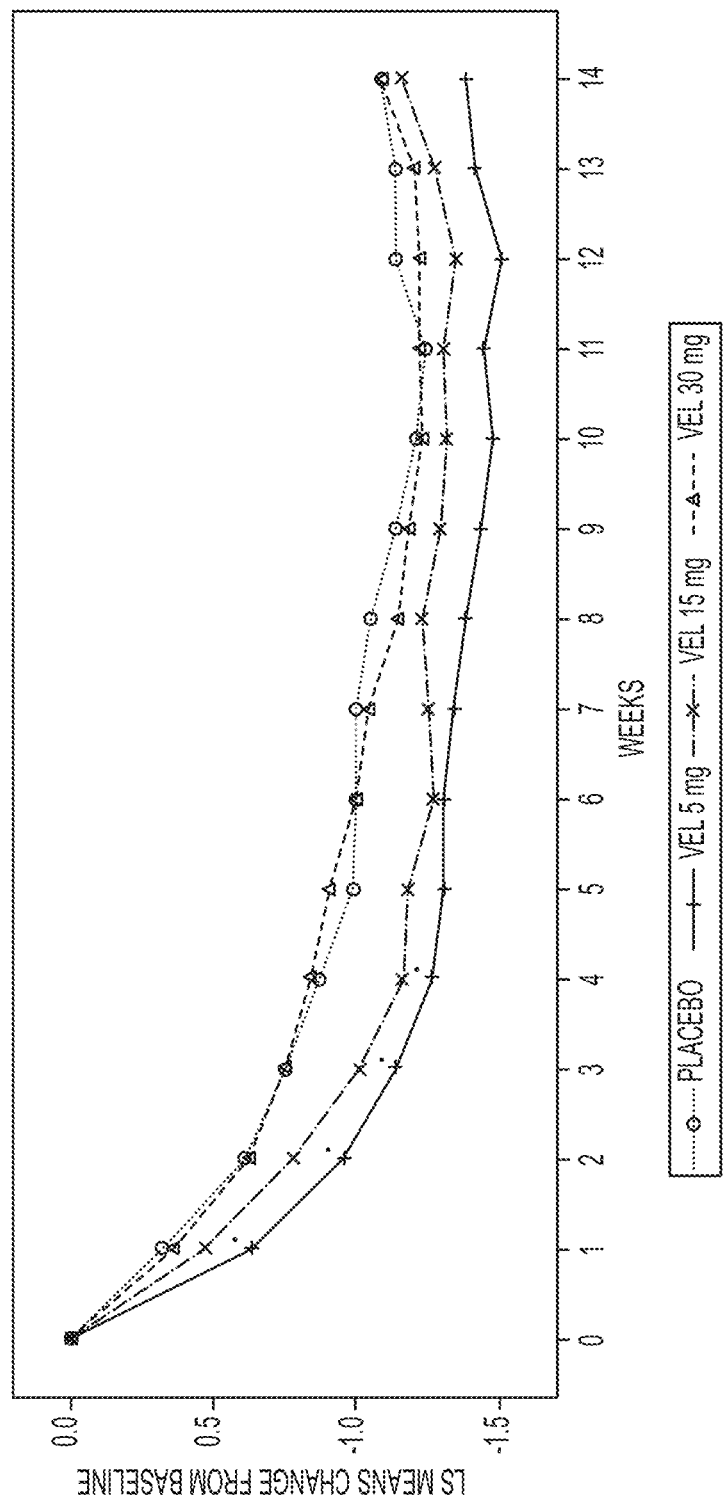
FIG. 36 illustrates LS mean change from baseline in weekly summary score 1 (ITT analysis set).
Figure 37:
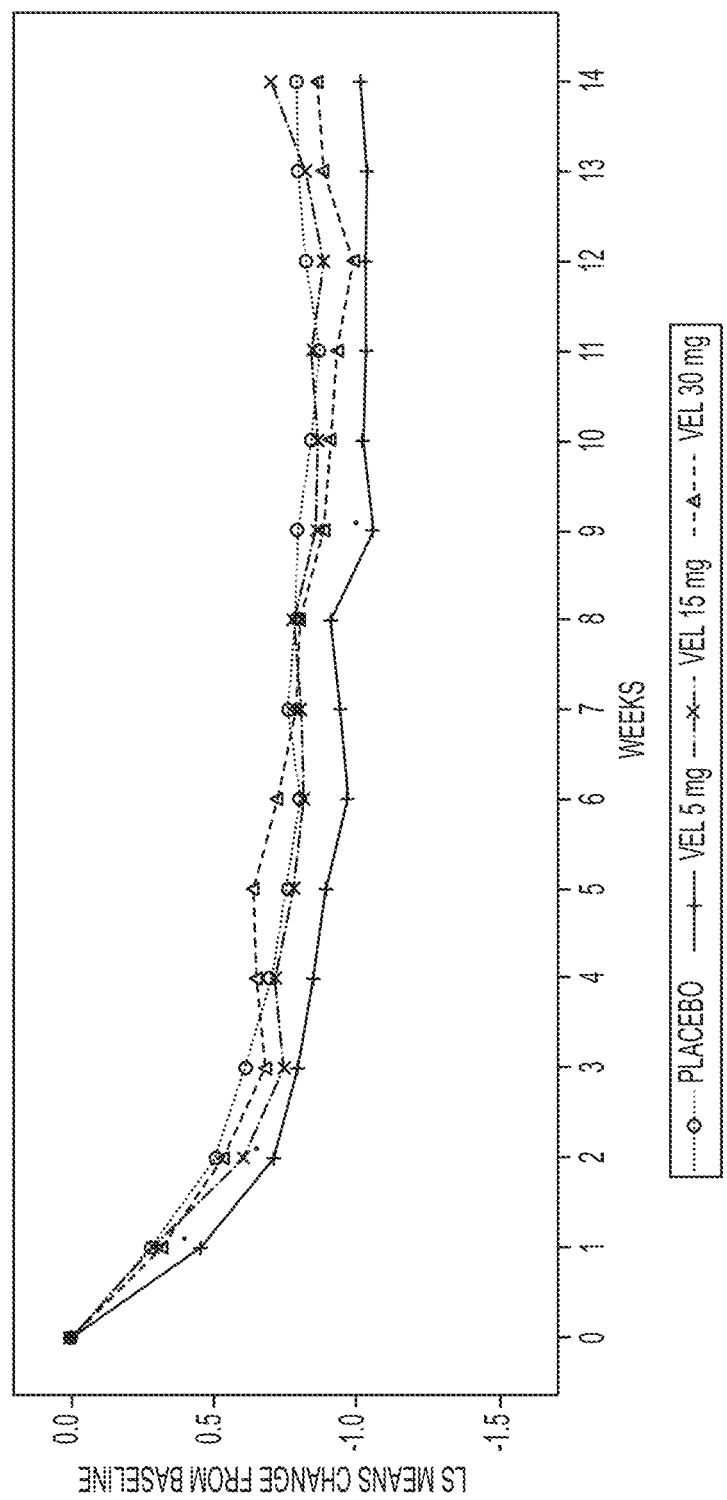
FIG. 37 illustrates LS mean change from baseline in weekly summary score 2 (ITT analysis set).
Figure 38:
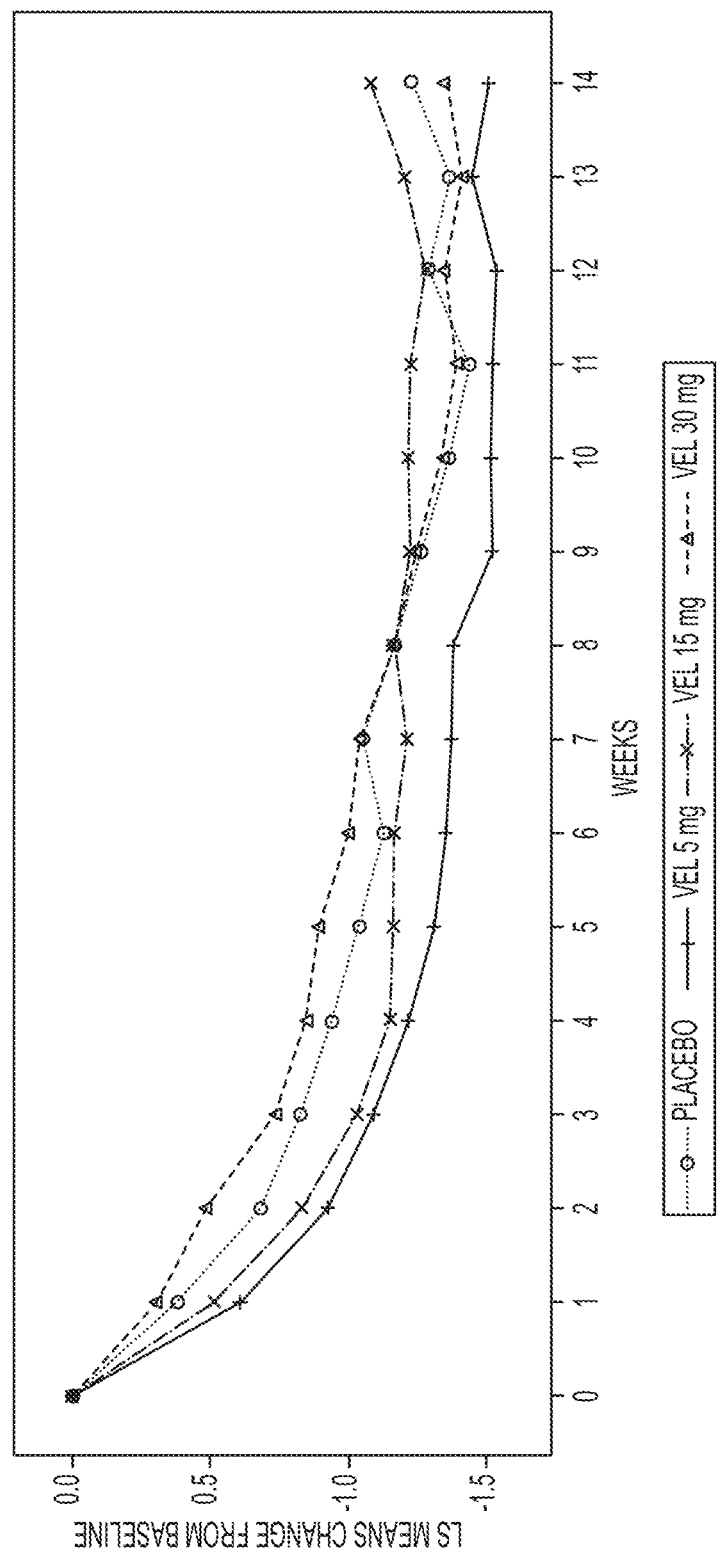
FIG. 38 illustrates LS mean change from baseline in weekly summary score 1 (diabetic gastroparesis population).
Figure 39:
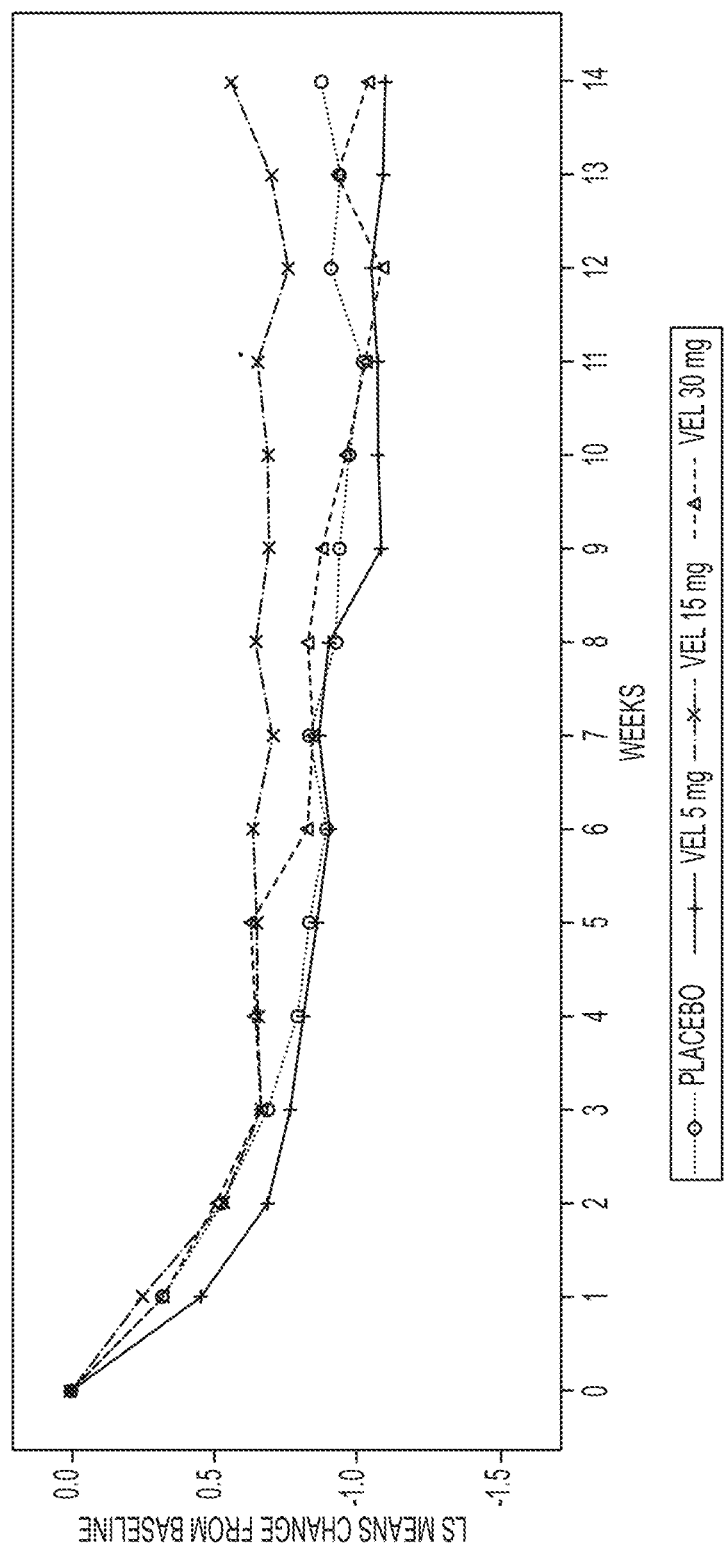
FIG. 39 illustrates LS mean change from baseline in weekly summary score 2 (diabetic gastroparesis population).
Figure 40:
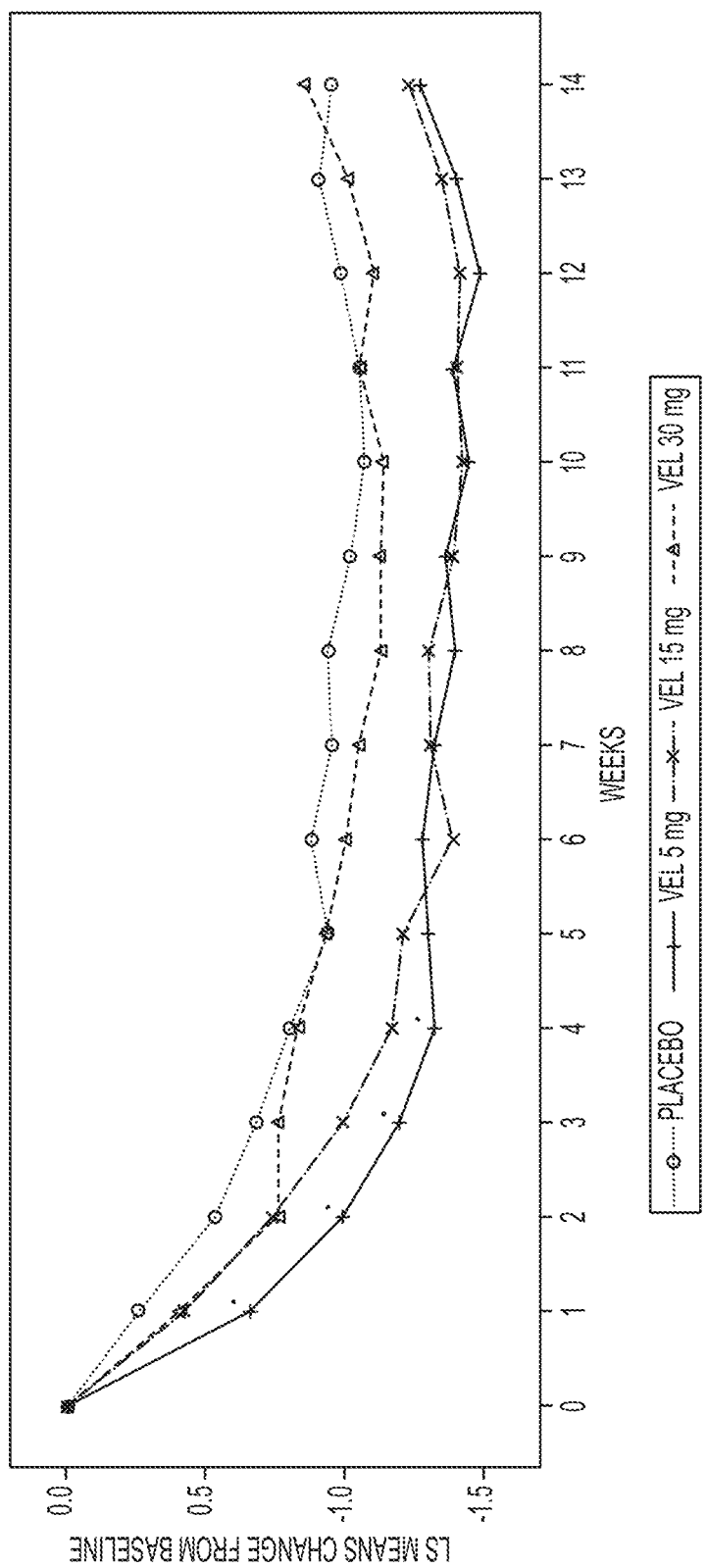
FIG. 40 illustrates LS mean change from baseline in weekly summary core 1 (idiopathic gastroparesis population).
Figure 41:
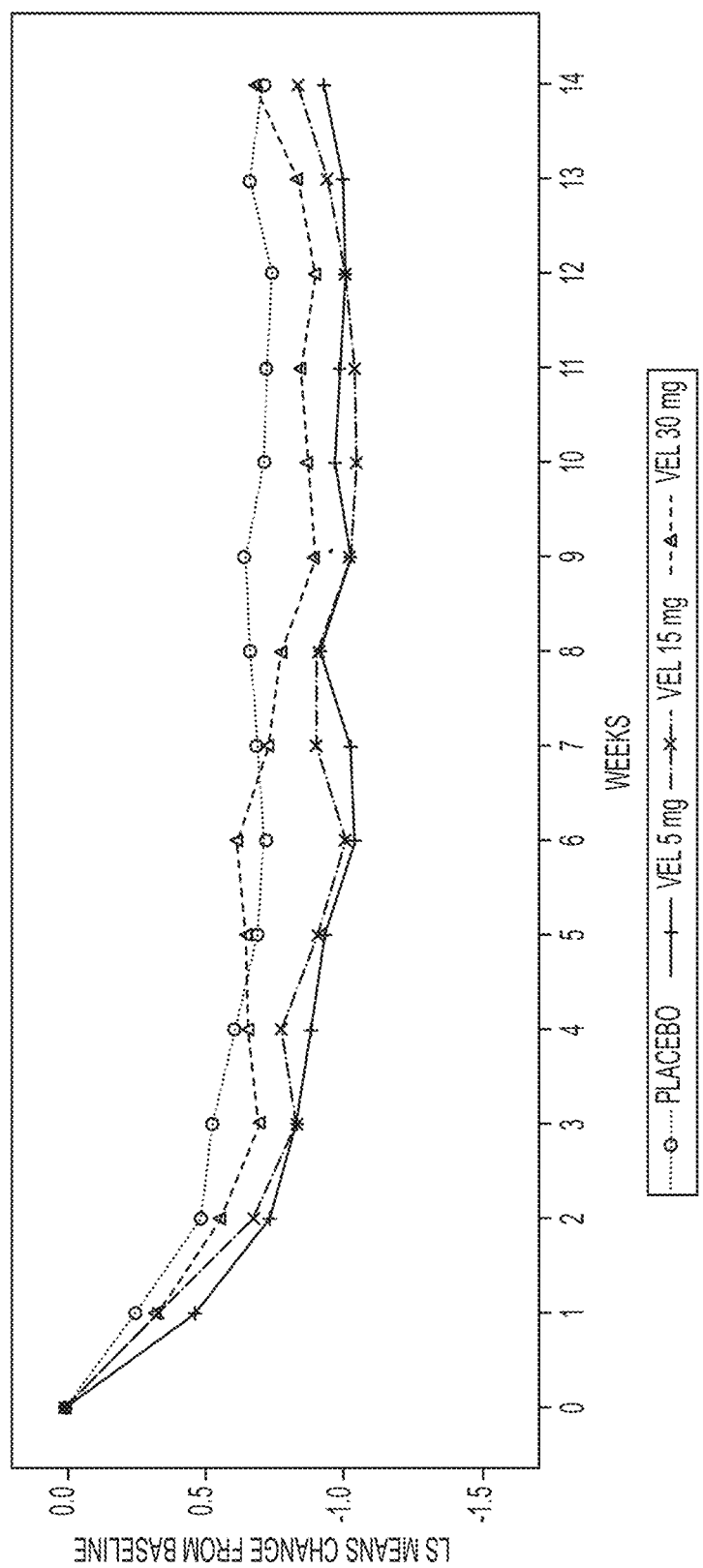
FIG. 41 illustrates LS mean change from baseline in weekly summary score 2 (idiopathic gastroparesis population).
Figure 42:
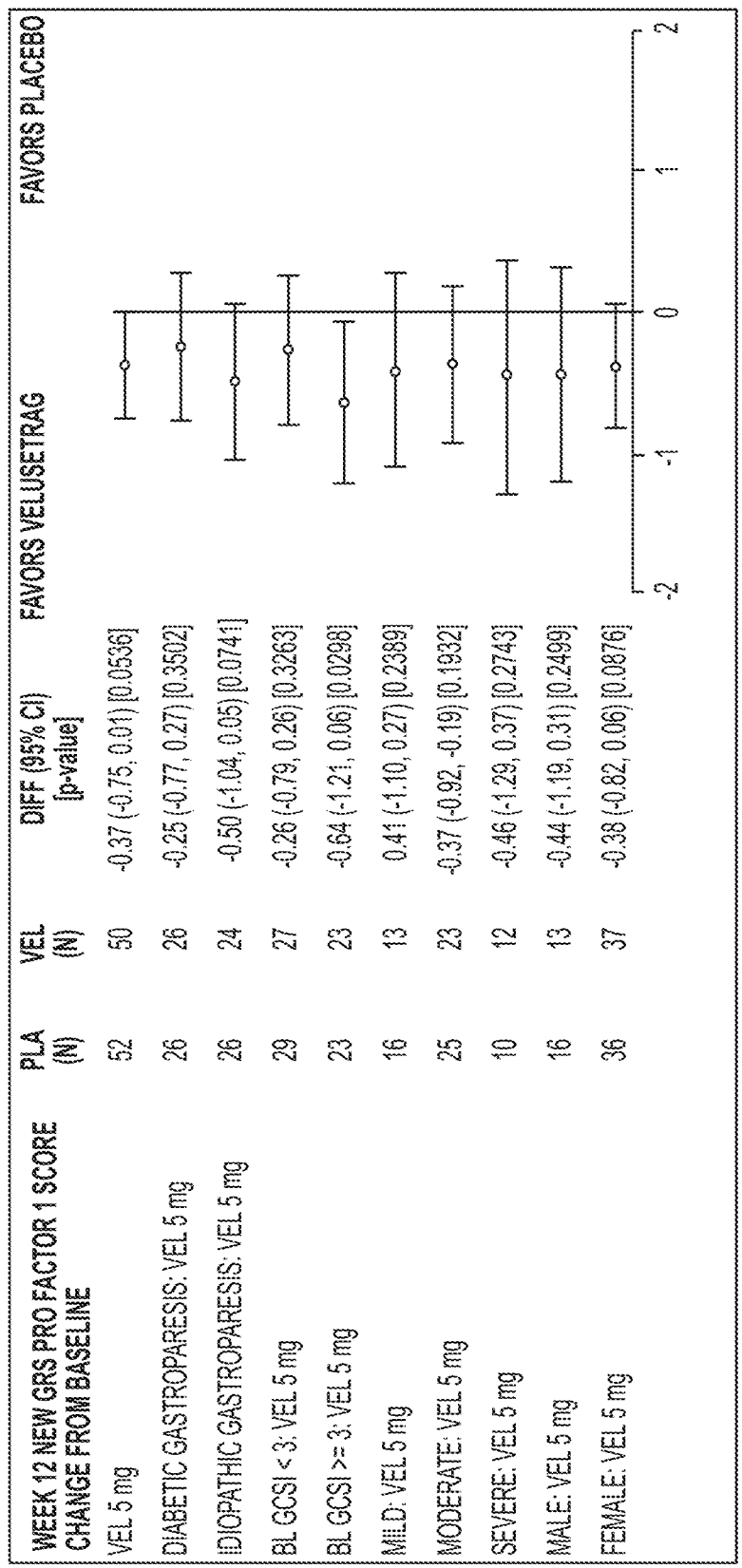
FIG. 42 illustrates LS mean change from baseline and placebo in summary score 1 at week 12 (ITT analysis set, VEL 5 mg and placebo).
Figure 43:
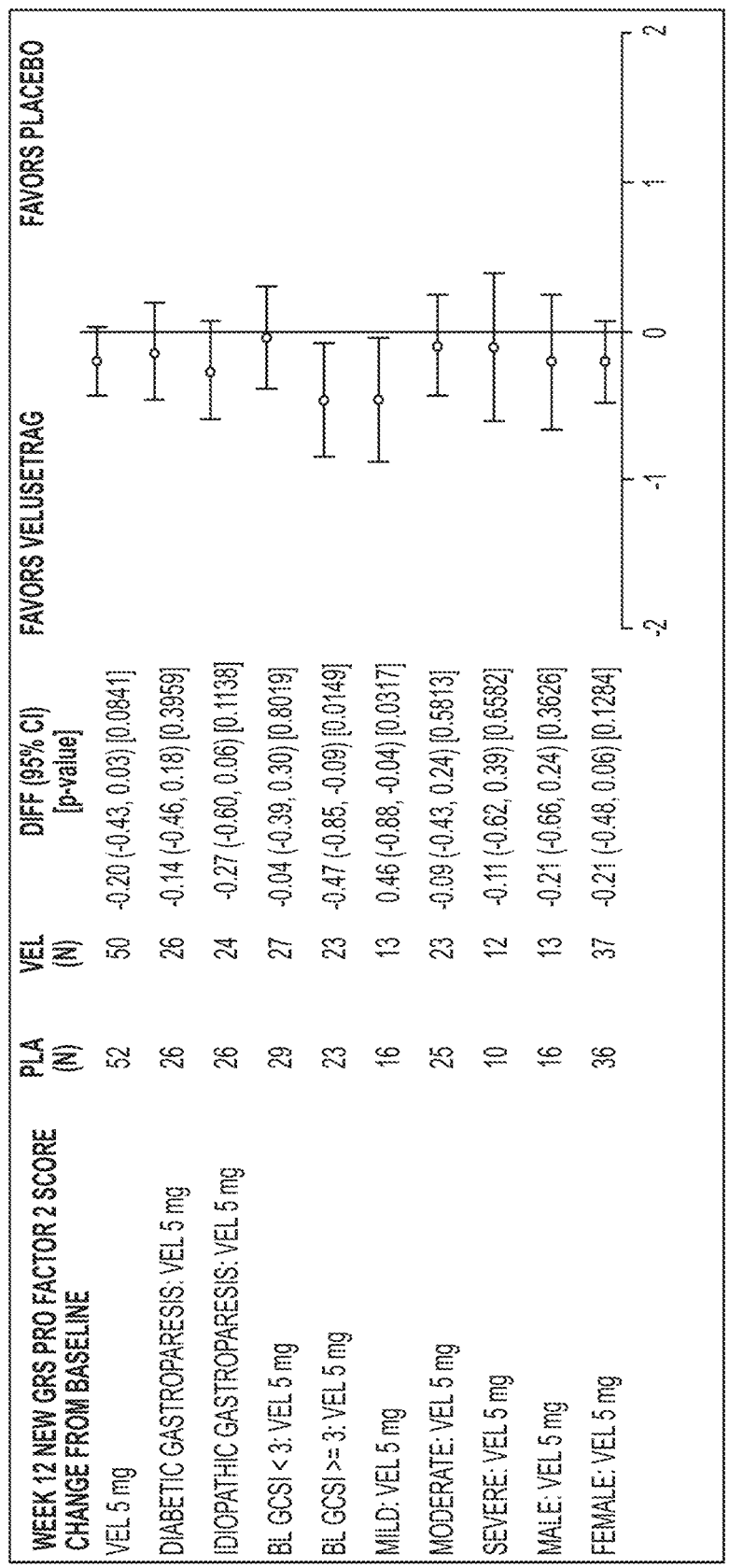
FIG. 43 illustrates LS mean change from baseline and placebo in summary score 2 at week 12 (ITT analysis set, VEL 5 mg and placebo).
Figure 44:
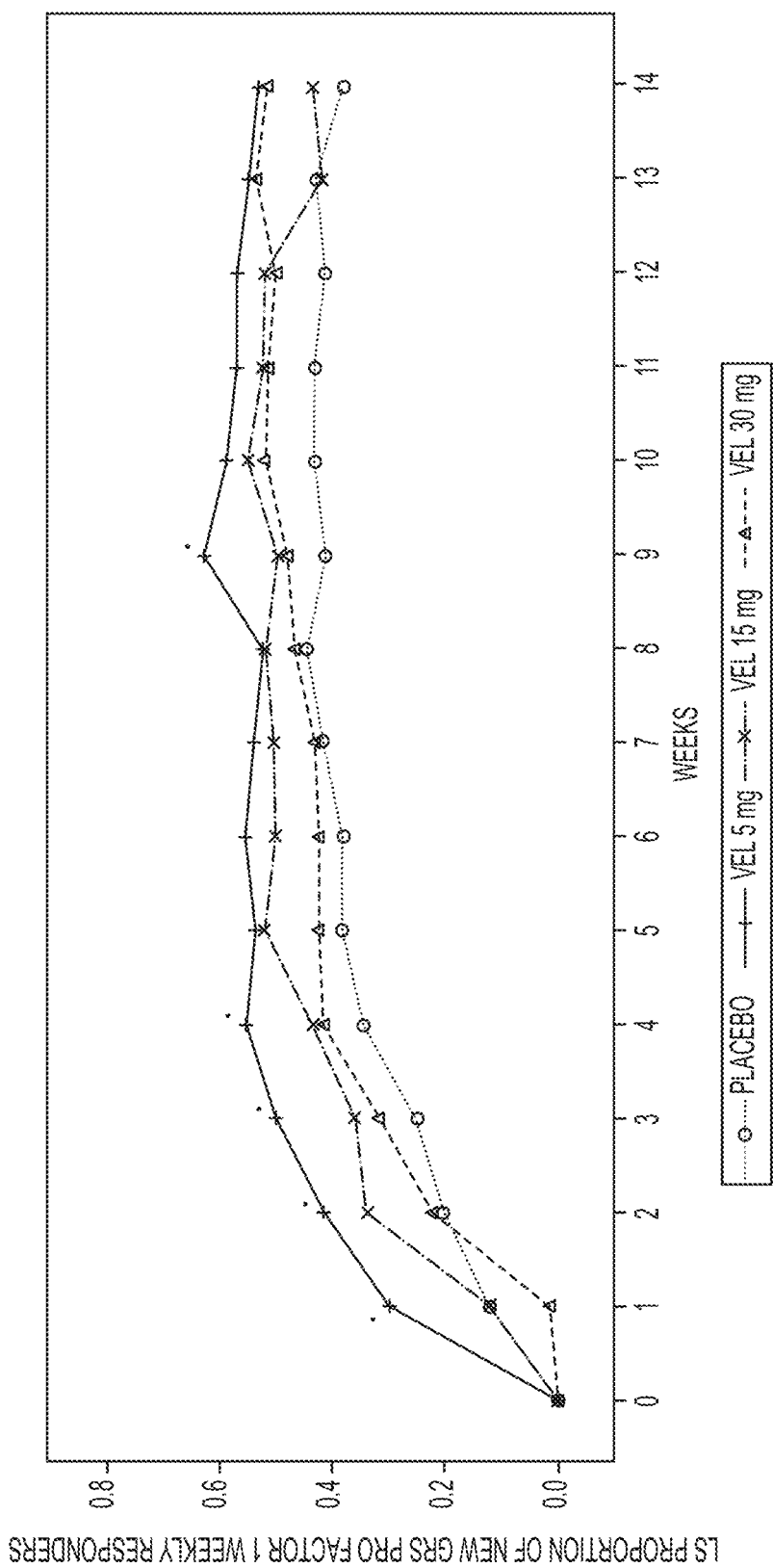
FIG. 44 illustrates LS proportions for positive weekly response in summary score 1 (ITT analysis set).
Figure 45:
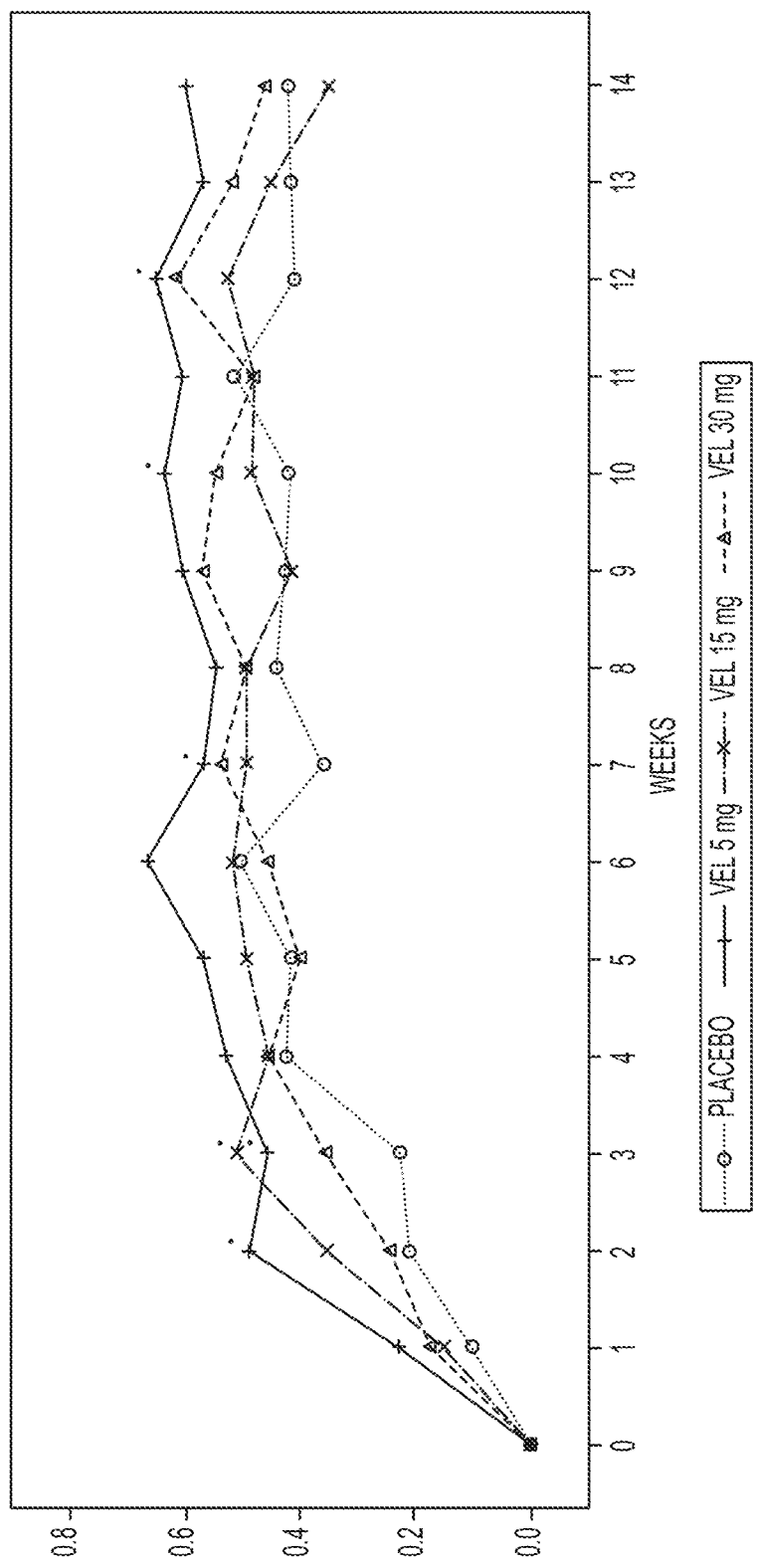
FIG. 45 illustrates LS proportions for positive weekly response in summary score 2 (ITT analysis set).

When viewing symptoms through individual symptom domains, velusetrag 5 mg resulted in improvement in every symptom domain of the GRS (see FIGS. 26-28).

FIGS. 26-28 illustrate the results demonstrating the efficacy of velusetrag versus placebo administration in reducing and alleviating the symptoms associated with gastroparesis by GRS subscale score. LS Mean Differences are calculated based on repeated measures mixed effect model with change from baseline in weekly GRS total score as dependent variable, treatment, gastroparesis type (diabetic vs. idiopathic), GE test time (historical vs. prospective), baseline subscale score, time, interaction effect of treatment by time, baseline using an unstructured covariance structure.

As shown in FIGS. 26-28, nausea and vomiting had the smallest baseline and thus had the smallest treatment effects, though a trend for improvement exists in both symptom domains. The GRS total score change was primarily driven by the changes in post-prandial fullness/early satiety, bloating, and upper abdominal pain domains, the three symptom domains for which velusetrag likely had direct mechanism through the 5-HT$_4$ receptor complex. The change from baseline for the 5 mg dose group was observed within the first week and continued to improve through weeks 6-8 stabilizing, in general, until Week 12, end of therapy for every symptom. One surprising outcome was the effect of the 5 mg dose of velusetrag on reducing visceral hypersensitivity as observed through the large reduction in upper abdominal pain.

The improvement in symptoms was observed regardless of the subgroups idiopathic and diabetic (FIG. 26-27). Higher change relative to placebo was observed in the idiopathic group through this difference is completely driven by a difference in placebo response between the two subgroups. The LS mean change from baseline for velusetrag 5 mg was 1.3 points for diabetics and 1.3 points for idiopathics though the groups had different placebo change with diabetics reduction of symptoms of 1.0 point and idiopathics of 0.8 point.

There are slightly higher treatment effects observed in subjects by baseline GCSI score though the difference is small and could be attributed to having more potential for change with higher baseline scores. When viewing the GRS total change through the lens of gastric emptying severity, listed in FIG. 23 as mild, moderate, and severe, a larger response is observed with more severe subjects albeit the sample sizes were small.

Additionally, a comparison of GRS symptoms at weeks 4 and 12 for subjects receiving velusetrag 5 showed at both weeks 4 and 12 that subjects measured by GRS subscale score favor velusetrag over placebo.

Further analyses of GRS Factors 1 and 2 demonstrate that there is a 16% and 20%, respectively, increase in favorable scores compared to placebo (see Table 13).

TABLE 13

Comparison of GRS Factors 1 and 2 to placebo

|  | Placebo | Velusetrag 5 mg | Difference |
|---|---|---|---|
| GRS Factor 1 | 37% | 53% | 16% |
| GRS Factor 2 | 33% | 53% | 20% |

Factor 1: Fullness, early satiety, bloating, upper abdominal pain, and epigastric burning
Factor 2: Nausea and vomiting 2.9 Summary Score 1 for Diabetic Gastroparesis Population Summary score 1 was evaluated in the group of patients affected by diabetic gastroparesis. Results are reported in Table 14.

TABLE 14

Summary Score 1 for Diabetic Gastroparesis Population

|  | Placebo (N = 31) | Velusetrag 5 mg (N = 30) | Velusetrag 15 mg (N = 29) | Velusetrag 30 mg (N = 26) |
|---|---|---|---|---|
| Week 4 Change From Baseline New GRS PRO Factor 1 | | | | |
| LS Mean (SE) | −0.9 (0.16) | −1.2 (0.16) | −1.2 (0.16) | −0.8 (0.17) |
| LS Mean Difference (SE) |  | −0.3 (0.22) | −0.2 (0.23) | 0.1 (0.23) |
| 95% CI for LS Mean Difference |  | −0.72, 0.16 | −0.66, 0.23 | −0.36, 0.55 |
| p-value vs. Placebo |  | 0.2156 | 0.3506 | 0.6876 |
| Week 8 Change From Baseline New GRS PRO Factor 1 | | | | |
| LS Mean (SE) | −1.2 (0.18) | −1.4 (0.18) | −1.2 (0.19) | −1.2 (0.19) |
| LS Mean Difference (SE) |  | −0.2 (0.25) | 0.0 (0.26) | 0.0 (0.26) |
| 95% CI for LS Mean Difference |  | −0.70, 0.28 | −0.50, 0.51 | −0.50, 0.52 |
| p-value vs. Placebo |  | 0.3959 | 0.9828 | 0.9803 |
| Week-12 Change From Baseline New GRS PRO Factor 1 | | | | |
| LS Mean (SE) | −1.3 (0.19) | −1.5 (0.19) | −1.3 (0.20) | −1.3 (0.20) |
| LS Mean Difference (SE) |  | −0.2 (0.27) | 0.0 (0.27) | −0.1 (0.27) |
| 95% CI for LS Mean Difference |  | −0.77, 0.27 | −0.53, 0.54 | −0.60, 0.49 |
| p-value vs. Placebo |  | 0.3502 | 0.9868 | 0.8451 |

There is a clear difference between velusetrag 5 mg and placebo for the diabetic gastroparesis subgroup.

2.10 Summary Score 2 for Diabetic Gastroparesis Population

Summary score 2 was evaluated in the group of patients affected by diabetic gastroparesis. Results are reported in Table 15.

TABLE 15

Summary Score 2 for Diabetic Gastroparesis Population

|  | Placebo (N = 31) | Velusetrag 5 mg (N = 30) | Velusetrag 15 mg (N = 29) | Velusetrag 30 mg (N = 26) |
|---|---|---|---|---|
| Week 4 Change From Baseline New GRS PRO Factor 2 | | | | |
| LS Mean (SE) | −0.8 (0.12) | −0.8 (0.12) | −0.7 (0.12) | −0.6 (0.13) |
| LS Mean Difference (SE) |  | −0.0 (0.16) | 0.1 (0.17) | 0.1 (0.17) |
| 95% CI for LS Mean Difference |  | −0.35, 0.30 | −0.20, 0.46 | −0.19, 0.48 |
| p-value vs. Placebo |  | 0.8984 | 0.4267 | 0.3901 |
| Week 8 Change From Baseline New GRS PRO Factor 2 | | | | |
| LS Mean (SE) | −0.9 (0.13) | −0.9 (0.12) | −0.6 (0.13) | −0.8 (0.13) |
| LS Mean Difference (SE) |  | 0.0 (0.18) | 0.3 (0.18) | 0.1 (0.18) |
| 95% CI for LS Mean Difference |  | −0.32, 0.37 | −0.08, 0.63 | −0.26, 0.46 |
| p-value vs. Placebo |  | 0.8907 | 0.1314 | 0.5879 |

TABLE 15-continued

Summary Score 2 for Diabetic Gastroparesis Population

|  | Placebo (N = 31) | Velusetrag 5 mg (N = 30) | Velusetrag 15 mg (N = 29) | Velusetrag 30 mg (N = 26) |
|---|---|---|---|---|
| Week-12 Change From Baseline New GRS PRO Factor 2 | | | | |
| LS Mean (SE) | −0.9 (0.12) | −1.0 (0.11) | −0.8 (0.12) | −1.1 (0.12) |
| LS Mean Difference (SE) |  | −0.1 (0.16) | 0.1 (0.17) | −0.2 (0.17) |
| 95% CI for LS Mean Difference |  | −0.46, 0.18 | −0.19, 0.47 | −0.51, 0.15 |
| p-value vs. Placebo |  | 0.3959 | 0.3934 | 0.2828 |

Only the 5 mg velusetrag group showed similar trends when compared to placebo; the 15 mg and 30 mg Velusetrag groups showed no worsening effect when compared to placebo.

2.11 Summary Score 1 for Idiopathic Gastroparesis Population

Summary score 1 was evaluated in the group of patients affected by idiopathic gastroparesis. Results are reported in Table 16.

TABLE 16

Summary Score 1 for Idiopathic Gastroparesis Population

|  | Placebo (N = 28) | Velusetrag 5 mg (N = 29) | Velusetrag 15 mg (N = 24) | Velusetrag 30 mg (N = 31) |
|---|---|---|---|---|
| Week 4 Change From Baseline New GRS PRO Factor 1 | | | | |
| LS Mean (SE) | −0.8 (0.17) | −1.3 (0.16) | −1.2 (0.18) | −0.8 (0.16) |
| LS Mean Difference (SE) |  | −0.5 (0.23) | −0.4 (0.25) | −0.0 (0.23) |
| 95% CI for LS Mean Difference |  | −0.98, −0.06 | −0.86, 0.12 | −0.50, 0.43 |
| p-value vs. Placebo |  | 0.0265 | 0.1335 | 0.8819 |
| Week 8 Change From Baseline New GRS PRO Factor 1 | | | | |
| LS Mean (SE) | −0.9 (0.19) | −1.4 (0.18) | −1.3 (0.20) | −1.1 (0.18) |
| LS Mean Difference (SE) |  | −0.4 (0.26) | −0.4 (0.28) | −0.2 (0.26) |
| 95% CI for LS Mean Difference |  | −0.96, 0.06 | −0.91, 0.18 | −0.71, 0.33 |
| p-value vs. Placebo |  | 0.0863 | 0.1916 | 0.4696 |
| Week-12 Change From Baseline New GRS PRO Factor 1 | | | | |
| LS Mean (SE) | −1.0 (0.20) | −1.5 (0.19) | −1.4 (0.22) | −1.1 (0.19) |
| LS Mean Difference (SE) |  | −0.5 (0.28) | −0.4 (0.29) | −0.1 (0.28) |
| 95% CI for LS Mean Difference |  | −1.04, 0.05 | −1.00, 0.15 | −0.66, 0.43 |
| p-value vs. Placebo |  | 0.0741 | 0.1462 | 0.6751 |

In contrast to the ITT analysis to the diabetic subgroup, both the 5 and the 15 mg Velusetrag groups showed similar efficacy, while only the 5 mg dose showed efficacy greater than placebo in the ITT and diabetic subgroup.

2.12 Summary Score 2 for Idiopathic Gastroparesis Population

Summary score 2 was evaluated in the group of patients affected by idiopathic gastroparesis. Results are reported in Table 17.

TABLE 17

Summary Score 2 for Idiopathic Gastroparesis Population

|  | Placebo (N = 28) | Velusetrag 5 mg (N = 29) | Velusetrag 15 mg (N = 24) | Velusetrag 30 mg (N = 31) |
|---|---|---|---|---|
| Week 4 Change From Baseline New GRS PRO Factor 2 | | | | |
| LS Mean (SE) | −0.6 (0.12) | −0.9 (0.12) | −0.8 (0.13) | −0.7 (0.12) |
| LS Mean Difference (SE) |  | −0.3 (0.17) | −0.2 (0.18) | −0.0 (0.17) |
| 95% CI for LS Mean Difference |  | −0.61, 0.07 | −0.53, 0.20 | −0.38, 0.30 |
| p-value vs. Placebo |  | 0.1195 | 0.3698 | 0.7987 |
| Week 8 Change From Baseline New GRS PRO Factor 2 | | | | |
| LS Mean (SE) | −0.7 (0.13) | −0.9 (0.13) | −0.9 (0.14) | −0.8 (0.13) |
| LS Mean Difference (SE) |  | −0.3 (0.18) | −0.2 (0.19) | −0.1 (0.18) |
| 95% CI for LS Mean Difference |  | −0.61, 0.11 | −0.62, 0.14 | −0.47, 0.24 |
| p-value vs. Placebo |  | 0.1710 | 0.2079 | 0.5286 |

TABLE 17-continued

Summary Score 2 for Idiopathic Gastroparesis Population

| | Placebo (N = 28) | Velusetrag 5 mg (N = 29) | Velusetrag 15 mg (N = 24) | Velusetrag 30 mg (N = 31) |
|---|---|---|---|---|
| Week-12 Change From Baseline New GRS PRO Factor 2 | | | | |
| LS Mean (SE) | −0.7 (0.12) | −1.0 (0.12) | −1.0 (0.13) | −0.9 (0.12) |
| LS Mean Difference (SE) | | −0.3 (0.17) | −0.3 (0.18) | −0.2 (0.17) |
| 95% CI for LS Mean Difference | | −0.60, 0.06 | −0.62, 0.08 | −0.48, 0.18 |
| p-value vs. Placebo | | 0.1138 | 0.1333 | 0.3671 |

For idiopathic gastroparesis group there was no diminution of effect over the time and no evidence of tachyphylaxis over 12 weeks of dosing.

The improvement in Summary Score 1 and Summary Score 2 was observed at Week 4 regardless of subgroups. A trend existed for greater effect as disease severity increased. A larger treatment effect was observed in subjects with higher baseline GCSI total score (≥3; moderate to very severe symptoms) compared to those with lower baseline GCSI total score (<3; none to mild symptoms) When considering the summary score change based on gastric emptying severity (mild, moderate, and severe) a greater response was observed in severity delayed subjects. No conclusions can be made on differences male and female subjects, as the number of male subjects in the study was small. In the individual symptoms, given the small size.

In the individual symptoms, given the small sizes, nominal marginal significance (<0.10) to statistical significance (<0.05) was observed for several of the subgroups for Summary Score 1. Similar trends were observed at Week 12. (FIGS. 26-35).

3.0 Results by Responder Analysis

A weekly responder was defined as a subject who experienced a clinically relevant change in symptoms from baseline. The response thresholds or MCIOs for change from baseline are summarized in Table 18.

TABLE 18

Responder Thresholds for Change from Baseline in Summary Score and Symptom Domains

| | Positive Response (Symptom Improvement) | Negative Response (Symptom Worsening) |
|---|---|---|
| Summary Score 1 | −1.00 | 1.25 |
| Summary Score 2 | −0.75 | 0.75 |
| Fullness/early satiety | −1.00 | 1.25 |
| Bloating | −0.75 | 1.00 |
| Upper abdominal pain | −1.25 | 1.25 |
| Epigastric burning | −1.00 | 1.25 |
| Nausea | −1.00 | 1.25 |
| Vomiting | −0.50 | 0.50 |

When viewing change in symptoms over the 12-week treatment period, on average, subjects achieved and maintained a maximal and stable response at approximately 6 weeks post-treatment initiation.

Given these observations, a responder is any subject being a weekly responder for at least 6 of 12 weeks and at least 3 of the last 4 weeks of treatment. Subjects with missing data in the week (drop out) were defined as a non-responder for that week.

3.1 Summary Score 1

More than half of subjects (54%) who received velusetrag 5 mg met the responder definition for Summary Score I The difference in the proportion of responders between velusetrag 5 mg (LS proportion: 0.53) and placebo (LS proportion: 0.37) was 16%, rendering subjects 1.9 times more likely to have demonstrated sustained clinical response in symptoms for the ITT analysis set (Table 16). For the weekly responders, velusetrag 5 mg had a higher response rate over placebo from Weeks 1 through 14. The differences between velusetrag 5 mg and placebo were statistically significant at Weeks 1 through 4 and Week 9.

A reverse dose-response trend was observed in both the overall responder and weekly responder summary, as the dose increased, the response rate decreased.

TABLE 19

Least-Squares Proportion of Positive Responders for Summary Score 1 (ITT Analysis Set)

| | Placebo (N = 59) | Velusetrag 5 mg (N = 59) | Velusetrag 15 mg (N = 53) | Velusetrag 30 mg (N = 57) |
|---|---|---|---|---|
| Responders for at least 6 of 12 weeks (Weeks 1-12) | | | | |
| Responders, n (%) | 22 (0.17) | 33 (55.9) | 26 (49.1) | 27 (47.4) |
| LS Proportion (SE) | 0.37 (0.06) | 0.54 (0.07) | 0.49 (0.07) | 0.44 (0.07) |
| Odds Ratio (VEL/Placebo) | — | 2.0 | 1.6 | 1.3 |
| p-value vs. Placebo | — | 0.0691 | 0.2126 | 0.4518 |

TABLE 19-continued

Least-Squares Proportion of Positive Responders
for Summary Score 1 (ITT Analysis Set)

| | Placebo (N = 59) | Velusetrag 5 mg (N = 59) | Velusetrag 15 mg (N = 53) | Velusetrag 30 mg (N = 57) |
|---|---|---|---|---|
| Responders for at least 6 of 12 weeks (Weeks 1-12) and for at least 3 weeks (Weeks 9-12) | | | | |
| Responders, n (%) | 22 (37.3) | 32 (54.2) | 24 (45.3) | 27 (47.4) |
| LS Proportion (SE) | 0.37 (0.06) | 0.53 (0.07) | 0.45 (0.07) | 0.44 (0.07) |
| Odds Ratio (VEL/Placebo) | — | 1.9 | 1.4 | 1.3 |
| p-value vs. Placebo | — | 0.1044 | 0.4002 | 0.4680 |

3.2 Summary Score 2

As with Summary Score 1, more than half of subjects (54%) who received velusetrag 5 mg met the responder definition for Summary Score 2. The difference in the proportion of responders between velusetrag 5 mg (LS proportion: 0.53) and placebo (LS proportion: 0.33) was 20%, rendering subjects 2.2 times more likely to have demonstrated sustained clinical response in symptoms for the ITT analysis set (Table 20). For the weekly responders, velusetrag 5 mg had a higher response rate over placebo from Weeks 1 through week 14. The differences between the 5-mg velusetrag group and the placebo group results were statistically significant at Weeks 2, 3, 7, 10, and 12.

TABLE 20

Least-Squares Proportion of Positive Responders
for Summary Score 2 (ITT Analysis Set)

| | Placebo (N = 59) | Velusetrag 5 mg (N = 59) | Velusetrag 15 mg (N = 53) | Velusetrag 30 mg (N = 57) |
|---|---|---|---|---|
| Responders for at least 6 of 12 weeks (Weeks 1-12) | | | | |
| Responders, n (%) | 24 (40.7) | 34 (57.6) | 27 (50.9) | 29 (50.9) |
| LS Proportion (SE) | 0.41 (0.07) | 0.57 (0.07) | 0.51 (0.07) | 0.47 (0.07) |
| Odds Ratio (VEL/Placebo) | — | 1.9 | 1.5 | 1.3 |
| p-value vs. Placebo | — | 0.0940 | 0.2861 | 0.5076 |
| Responders for at least 6 of 12 weeks (Weeks 1-12) and for at least 3 weeks (Weeks 9-12) | | | | |
| Responders, n (%) | 20 (33.3) | 32 (54.2) | 23 (43.4) | 28 (49.1) |
| LS Proportion (SE) | 0.33 (0.06) | 0.53 (0.07) | 0.43 (0.07) | 0.45 (0.07) |
| Odds Ratio (VEL/Placebo) | — | 2.2 | 1.5 | 1.6 |
| p-value vs. Placebo | — | 0.0397 | 0.3235 | 0.2167 |

The improvement in response rate was observed in both of the key subgroups, diabetic and idiopathic. Differences in treatment effect (odds ratios [ORs] for velusetrag/placebo) were similar between the 2 subgroups for Summary Score 1 (1.8-2.0), but were higher in the diabetic vs. idiopathic subgroup (2.3-2.6 vs. 1.6-1.9, respectively) for Summary Score 2.

3.3 Gastroparesis Subgroup

In the diabetic gastroparesis subgroup, the LS proportion of responders was 51% in the 5-mg velusetrag group for Summary Score 1 compared to 37% in the placebo group (OR: 1.8 [p=0.2871])

TABLE 21

Least-Squares Proportion of Positive Responders for
Summary Score 1 (Diabetic Gastroparesis Population)

| | Placebo (N = 59) | Velusetrag 5 mg (N = 59) | Velusetrag 15 mg (N = 53) | Velusetrag 30 mg (N = 57) |
|---|---|---|---|---|
| Evaluable N | 31 | 30 | 29 | 26 |
| Responders, n (%) | 12 (38.7) | 16 (53.3) | 13 (44.8) | 13 (50.0) |
| LS Proportion (SE) | 0.37 (0.09) | 0.51 (0.09) | 0.44 (0.09) | 0.48 (0.10) |
| Odds Ratio (VEL/Placebo) | — | 1.8 | 1.3 | 1.6 |
| p-value vs. Placebo | — | 0.2871 | 0.6021 | 0.4079 |

For Summary Score 2, the LS proportion of responders was 56% in the 5-mg velusetrag group compared to 33% in the placebo group (OR: 2.6 [p=0.0773]). The treatment effect was larger for Summary Score 2 responders in the diabetic subgroups as summarized in table 22.

TABLE 22

Least-Squares Proportion of Positive Responders for
Summary Score 2 (Diabetic Gastroparesis Population)

|  | Placebo (N = 59) | Velusetrag 5 mg (N = 59) | Velusetrag 15 mg (N = 53) | Velusetrag 30 mg (N = 57) |
| --- | --- | --- | --- | --- |
| Evaluable N | 31 | 30 | 29 | 26 |
| Responders, n (%) | 11 (35.5) | 18 (60.0) | 10 (34.5) | 13 (50.0) |
| LS Proportion (SE) | 0.33 (0.08) | 0.56 (0.10) | 0.31 (0.09) | 0.45 (0.10) |
| Odds Ratio (VEL/Placebo) | — | 2.6 | 0.9 | 1.7 |
| p-value vs. Placebo | — | 0.0773 | 0.8690 | 0.3383 |

3.4 Idiopathic Gastroparesis Subgroup

In the idiopathic gastroparesis subgroup, the LS proportion of responders was 54% in the 5-mg velusetrag group for Summary Score 1 compared to 38% of subjects in the placebo group (OR: 2.0 [p=0.2224]).

TABLE 23

Least-Squares Proportion of Positive Responders for
Summary Score 1 (Idiopathic Gastroparesis Population)

|  | Placebo (N = 59) | Velusetrag 5 mg (N = 59) | Velusetrag 15 mg (N = 53) | Velusetrag 30 mg (N = 57) |
| --- | --- | --- | --- | --- |
| Evaluable N | 28 | 29 | 24 | 31 |
| Responders, n (%) | 10 (35.7) | 16 (55.2) | 11 (45.8) | 14 (45.2) |
| LS Proportion (SE) | 0.38 (0.09) | 0.54 (0.09) | 0.48 (0.11) | 0.41 (0.09) |
| Odds Ratio (VEL/Placebo) | — | 2.0 | 1.5 | 1.1 |
| p-value vs. Placebo | — | 0.2224 | 0.4937 | 0.8158 |

For Summary Score 2, the LS proportion of responders was 50% in the 5-mg velusetrag group compared to 34% of subjects in the placebo group (OR: 1.9 [p=0.2469]) (Table 21).

TABLE 24

Least-Squares Proportion of Positive Responders for
Summary Score 2 (Idiopathic Gastroparesis Population)

|  | Placebo (N = 59) | Velusetrag 5 mg (N = 59) | Velusetrag 15 mg (N = 53) | Velusetrag 30 mg (N = 57) |
| --- | --- | --- | --- | --- |
| Evaluable N | 28 | 29 | 24 | 31 |
| Responders, n (%) | 9 (32.1) | 14 (48.3) | 13 (54.2) | 15 (48.4) |
| LS Proportion (SE) | 0.34 (0.09) | 0.50 (0.10) | 0.58 (0.11) | 0.45 (0.09) |
| Odds Ratio (VEL/Placebo) | — | 1.9 | 2.7 | 1.6 |
| p-value vs. Placebo | — | 0.2469 | 0.1039 | 0.3985 |

3.5 Gastric Emptying Tests

Overall, mean GES retention results on Day 28 were higher in the placebo group (range: 26.0%-81.2%) compared to all 3 of the velusetrag treatment groups.

Mean GES retention results decreased over time in all groups, with the lowest 4-hour retention result occurring in the 30-mg velusetrag group (9.5%). The GES results at Day 28 are shown in Table 25.

TABLE 25

Summary of Day 28 GES Retention by Hour (ITT Analysis Set)

|  | Placebo (N = 59) | Velusetrag 5 mg (N = 59) | Velusetrag 15 mg (N = 53) | Velusetrag 30 mg (N = 57) |
|---|---|---|---|---|
| 1-Hour Retention (%) | | | | |
| Evaluable, n | 23 | 23 | 19 | 21 |
| Mean (SD) | 81.2 (12.0) | 71.6 (15.9) | 65.3 (24.6) | 68.8 (14.6) |
| Median | 84.0 | 78.0 | 70.0 | 64.0 |
| Q1, Q3 | 70.0, 90.0 | 65.0, 81.4 | 50.4, 85.0 | 60.0, 81.9 |
| Min, Max | 59.7, 98.1 | 29.0, 95.0 | −5.0, 92.0 | 43.3, 98.0 |
| LS Mean (SE) | 78.5 (5.2) | 68.4 (4.4) | 61.0 (5.7) | 66.3 (5.6) |
| LS Mean Difference (SE) | — | −10.2 (5.3) | −17.5 (5.6) | −12.3 (5.8) |
| 95% Cl for LS Mean Difference | — | −20.8, 0.4 | −28.7, −6.4 | −23.8, −0.7 |
| p-value vs. Placebo | — | 0.0597 | 0.0025 | 0.0374 |
| 2-Hour Retention (%) | | | | |
| Evaluable, n | 23 | 23 | 19 | 21 |
| Mean (SD) | 62.2 (18.0) | 43.3 (23.2) | 40.8 (30.7) | 40.6 (20.0) |
| Median | 67.5 | 42.0 | 37.6 | 38.0 |
| Q1, Q3 | 53.0, 75.7 | 20.0, 60.3 | 13.0, 66.0 | 29.0, 56.0 |
| Min, Max | 20.5, 84.5 | 12.0, 84.0 | 0.7, 95.0 | 5.0, 76.0 |
| LS Mean (SE) | 59.7 (5.3) | 41.9 (4.7) | 36.1 (5.5) | 37.2 (5.4) |
| LS Mean Difference (SE) | — | −17.9 (7.0) | −23.7 (7.3) | −22.5 (7.4) |
| 95% Cl for LS Mean Difference | — | −31.8, −4.0 | −38.2, −9.2 | −37.3, −7.9 |
| p-value vs. Placebo | — | 0.0123 | 0.0017 | 0.0031 |
| 3-Hour Retention (%) | | | | |
| Evaluable, n | 16 | 15 | 11 | 20 |
| Mean (SD) | 45.7 (19.7) | 22.4 (22.0) | 17.0 (18.4) | 17.9 (14.2) |
| Median | 45.1 | 19.0 | 3.7 | 12.0 |
| Q1, Q3 | 32.0, 61.0 | 5.7, 35.0 | 3.0, 34.1 | 7.5, 26.5 |
| Min, Max | 7.0, 78.0 | 0.0, 69.0 | 1.0, 53.0 | 1.3, 47.0 |
| LS Mean (SE) | 45.5 (4.6) | 23.1 (4.5) | 26.2 (4.9) | 19.7 (4.8) |
| LS Mean Difference (SE) | — | −22.5 (6.3) | −19.3 (6.7) | −25.9 (6.6) |
| 95% Cl for LS Mean Difference | — | −35.1, −9.9 | −32.6, −6.1 | −39.1, −12.6 |
| p-value vs. Placebo | — | 0.0007 | 0.0048 | 0.0002 |
| 4-Hour Retention (%) | | | | |
| Evaluable, n | 23 | 23 | 20 | 21 |
| Mean (SD) | 26.0 (18.1) | 10.6 (14.6) | 10.8 (20.6) | 9.5 (13.2) |
| Median | 23.3 | 3.1 | 2.3 | 3.1 |
| Q1, Q3 | 8.1, 44.0 | 1.0, 16.0 | 1.0, 14.5 | 1.6, 12.0 |
| Min, Max | 0.0, 55.0 | 0.0, 60.0 | 0.0, 90.0 | 0.0, 45.0 |
| LS Mean (SE) | 29.5 (4.0) | 13.4 (3.9) | 16.1 (4.2) | 12.4 (4.3) |
| LS Mean Difference (SE) | — | −16.1 (5.0) | −13.4 (5.2) | −17.2 (5.4) |

TABLE 26

Summary of Day 28 GES Retention by Hour (ITT Analysis Set)

|  | Placebo (N = 59) | Velusetrag 5 mg (N = 59) | Velusetrag 15 mg (N = 53) | Velusetrag 30 mg (N = 57) |
|---|---|---|---|---|
| 95% Cl for LS Mean Difference | — | −26.0, −6.2 | −23.9, −3.0 | −27.8, −6.5 |
| p-value vs. Placebo | — | 0.0017 | 0.0123 | 0.0020 |

Shifts of GES severity from screening are summarized in Table 27. Comparing baseline and Day 28 GES values at Hour 4, only 3% of subjects in the velusetrag treatment groups worsened compared to 30% in the placebo treatment group.

TABLE 27

Shift of GES Severity from Screening (ITT Analysis Set)

| Baseline | | Post-baseline: Day 28 | | | | |
|---|---|---|---|---|---|---|
| | Value | <10 | 10, <20 | 20, <35 | 35 | Total |
| Placebo (N = 23) | 10, <20 | 0 | 0 | 7 | 0 | 7 |
| | 20, <35 | 0 | 0 | 8 | 0 | 8 |
| | 35 | 0 | 0 | 8 | 0 | 8 |
| | Total | 0 | 0 | 23 | 0 | 23 |
| VEL 5 mg (N = 23) | 10, <20 | 3 | 4 | 0 | 0 | 7 |
| | 20, <35 | 4 | 4 | 0 | 0 | 8 |
| | 35 | 3 | 5 | 0 | 0 | 8 |
| | Total | 10 | 13 | 0 | 0 | 23 |
| VEL 15 mg (N = 20) | 10, <20 | 2 | — | 2 | 0 | 5 |
| | 20, <35 | 4 | 0 | — | 0 | 5 |
| | 35 | 7 | 1 | 2 | 0 | 10 |
| | Total | 13 | 2 | 5 | 0 | 20 |

TABLE 27-continued

Shift of GES Severity from Screening (ITT Analysis Set)

| Baseline | | Post-baseline: Day 28 | | | | |
|---|---|---|---|---|---|---|
| | Value | <10 | 10, <20 | 20, <35 | 35 | Total |
| VEL 30 mg (N = 21) | 10, <20 | 6 | 0 | 0 | 0 | 6 |
| | 20, <35 | 8 | 0 | 0 | 0 | 8 |
| | 35 | 1 | 6 | 0 | 0 | 7 |
| | Total | 15 | 6 | 0 | 0 | 21 |

3.6 Summary of Efficacy in Gastric Emptying

As secondary endpoint evaluated the change in gastric emptying for the subset of subjects who underwent GES during Screening and completed a Day 28 GES (approximately half of the subjects within each treatment group) was evaluated. Results are summarized in Table 28.

All subjects in the placebo group were delayed at Day 28, with none normalizing their gastric delay. Normalization was defined as not meeting the criteria for gastric delay (>10% retention at Hour 4 by GES). In contrast, using the Flour 4 assessment, all 3 dose levels of velusetrag resulted in marked and notable proportions of subjects with normalization of gastric function, 44%, 65%, and 71% of subjects for the 5-mg, 15-mg, and 30-mg velusetrag groups, respectively.

TABLE 28

Summary of Gastric emptying Scintigraphy Hour 4 Percentage Retention (Subset of subjects with Day 28 Scintigraphy)

| | Placebo (N = 23) | VEL 5 mg (N = 23) | VEL 15 mg (N = 20) | VEL 30 mg (N = 21) |
|---|---|---|---|---|
| LS Mean Change from Baseline (SE), n (%) | 29.5 (4.0) | 13.4 (3.9) | 16.1 (4.2) | 12.4 (4.3) |
| GES Delay NORMAL at Hour 4 (<10%), n (%) | 0 | 10 (43.5) | 13 (65.0) | 15 (71.4) |
| GES Delay MILD at Hour 4 (≥10, <20%), n (%) | 0 | 13 (56.5) | 2 (10.0) | 6 (28.6) |
| GES Delay MODERATE at Hour 4 (≥20, <35%), n (%) | 23 (100.0) | 0 | 5 (25.0) | 0 |
| GES Delay SEVERE at Hour 4 (≥35%), n (%) | 0 | 0 | 0 | 0 |
| p-value vs. Placebo | | <0.0001 | <0.0001 | <0.0001 |

4.0 Safety Analysis 4.1 Adverse Events

An overview of the treatment-emergent adverse events is presented in Table 29. Treatment emergent adverse events were reported in at least 50% of subjects in each treatment group; the proportion was lowest in the 30 mg velusetrag group (50.0%). The majority of adverse events were mild and unrelated to study drug. The incidence of adverse events leading to discontinuation of study drug was low, and no treatment-emergent adverse events led to death during study. Velusetrag 5 mg led to the lowest frequency of study drug discontinuation due to an adverse event, of moderate or severe adverse events, as well as the frequency of adverse events deemed possibly related to study drug.

TABLE 29

Overall summary of treatment emergent adverse events

| | Placebo (N = 23) | VEL 5 mg (N = 23) | VEL 15 mg (N = 20) | VEL 30 mg (N = 21) |
|---|---|---|---|---|
| LS Mean Change from Baseline (SE), n (%) | 29.5 (4.0) | 13.4 (3.9) | 16.1 (4.2) | 12.4 (4.3) |

TABLE 29-continued

Overall summary of treatment emergent adverse events

|  | Placebo (N = 23) | VEL 5 mg (N = 23) | VEL 15 mg (N = 20) | VEL 30 mg (N = 21) |
|---|---|---|---|---|
| GES Delay NORMAL at Hour 4 (<10%), n (%) | 0 | 10 (43.5) | 13 (65.0) | 15 (71.4) |
| GES Delay MILD at Hour 4 (≥10, <20%), n (%) | 0 | 13 (56.5) | 2 (10.0) | 6 (28.6) |
| GES Delay MODERATE at Hour 4 (≥20, <35%), n (%) | 23 (100.0) | 0 | 5 (25.0) | 0 |
| GES Delay SEVERE at Hour 4 (≥35%), n (%) | 0 | 0 | 0 | 0 |
| p-value vs. Placebo |  | <0.0001 | <0.0001 | <0.0001 |

4.2 Study Safety and Tolerability

A total of 232 subjects with either idiopathic or diabetic gastroparesis were dosed with at least one dose of velusetrag. No significant adverse events were reported in the DIGEST I study.

The nonclinical and clinical data supports the potential for velusetrag to treat gastroparesis. Because velusetrag is a highly selective $5\text{-}HT_4$ receptor agonist with 3,000-fold higher intrinsic activity for the $5\text{-}HT_4$ receptor vs. $5\text{-}HT_3$ receptor and 70-fold intrinsic activity vs. other serotonergic receptor subtypes, there is low likelihood for adverse reactions associated with other 5-HT subtypes to be observed with velusetrag. Velusetrag has low risk for off-target effects with no effects on coronary artery tone (across multiple species including human) or platelet aggregation.

Velusetrag was generally well-tolerated with no evidence of safety signals based on collected data. Velusetrag has demonstrated improvements across all the cardinal symptoms of gastroparesis in both idiopathic and diabetic subjects. There was no observed evidence of tachyphylaxis or diminution of treatment effect over 12 weeks of therapy suggestive that velusetrag may provide the first chronic maintenance therapy for the symptoms of gastroparesis.

Velusetrag presents an opportunity to provide patients with gastroparesis a robust once-daily oral option to improve their symptoms, gastric delay, and overall quality of life and potentially reduce the overall mortality associated with the disease-state.

In summary, the treatment with velusetrag resulted in numerical improvements in all the core symptoms of gastroparesis: fullness/early satiety, bloating, upper abdominal pain, epigastric burning, nausea, and vomiting. A reverse dose response was observed in the majority of symptom domains for the GCS1-24H and the GRS PROs where the 5-mg group had the largest reduction in symptoms compared to the 15- and 30-mg dose groups. The reverse dose response pattern was also observed in the summary scores. Only the 5-mg dose showed nominal statistical improvements relative to placebo for the summary scores.

Velusetrag 5 mg showed nominally statistically significant differences (reductions signifying improvements) in the Week 4 GCS1-24H total score (−0.4 points [95% CI: −0.75, −0.03; p=0.0327] compared to placebo (designated primary endpoint). At Week 12, the reductions, compared to placebo, were numerical (−0.3 points [95% CI: −0.73, 0.10; p=0.1331]).

Velusetrag 5 mg showed nominally statistically significant differences in the Week 4 GRS Summary Score 1 (−0.4 points [95% CI: −0.72, −0.08; p=0.0143]) compared to placebo. The numerical effect was maintained at Week 12 (End of Therapy) (−0.4 points [95% CI: −0.75, 0.01; p=0.0536]). Velusetrag 5 mg showed numerical differences in the Week 4 GRS Summary Score 2 (−0.1 points [95% CI: −0.38, 0.09; p=0.2240]) compared to placebo. At Week 12, numerical reductions were observed (−0.2 points [95% CI: −0.43, 0.03; p=0.0841]) compared to placebo.

Furthermore, velusetrag at 5 and 15 mg daily dosage showed a greater point reduction of the GCSI-24H total score, expressing a greater effectiveness, in the idiopathic subgroup of patients than in the diabetic subgroup. A 0.3 points reduction has been observed at 14 weeks following 5 mg treatment in the idiopathic subgroup, and 0.3 points reduction has been observed at 8 weeks following 15 mg treatment.

By analysis of the GRS summary scores, the velusetrag 5-mg group had a responder rate (defined as having at least a 1-point improvement from baseline for at least 6 of 12 weeks and at least 3 of the last 4 weeks of treatment) of 53% for GRS Summary Score 1 compared to 37% for placebo, resulting in a 16% improvement in the difference in proportions or an odds ratio of 1.9 (i.e., subjects on velusetrag 5 mg were 1.9 times more likely to observe a clinically relevant reduction in symptom scores than on placebo for the ITT analysis set). Likewise, for GRS Summary Score 2, the difference in proportions (response rates) between the velusetrag 5-mg group and placebo group was 20%, with subjects 2.2 times more likely to have demonstrated a clinically relevant reduction in symptom scores relative to placebo for the ITT analysis set. Differences in responder proportions were numerical and not statistically powered for a robust inference.

Velusetrag 5 mg showed improvements in symptoms of postprandial fullness, early satiety, bloating, upper abdominal pain, epigastric burning, nausea and vomiting. In the 5 mg velusetrag group, the change from baseline for every symptom was observed within the first week and continued to improve through week 6, stabilizing through week 12 (end of therapy). No tachyphylaxis effect was observed. Larger effects were observed in GRS Summary score 1 relative to Summary score 2 as noted in the individual symptom domain where nausea and vomiting were the least affected symptom domains likely due to the low baseline scores in these domains, though trends for improvement were noted in these two symptoms.

Improvement in symptoms was observed in both key subgroups (diabetic gastroparesis and idiopathic gastroparesis). The change from baseline in GRS Summary Score 1 for each treatment group showed no difference between subgroups (−1.5 points for the diabetic group and −1.5 points for the idiopathic group). A similar pattern was observed in GRS Summary Score 2 where there was no to minimal difference in change from baseline in the velusetrag groups compared to the placebo group. However, a difference was observed in the placebo response with the diabetic subgroup having a larger placebo response relative to the idiopathic subgroup, resulting in a higher treatment effect in the idiopathic subgroup, although there was no difference in baseline or change from baseline between the 2 subgroups.

Overall, for subjects who qualified by GES criteria and had an evaluable Day 28 GES assessment, the Hour 4 percentage retention (LS mean[±SE]) was higher in the placebo group (29.5% [4.0%]) compared to the velusetrag treatment groups (range: 12.4% [4.3%] to 16.1% [4.2%] in a dose-dependent manner) signifying higher gastric delay in the placebo group relative to the velusetrag groups at Day 28. All 3 dose levels of velusetrag showed normalization of gastric emptying, defined as a 4-hour gastric retention percentage of <10% in a statistically higher number of subjects (44%-71% in a dose-dependent manner) compared to placebo (0%).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A method for reducing diabetic gastroparesis or idiopathic gastroparesis symptoms in a human patient with delayed gastrointestinal emptying (GE), and symptoms consisting of one or more of epigastric burning, and gastric reflux with or without burning, and bowel movements, the method comprising administering to the human patient, for a treatment period of at least 2 weeks about 5.0 mg/day of 1-isopropyl-2-oxo-1,2-dihydroquinoline-3-caboxylic acid {(1S,3R,5R)-8-[(R)-2-hydroxy-3-(methanesulfonyl-methyl-amino)propyl]-8-azabicyclo[3.2.1]oct-3-yl}amide (velusetrag), wherein velusestrag is a crystalline hydrochloride salt hydrate, wherein velusetrag is administered orally at least one dosage unit per day, and wherein the symptoms are measured using Gastroparesis Cardinal Symptom Index (GCSI) and/or Gastroparesis Rating Scale (GRS).

2. The method of claim 1, wherein the reduction of symptom from baseline GCSI-24 H score in the idiopathic patent at Week 4 is about 0.6 points with daily dosage of about 5 mg velusetrag compared to placebo.

3. The method of claim 1, wherein a change from baseline in daily and 7-day mean composite GCSI-24 H score in the idiopathic patent is maintained along the treatment time at daily dosage of about 5 mg velusetrag compared to placebo.

4. The method of claim 1, wherein a change from baseline in daily and 7-day mean composite GCSI-24 H score in the diabetic patient is higher than 0.2 points at week 4 at daily dosage of about 5 mg velusetrag compared to placebo.

5. The method of claim 1, wherein the treatment period is 8 weeks or longer and the change from baseline in daily and 7-day mean composite GCSI-24 H score in diabetic patents is higher than 0.1 points at week 8 at daily dosage of about 5 mg velusetrag compared to placebo.

6. The method of claim 1, wherein a change from baseline in daily and 7-day mean composite GCSI-24 H score in diabetic patients is maintained along the treatment time at daily dosage of about 5 mg velusetrag compared to placebo.

7. The method of claim 1, wherein a change from baseline in daily and 7-day mean composite GCSI-24 H score in the idiopathic patient is higher than in the diabetic patient at daily dosage of about 5 mg velusetrag.

8. The method of claim 1, wherein a change from baseline in daily and 7-day mean composite GCSI-24 H score in the idiopathic patient is higher than 0.3 points at week 14 at daily dosage of about 5 mg velusetrag compared to diabetic patients.

9. The method of claim 1, wherein the administering of velusetrag provides at least 1-point improvement from baseline in the GRS individual component in the treatment line.

10. The method of claim 1, wherein the symptoms comprise epigastric burning with a GRS total score higher than 0.4 compared to placebo.

11. The method of claim 1, wherein a symptom GRS total score change from baseline is in a level of total symptom burden from severe symptoms to moderate/mild symptoms, or from mild to moderate symptoms.

12. The method of claim 1, wherein the treatment with velusetrag or a pharmaceutically-acceptable salt thereof in the human patient does not cause a significant increase in hyperglycemia or glucose in the blood.

13. The method of claim 1, wherein velusetrag is administered with or without food.

14. The method of claim 1, wherein velusetrag is administered to the patient once daily for at least four weeks.

15. The method of claim 14, wherein velusetrag is administered to the patient once daily for at least eight weeks.

16. The method of claim 14, wherein velusetrag is administered to the patient once daily for two to twelve weeks.

17. The method of claim 1, wherein velusetrag is administered orally by capsule.

18. A method for reducing idiopathic gastroparesis symptoms in an idiopathic human patient with delayed gastrointestinal emptying (GE) and symptoms consisting of one or more of epigastric burning, gastric reflux with or without burning and bowel movements, the method comprising
administering to the idiopathic human patient, for a treatment period of at least 2 weeks about 5.0 mg/day of 1-isopropyl-2-oxo-1,2-dihydroquinoline-3-caboxylic acid {(1 S,3R,5R)-8-[(R)-2-hydroxy-3-(methanesulfonyl-methyl-amino)propyl]-8-azabicyclo[3.2.1]oct-3-yl}amide (velusetrag),
wherein velusetrag is a crystalline hydrochloride salt hydrate, wherein velusetrag is administered orally at least one dosage unit per day, and wherein the symptoms are measured using Gastroparesis Cardinal Symptom Index (GCSI) and/or Gastroparesis Rating Scale (GRS).

19. A method for reducing diabetic gastroparesis or idiopathic gastroparesis symptoms in a human patient with delayed gastrointestinal emptying (GE), and symptoms consisting of epigastric burning, the method comprising
administering to the human patient, for a treatment period of at least 2 weeks about 5.0 mg/day of 1-isopropyl-2-oxo-1,2-dihydroquinoline-3-caboxylic acid {(1 S,3R,5R)-8-[(R)-2-hydroxy-3-(methanesulfonyl-methyl-amino)propyl]-8-azabicyclo[3.2.1]oct-3-yl}amide (velusetrag), wherein velusestrag is a crystalline hydrochloride salt hydrate, wherein velusetrag is administered orally at least one dosage unit per day, and wherein the symptoms are measured using Gastroparesis Cardinal Symptom Index (GCSI) and/or Gastroparesis Rating Scale (GRS).

* * * * *